United States Patent [19]

Flynn et al.

[11] Patent Number: 5,488,048
[45] Date of Patent: Jan. 30, 1996

[54] AMINOACETYLMERCAPTO DERIVATIVES USEFUL AS INHIBITORS OF ENKEPHALINASE AND ACE

[75] Inventors: Gary A. Flynn, Cincinnati; Robert J. Cregge, Loveland; Thomas L. Fevig, West Chester; Shyam Sunder, Cincinnati; Patrick W. Shum, West Chester, all of Ohio

[73] Assignee: Merrell Dow Pharmaceuticals Inc., Cincinnati, Ohio

[21] Appl. No.: 396,999

[22] Filed: Mar. 1, 1995

Related U.S. Application Data

[60] Division of Ser. No. 119,924, Sep. 10, 1993, Pat. No. 5,424,425, which is a continuation-in-part of Ser. No. 985,678, Dec. 11, 1992, abandoned, which is a continuation-in-part of Ser. No. 836,028, Feb. 14, 1992, abandoned.

[51] Int. Cl.⁶ .......................... C07D 498/04; A01K 31/55
[52] U.S. Cl. ........................... 514/214; 540/521; 540/522
[58] Field of Search ................................. 514/214

Primary Examiner—Robert T. Bond
Attorney, Agent, or Firm—Charlotte L. Barney

[57] ABSTRACT

The present invention relates to novel aminoacetylmercapto derivatives useful as inhibitors of enkephalinase and ACE.

1 Claim, No Drawings

AMINOACETYLMERCAPTO DERIVATIVES USEFUL AS INHIBITORS OF ENKEPHALINASE AND ACE This is a division, of application Ser. No. 08/119,924, filed Sep. 10, 1993, now U.S. Pat. No. 5,424,425, which is a CIP of application Ser. No. 07/985,678, filed Dec. 11, 1992, now abandoned; which is a CIP of application Ser. No. 07/836,028, filed Feb. 14, 1992 now abandoned—which is herein incorporated by reference.

Enkephalinase or, more specifically, endopeptidase-24.11, is a mammalian ectoenzyme which is involved in the metabolic degradation of certain circulating regulatory peptides. This enzyme, which is a $Zn+^2$-metallopeptidase, exerts its effect by cleaving the extracellular peptides at the amino group of hydrophobic residues and thus inactivates the peptides as regulatory messengers.

Enkephalinase is involved in the metabolic degradation of a variety of circulating regulatory peptides including endorphins, such as β-endorphin and the enkephalins, atrial natriuretic peptide (ANP), bradykinin and other circulating regulatory peptides.

Endorphins are naturally-occurring polypeptides which bind to opiate receptors in various areas of the brain and thereby provide an analgesic effect by raising the pain threshold. Endorphins occur in various forms including α-endorphin, β-endorphin, γ-endorphin as well as the enkephalins. The enkephalins, i.e., Met-enkephalins and Leu-enkephalin, are pentapeptides which occur in nerve endings of brain tissue, spinal cord and the gastrointestinal tract. Like the other endorphins, the enkephalins provide an analgesic effect by binding to the opiate receptors in the brain. By inhibiting enkephalinase, the metabolic degradation of the naturally-occurring endorphins and enkephalins are inhibited, thereby providing a potent endorphin- or enkephalin-mediated analgesic effect. Inhibition of enkephalinase would therefore be useful in a patient suffering from acute or chronic pain. Inhibition of enkephalinase would also be useful in providing an antidepressant effect and in providing a reduction in severity of withdrawal symptoms associated with termination of opiate or morphine administration. In addition, inhibition of enkephalinase would also be useful in the treatment of irritable bowel syndrome ANP refers to a family of naturally-occurring peptides which are involved in the homeostatic regulation of blood pressure, as well as sodium and water levels. ANP have been found to vary in length from about 21 to about 126 amino acids with a common structural feature being one or more disulfide-looped sequences of 17 amino acids with various amino- and carboxy-terminal sequences attached to the cystine moiety. ANP have been found to bind to specific binding sites in various tissues including kidney, adrenal, aorta, and vascular smooth muscle with affinities ranging from about 50 pico-molar (pM) to about 500 nano-molar (nM) [Needleman, *Hypertension*, 7 469 (1985)]. In addition, it is believed that ANP binds to specific receptors in the brain and possibly serves as a neuromodulator as well as a conventional peripheral hormone.

The biological properties of ANP involve potent diuretic/natriuretic and vasodilatory/hypotensive effects as well as an inhibitory effect on renin and aldosterone secretion [deBold, *Science* 230, 767 (1985)]. By inhibiting enkephalinase, the metabolic degradation of the naturally-occurrring ANP are inhibited, thereby providing a potent ANP-mediated diuretic, natriuretic, hypotensive, hypoaldosteronemic effects. Inhibition of enkephalinase would therefore be useful in a patient suffering from disease states characterized by abnormalities in fluid, electrolyte, blood pressure, intraocular pressure, renin, or aldosterone homeostasis, such as, but not limited to, hypertension, renal diseases, hyperaldosteronemia, cardiac hypertrophy, glaucoma and congestive heart failure.

In addition, the compounds of the present invention are inhibitors of Angiotensin-Converting Enzyme (ACE). ACE is a peptidyl dipeptidase which catalyzes the conversion of angiotensin I to angiotensin II as well as causing the degradation of bradykinin. Angiotensin II is a vasoconstrictor which also stimulates aldosterone secretion by the adrenal cortex. Inhibition of ACE would therefore be useful in a patient suffering from disease states such as hypertension and congestive heart failure [See William W. Douglas, "Polypeptides—Angiotensin, Plasma Kinins, and Others", Chapter 27, in GOODMAN AND GILLMAN'S THE PHARMACOLOGICAL BASIS OF THERAPEUTICS, 7th edition, 1985, pp. 652–3, MacMillan Publishing Co., New York, N.Y.]. In addition, it has been discovered that ACE inhibitors are useful in treating cognitive disorders [German Application No. 3901-291-A, published Aug. 3, 1989].

Bradykinin refers to a naturally-occurring peptide which is a very powerful vasodilator and causes increased capillary permeability. By inhibiting enkephalinase and ACE, the metabolic degradation of bradykinin is inhibited, thereby providing increased levels of bradykinin in the circulation.

In addition, the compounds of the present invention are useful as inhibitors of smooth cell proliferation. Smooth muscle cell proliferation in the intima of muscular arteries a primary cause of vascular stenosis in arteriosclerosis, after vascular surgery, and after coronary angioplasy. Several animal studies have indicated the renin-angiotensin system plays an important role in this vascular response to injury. Chronic treatment with angiotensin converting enzyme (ACE) inhibitors reduced myointimal thickening following balloon injury in rat carotid artery or aorta. Powell, J. S., Muller, R. K. M. and Baumgartner, H. R.; Suppression of the vascular response to injury: The role of angiotensin-converting enzyme inhibitors. J. Am. Coll. Cardiol. 17:137B-42B, 1991. More recently, atrial natruiuretic peptide (ANP) has been found to decrease myointimal proliferation. ANP is rapidly metabolized by receptor mediated clearance and by neutral endopeptidase (NEP). Inhibition of NEP significantly reduces proliferation in the balloon-injured rabbit vasculature. Davis, H. R., McGregor, D. C., Hoos, L., Mullins, D. E. and Sybertz, E. J.: Atrial naturiuretic factor and the neutral endopeptidase inhibitor SCH42495 prevent myointimal proliferation after vascular injury. Circ. 86:I-220, 1992. These studies imply that a dual inhibitor of ACE and NEP should be therapeutically useful in the treatment of conditions which require inhibition of smooth cell proliferation. Davis and Sybertz, European Patent Application 533084-A1, Mar. 24, 1993.

SUMMARY OF THE INVENTION

The present invention provides novel compounds of the Formula (I )

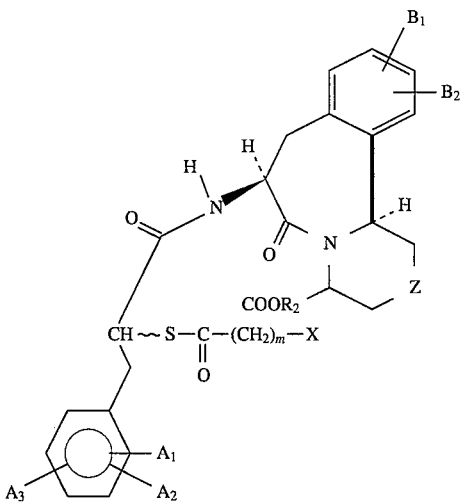

wherein
- $B_1$ and $B_2$ are each independently hydrogen; hydroxy; $-OR_1$ wherein $R_1$ is a $C_1-C_4$ alkyl or an Ar—Y— group wherein Ar is aryl and Y is a $C_0-C_4$ alkyl; or, where $B_1$ and $B_2$ are attached to adjacent carbon atoms, $B_1$ and $B_2$ can be taken together with said adjacent carbons to form a benzene ring or methylenedioxy;
- $A_1$, $A_2$ and $A_3$ are each independently hydrogen; hydroxy; nitro; amino; fluoro, chloro, $-OR_1$ or an Ar—Y group; or, where $A_1$ and $A_2$ are attached to adjacent carbon atoms, $A_1$ and $A_2$ can be taken together with said adjacent carbons to form a benzene ring or methylenedioxy;
- $R_2$ is hydrogen, a $C_1-C_4$ alkyl, an Ar—Y— group or $-CH_2O-C(O)C(CH_3)_3$;
- Z is $-CH_2-$, $-O-$, $-S-$,

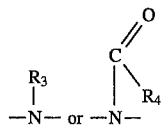

or a bond
wherein
- $R_3$ is hydrogen, a $C_1-C_4$ alkyl or an Ar—Y— group and $R_4$ is $-CF_3$, a $C_1-C_{10}$ alkyl or an Ar—Y— group;
- m is an integer 0 to 5;
- X is selected from the group consisting of

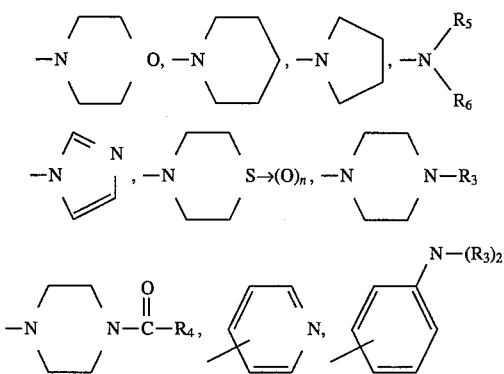

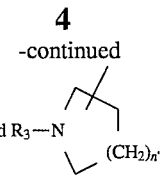

wherein
$R_5$ and $R_6$ are each independently a $C_1-C_4$ alkyl or an Ar—Y— group and n is an integer 0–2; n' is an integer 1–2; and the pharmaceutically acceptable salts thereof.

The present invention further provides a method of inhibiting enkephalinase in a patient in need thereof comprising administering to said patient an effective enkephalinase inhibitory amount of a compound of Formula (I). The present invention also provides a method of inhibiting ACE in a patient in need thereof comprising administering to said patient an effective ACE inhibitory amount of a compound of Formula (I).

In addition, the present invention provides a composition comprising an assayable amount of a compound of Formula (I) in admixture or otherwise in association with an inert carrier. The present invention also provides a pharmaceutical composition comprising an effective inhibitory amount of a compound of Formula (I) in admixture or otherwise in association with one or more pharmaceutically acceptable carriers or excipients.

DETAILED DESCRIPTION OF THE INVENTION

As used herein, the term "$C_1-C_4$ alkyl" refers to a saturated straight or branched chain hydrocarbyl radical of one to four carbon atoms and includes methyl, ethyl, propyl, isopropyl, n-butyl, isobutyl, tertiary butyl and the like. The term "$C_1-C_{10}$ alkyl" refer to saturated straight or branched chain hydrocarbyl radicals of one to ten carbon atoms, respectively, including methyl, ethyl, propyl, isopropyl, n-butyl, isobutyl, tertiary butyl, pentyl, isopentyl, hexyl, 2,3-dimethyl-2-butyl, heptyl, 2,2-dimethyl- 3-pentyl, 2-methyl-2-hexyl, octyl, 4-methyl-3-heptyl, octyl, nonyl, or decyl and the like. The term "halogen", "halo", "halide" or "Hal" refers to a chlorine, bromine, or iodine atom. The term "BOC" refers to t-butyloxycarbonyl. The term "$C_1-C_4$ alkoxy" refers to a saturated straight or branched chain hydrocarboxy radical of one to four carbon atoms and includes methoxy, ethoxy, propoxy, isopropoxy, n-butoxy, isobutoxy, tertiary butoxy and the like.

As used herein, the term "Ar—Y—" refers to a radical wherein Ar is an aryl group and Y is a $C_0-C_4$ alkyl. The term "Ar" refers to a phenyl or naphthyl group unsubstituted or substituted with from one to three substituents selected from the group consisting of methylenedioxy, hydroxy, $C_1-C_4$ alkoxy, fluoro and chloro. The term "$C_0-C_4$ alkyl" refers to a saturated straight or branched chain hydrocarbyl radical of zero to four carbon atoms and includes a bond, methyl, ethyl, propyl, isopropyl, n-butyl, isobutyl, tertiary butyl and the like. Specifically included within the scope of the term "Ar—Y—" are phenyl, naphthyl, phenylmethyl or benzyl, phenylethyl, p-methoxybenzyl, p-fluorobenzyl and p-chlorobenzyl.

As used herein, the designation "~~" refers to a bond to a chiral atom for which the stereochemistry is not designated.

Compounds of Formula (I) can form pharmaceutically acceptable salts with any non-toxic, organic or inorganic acid. Illustrative inorganic acids which form suitable salts include hydrochloric, hydrobromic, sulphuric and phosphoric acid and acid metals salts such as sodium monohydrogen orthophosphate and potassium hydrogen sulfate. Illustrative organic acids which form suitable salts include the mono, di and tricarboxylic acids. Illustrative of such acids are, for example, acetic, trifluoroacetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salacylic, 2-phenoxybenzoic and sulfonic acids such as methane sulfonic, trifluoromethane sulfonic, 2-hydroxyethane sulfonic acid and p-toluenesulfonic acid.

The compounds of Formula (I) can be prepared by utilizing procedures and techniques well known and appreciated by one of ordinary skill in the art. A general synthetic scheme for preparing these compounds is set forth in Scheme A wherein all substituents are as previously defined unless otherwise defined.

Scheme A

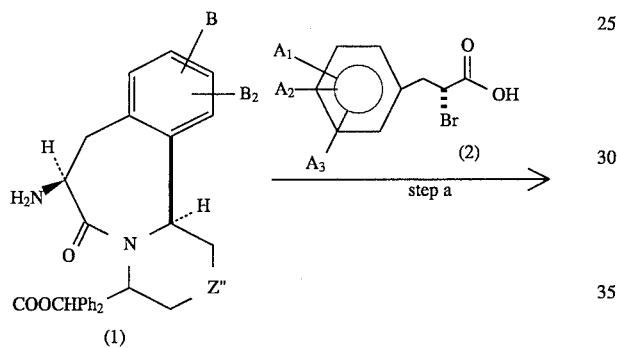

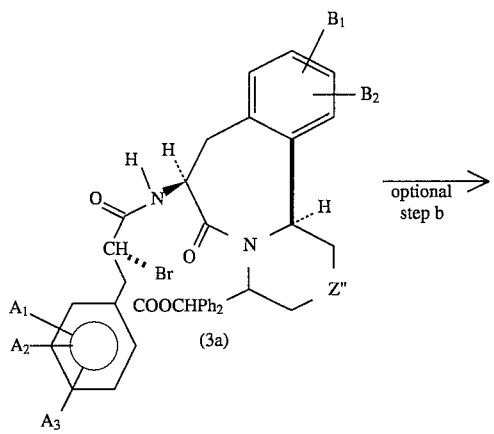

In step a, the appropriate (R)-bromotricyclic compound of structure (3a) can be prepared by reacting the appropriate amino tricyclic compound of structure (1) with

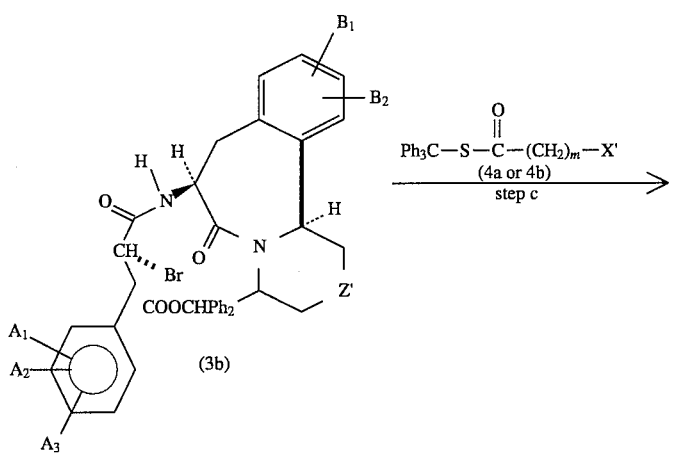

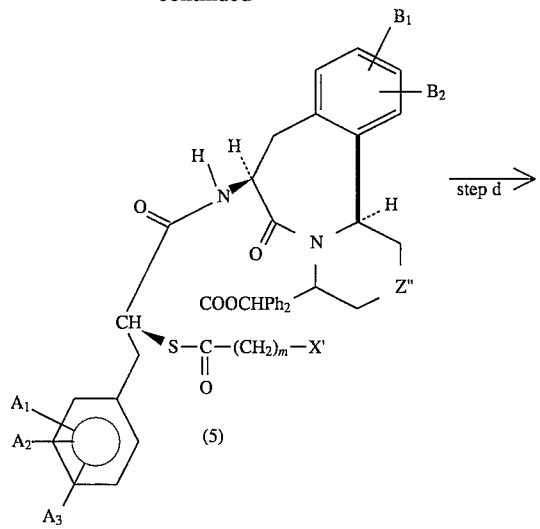

(5)

the appropriate (R)-bromo acid compound of structure (2). For example, the appropriate amino tricyclic compound of structure (1) can be reacted with the appropriate (R)-bromo

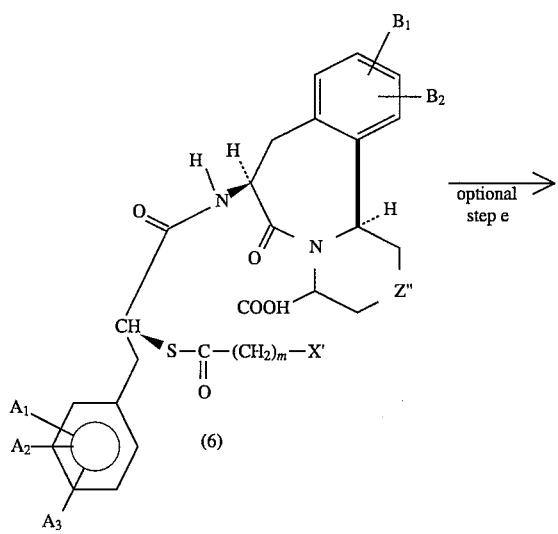

(6)

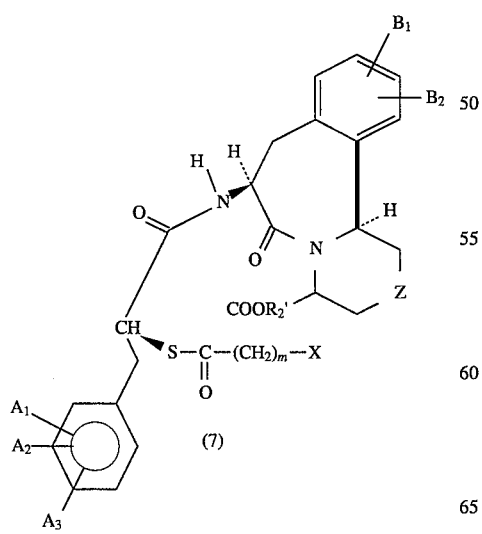

(7)

acid compound of structure (2) in the presence of a coupling reagent such as EEDQ (2-ethoxy-2-ethoxycarbonyl-1,2-dihydro-quinoline), DCC (1,3-dicyclohexylcarbodiimide), $Z'' = -CH_2-, -O-, -S-, -NH-$ or a bond
$Z' = -NR_3'-$ or $-NC(O)R_4-$
$R_2' =$ a $C_1-C_4$ alkyl, an $Ar-Y-$ group or
$-CH_2O-C(O)C(CH_3)_3$

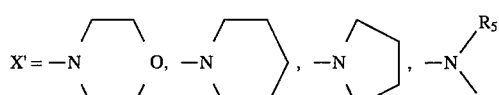

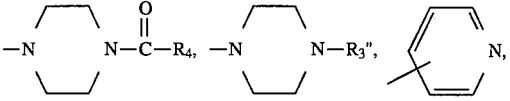

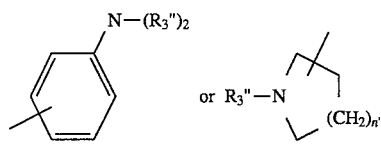

$R_3'' =$ BOC, $C_1-C_4$ alkyl or an $Ar-Y-$ group or diethylcyanophosphonate in a suitable aprotic solvent, such as methylene chloride to give the appropriate (R)-bromo-tricyclic compound of structure (3a).

In optional step b, the amino functionality of those (R)-bromotricyclic compounds of structure (3a) wherein Z is NH can be subjected to reductive alkylation with an appropriate aldehyde of structure $R_{3'(n-1)}CHO$ using sodium cyanoborohydride as is known in the art to give the corresponding (R)-bromotricyclic compound of structure (3b) wherein Z is $NR_3'$, wherein $R_3'$ is $C_1-C_4$ alkyl or an Ar—Y group.

Alternatively, the amino functionality of those (R)-bromotricyclic compounds of structure (3a) wherein Z is NH can be acylated using the appropriate acyl chloride of structure $R_4CO$—Cl or the appropriate anhydride of structure $(R_4CO)_2$—O as is well known in the art to give the corresponding (R)-bromotricyclic compound of structure (3b) wherein Z is N—C(O)R$_4$.

In step c, the appropriate (S)-aminoacetylthiotricyclic compound of structure (5) can be prepared by reacting the appropriate (R)-bromotricyclic compound of structure (3a or 3b) with the appropriate triphenylmethyl aminothiolacetate of structure (4a or 4b) under basic conditions such as sodium hydride, hydrogen sulfide in a suitable aprotic solvent such as dimethylformamide.

In step d, the diphenylmethyl ester functionality of the appropriate (S)-aminoacetylthiotricyclic compound of structure (5) can be removed using trifluoroacetic acid to give the corresponding (S)-aminoacetylthiotricyclic compound of structure (6).

For those (S)-aminoacetylthiotricyclic compounds of structure (5) wherein X' is

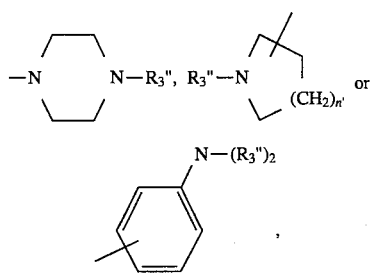

wherein R$_3$" is BOC, the BOC protecting group is also removed during the diphenylmethyl ester removal of step d.

In optional step e, the carboxylic acid functionality of the appropriate (S)-aminoacetylthiotricyclic compound of structure (6) can be reesterified by techniques well known in the art to give the corresponding (S)-aminoacetylthiotricyclic compound of structure (7).

In addition, the sulfide functionality of those (S)-aminothiotricyclic compounds of structure (6) wherein X is

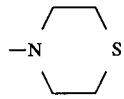

may be oxidized by techniques and procedures well known in the art, such as magnesium monoperoxyphthalic acid hexahydrate to give the (S)-aminothiotricyclic compounds of structure (6) wherein X is

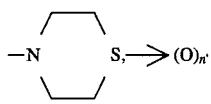

wherein n' is 1 or 2.

In addition, the nitro functionality of those (S)-aminothiotricylic compounds of structure (6) wherein A$_1$, A$_2$, or A$_3$ is a nitro group, can be reduced by techniques and procedures well known in the art, such as zinc/acetic acid, to give the (S)-aminothiotricylic compounds of structure (6) wherein A$_1$, A$_2$, or A$_3$ is an amino group.

Although Scheme A provides for the preparation of compounds of Formula (I) wherein the thioacetate functionality is of the (S)-configuration, the compounds of Formula I wherein the thioacetate functionality is of the (R)-configuration may be prepared by substituting the appropriate (R)-bromo compound of structure (2) with the corresponding (S)-bromo compound.

Scheme B provides a general synthetic scheme for preparing the triphenylmethyl aminothiolacetates of structures (4a and 4b ).

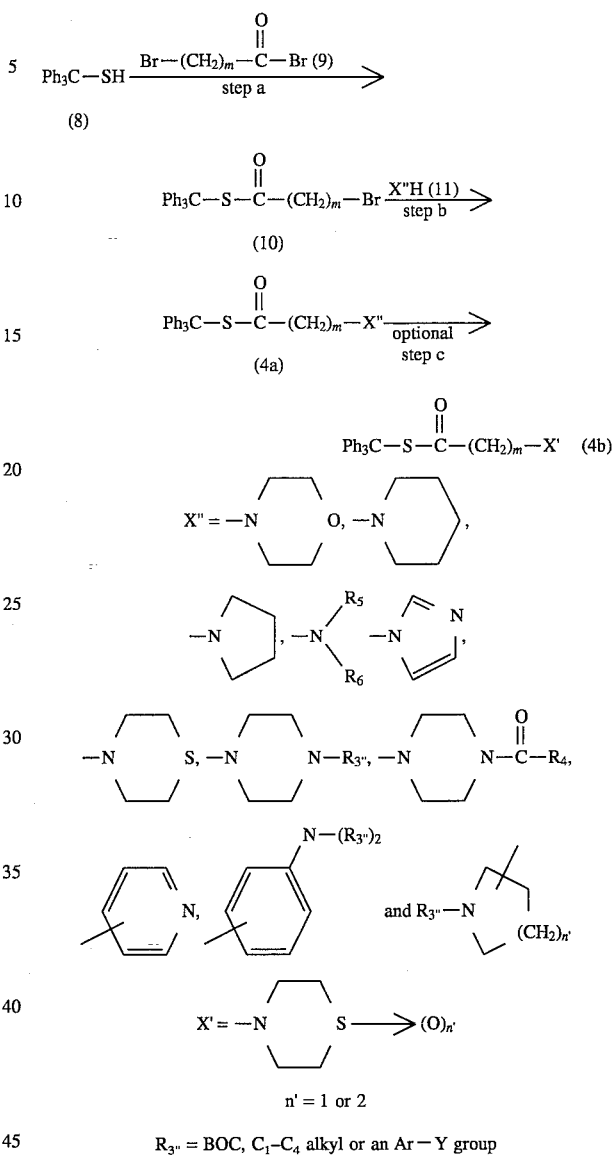

In step a, triphenylmethyl mercaptan (8) and bromoacetyl bromide (9) are reacted under basic conditions, such as pyridine, in an aprotic solvent such as methylene chloride to give triphenylmethyl bromothiolacetate of structure (10).

In step b, triphenylmethyl bromothiolacetate of structure (10) is reacted with the appropriate amino compound of structure (11) under basic conditions, such as pyridine, in an aprotic solvent such as methylene chloride to give the appropriate triphenylmethyl aminothiolacetate compound of structure (4a).

In optional step c, the sulfide functionality of those triphenylmethyl aminothiolacetate compounds of structure (4a) wherein X is represented by

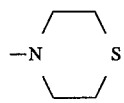

may by oxidized by techniques and procedures well known in the art, such as metachloroperbenzoic acid, to give the triphenylmethyl aminothiolacetate compounds of structure (4b) wherein X is represented by

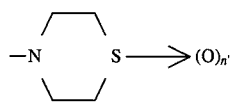

wherein n' is an 1 or 2.

Alternatively, the compounds of Formula (I) may be prepared as described in Scheme C. In Scheme C, all substituents are as previously defined unless otherwise indicated.

Scheme C

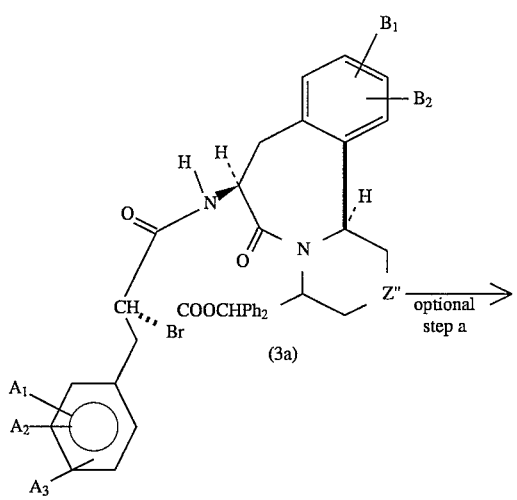

(3a)

-continued
Scheme C

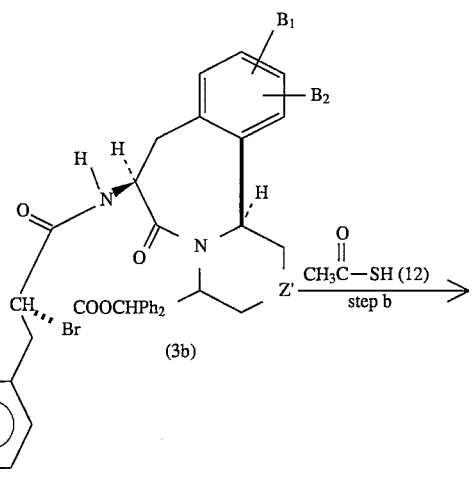

(3b)

In optional step a, the amino functionality of those (R)-bromotricyclic compounds of structure (3a) wherein Z is

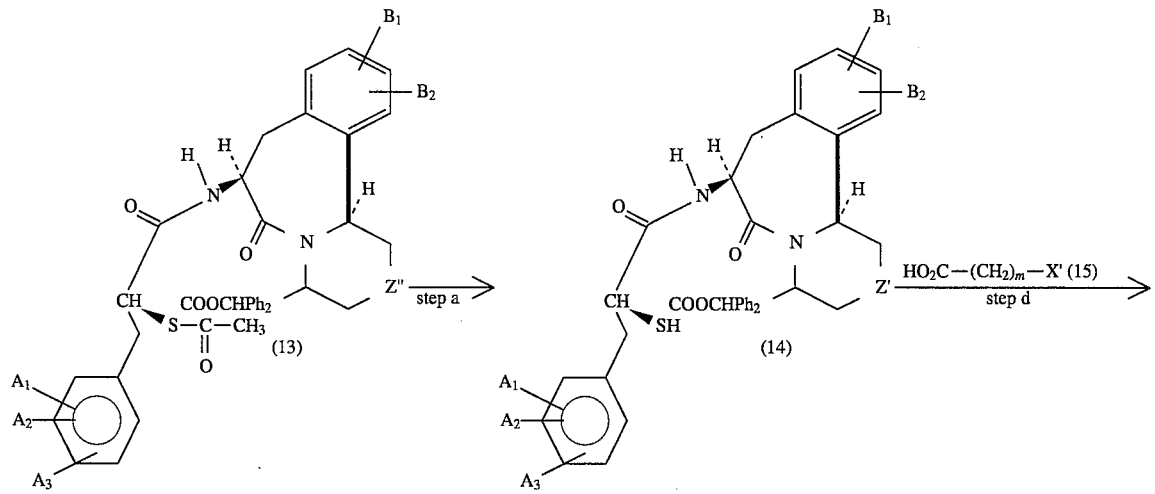

NH can be subjected to reductive alkylation with an appropriate aldehyde of structure $R_{3'(n-1)}$CHO as described previously in Scheme A, optional step b to give the

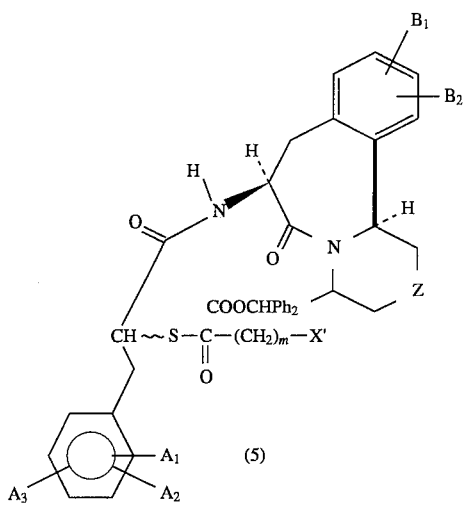

(5)

Z" = —CH$_2$—, —O—, —S—, —NH— or a bond
Z' = —NR$_3$'— or —NC(O)R$_4$—

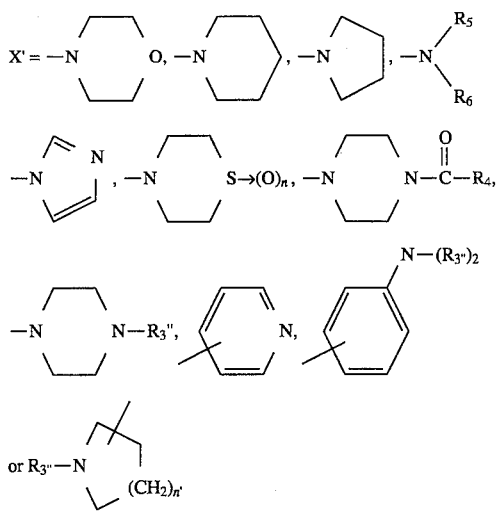

$R_3''$ = BOC, a $C_1$-$C_4$ alkyl or an Ar—Y— group corresponding (R)-bromotricyclic compound of structure (3b) wherein Z is NR$_3'$, wherein $R_3$' is $C_1$-$C_4$ alkyl or an Ar—Y group.

In step b, the appropriate (S)-acetylthiotricyclic compound of structure (13) can be prepared by reacting the appropriate (R)-bromotricyclic compound of structure (3a or 3b) with thiolacetic acid (12) in the presence of a base, such as cesium carbonate. The reactants are typically contacted in a suitable organic solvent such as dimethylformamide. The reactants are typically stirred together at room temperature for a period of time ranging from 1 to 8 hours. The resulting (S)-thioacetate of structure (13) is recovered from the reaction zone by extractive methods as is known in the art. It may be purified by chromatography.

In step c, the (S)-thioacetate functionality of the appropriate (S)-acetylthiotricyclic compound of structure (13) is hydrolyzed to the corresponding (S)-thiol compound of structure (14) with ammonia in a suitable protic solvent such as ethanol.

In step d, the thiol functionality of the appropriate (S)-thiol compound of structure (14) is coupled with the appropriate acid of structure (15) in the presence of a suitable coupling agent to give the appropriate (S)-aminoacetylthioltricyclic compound of structure (5). For example, the appropriate (S)-thiol compound of structure (14) can be reacted with the appropriate acid of structure (15) in the presence of a coupling reagent such as 2-fluoro-1-methylpyridinium p-toluenesulfate, EDCI (1-(3-dimethylaminopropyl)- 3-ethylcarbodiimide hydrochloride), carbonyldiimidazole, EEDQ (1-ethoxycarbonyl-2-ethoxy-1,2-dihydroquinoline, DCC (1,3-dicyclohexylcarbodiimide) or diethylcyanophosphonate in a suitable aprotic solvent such as methylene chloride to give the appropriate (S)-aminoacetyl-thiotricyclic compound of structure (5) which may be used as described previously in Scheme A, step d.

Amino tricyclic compounds of structure (1) wherein Z is —O— may be prepared as described in Scheme D. In Scheme D, all substituents unless otherwise indicated are as previously defined, Scheme D

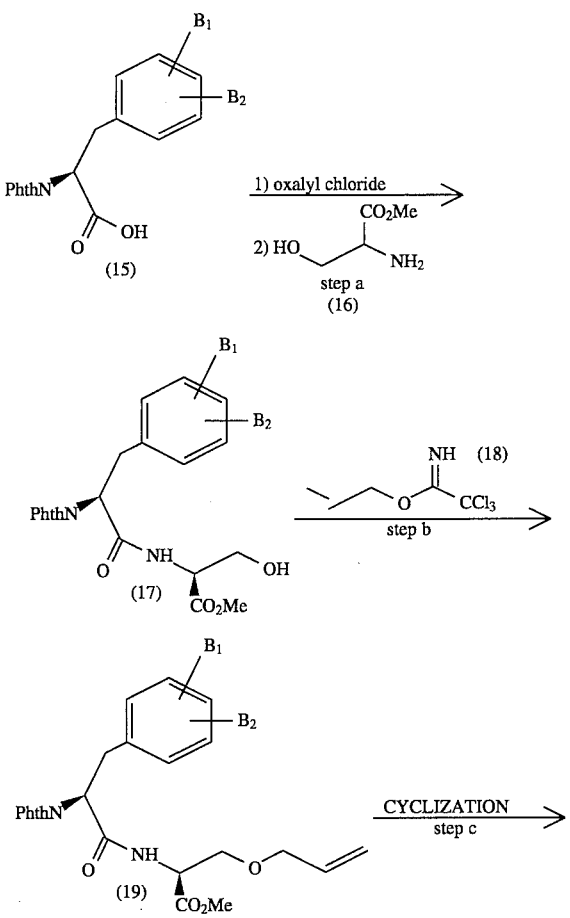

-continued
Scheme D

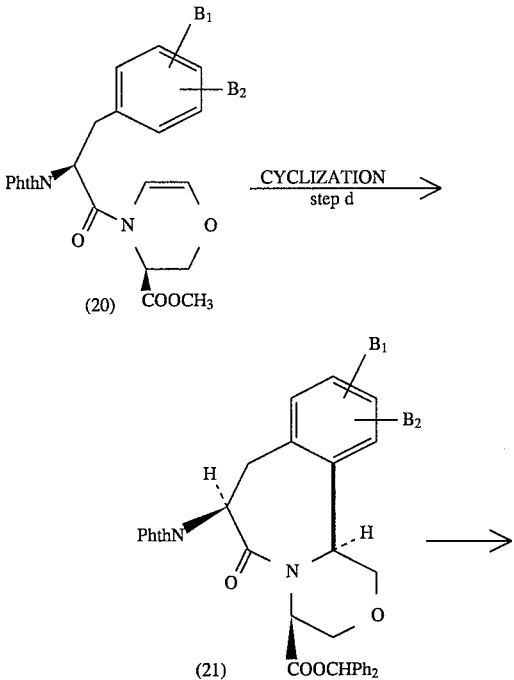

Scheme D provides a general synthetic procedure for preparing amino tricyclic compounds of structure (1) wherein Z is —O—.

In step a, the appropriate phthalimide blocked (S)-phenylalanine derivative of structure (15) is converted to the corresponding acid chloride, then reacted with the appropriate L-serine methyl ester of structure (16) to give the corresponding 1-oxo-3-phenylpropyl-L-serine methyl ester of structure (17).

For example, the appropriate phthalimide blocked (S-)phenylalanine derivative of structure (15) can be reacted with oxalyl chloride in a suitable aprotic solvent, such as methylene chloride. The resulting acid chloride can then be coupled with the appropriate L-serine methyl ester of structure (16) using N-methylmorpholine in a suitable aprotic solvent, such as dimethylformamide, to give the appropriate 1-oxo-3-phenylpropyl-L-serine methyl ester of structure (17).

In step b, the hydroxy functionality of the appropriate 1-oxo-3-phenylpropyl-L-serine methyl ester of structure (17) is allylated with the allyl imidate of structure (18) to give the corresponding 1-oxo-3-phenylpropyl-L-serine-O-allyl methyl ester of structure (19).

For example, appropriate 1-oxo-3-phenylpropyl-L-serine methyl ester of structure (17) is contacted with 2 molar equivalents of the allyl imidate of structure (18) and a molar equivalent of a suitable acid such as trifluoromethanesulfonic acid. The reactants are typically contacted in a suitable organic solvent mixture such as methylene chloride/cyclohexane. The reactants are typically stirred together at room temperature under an inert atmosphere for a period of time ranging from 2–24 hours. The 1-oxo-3-phenylpropyl-L-serine-O-allyl methyl ester of structure (19) is recovered from the reaction zone by extractive methods as is known in the art. It may be purified by silica gel chromatography or crystallization.

In step c, the appropriate 1-oxo-3-phenylpropyl-L-serine— O—allyl methyl ester of structure (19) is cyclized to give the corresponding (4S)-enamine of structure (20).

For example, the appropriate 1-oxo-3-phenylpropyl-L-serine— O—allyl methyl ester of structure (19) is first contacted with a molar excess of a mixture of ozone/oxygen. The reactants are typically contacted in a suitable organic solvent mixture such as methylene chloride/methanol. The reactants are typically stirred together for a period of time ranging from 5 minutes to 30 minutes or until a blue color persists and at a temperature range of from −78° C. to −40° C. The reaction is quenched with an excess of methylsulfide and the intermediate aldehyde compound recovered from the reaction zone by extractive methods as is known in the art.

The intermediate aldehyde compound is then contacted with trifluoroacetic acid in a suitable aprotic solvent such as methylene chloride to give the corresponding (4S)-enamine of structure (20).

In step d, the appropriate (4S)-enamine of structure (20) is cyclized to give the corresponding (4S)-tricyclic compound of structure (21) by an acid catalyzed Friedel-Crafts reaction. For example, the appropriate (4S)-enamine of structure (20) can be converted to the corresponding (4S)-tricyclic compound of structure (21) by treatment with a mixture of trifluoromethane sulfonic acid and trifluoroacetic anhydride in a suitable aprotic solvent, such as methylene chloride.

In step d, it may be necessary to reesterify the carboxy functionality due to the conditions of the work-up. For example, treatment of the crude product with bromodiphenylmethane in a suitable aprotic solvent, such as dimethylformamide along with a non-nucleophilic base, such as cesium carbonate, may be used to give the corresponding (4S)-diphenylmethyl ester.

In step e, the phthalimide protecting group of the appropriate (4S)-tricyclic compound of structure (21) is removed to give the corresponding amino tricyclic compound of structure (1) wherein X is —O—. For example, the phthalimide protecting group of the appropriate (4S)-tricyclic compound of structure (21) can be removed using hydrazine monohydrate in a suitable protic solvent such as methanol, to give the corresponding amino tricyclic compound of structure (1a).

Amino tricyclic compounds of structure (1) wherein Z is —NH— may be prepared as described in Scheme E. In Scheme E, all substituents unless otherwise indicated are as previously defined.

Scheme E

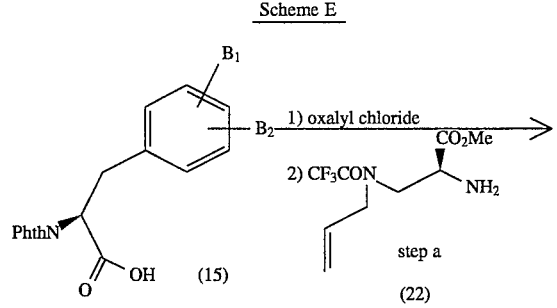

-continued
Scheme E

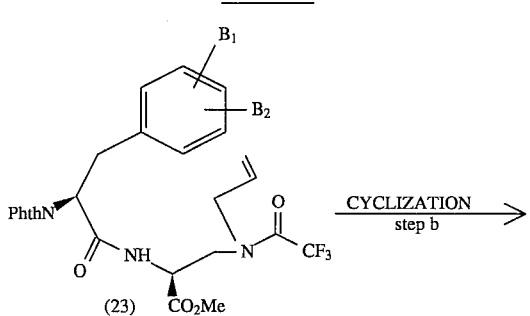
(23)

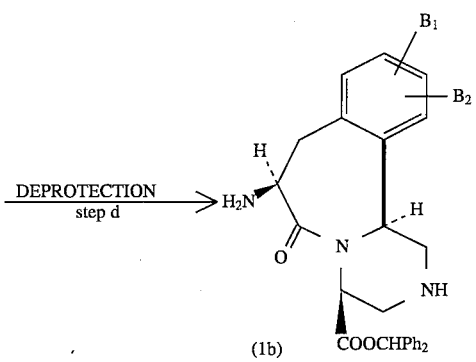
(1b)

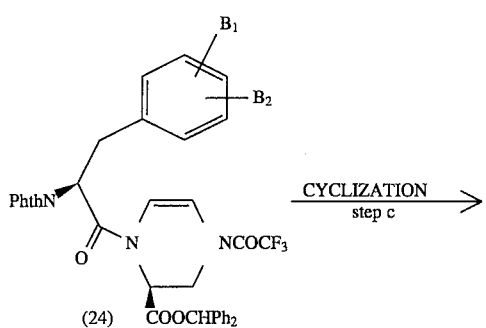
(24)

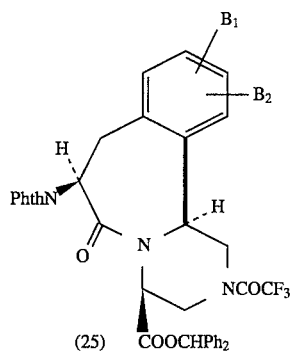
(25)

Scheme E provides an general synthetic procedure for preparing amino tricyclic compounds of structure (1) wherein Z is —NH—.

In step a, the appropriate phthalimide blocked (S)-phenylalanine derivative of structure (15) is converted to the corresponding acid chloride, then reacted with the appropriate 3-trifluoracetylamino-3-allyl-L-2-aminopropionic acid, methyl ester of structure (22) to give the corresponding 1-oxo-3-phenylpropyl-N-trifluoracetyl-N-allyl-L-amino acid, methyl ester of structure (23) as described previously in Scheme D, step a.

3-Trifluoracetylamino-3-allyl-L-2-aminopropionic acid, methyl ester of structure (22) may be prepared from $N^\alpha$-(benzyloxycarbonyl)-β -(amino)-L-alanine in a 4-step process.

$N^\alpha$-(Benzyloxycarbonyl)-β-(amino)-L-alanine is first converted to $N^\alpha$-(benzyloxycarbonyl)-β-(amino)-L-alanine, methyl ester by techniques and procedures well known and appreciated by one of ordinary skill in the art, such as methanol/sulfuric acid esterification.

The β-amino functionality of $N^\alpha$-(benzyloxycarbonyl)-β-(amino)-L-alanine, methyl ester is then allylated with allyl trichloroacetimidate to give the corresponding $N^\alpha$-(benzyloxycarbonyl)-β -(allylamino)-L-alanine, methyl ester using conditions described previously in Scheme D, step b.

The B-allylamino functionality of $N^\alpha$-(benzyloxycarbonyl)-β -(allylamino)-L-alanine, methyl ester is then acylated with trifluoroacetic anhydride as is known in the art to give $N^\alpha$-(benzyloxycarbonyl)-β-trifluoroacetyl-allylamino)-L-alanine, methyl ester.

The $N^\alpha$-(benzyloxycarbonyl) protecting group is then removed using boron tris(trifluoroacetate)/trifluoroacetic acid as is known in the art to give 3-trifluoracetylamino-3-allyl-L- 2-aminopropionic acid, methyl ester of structure (22).

In step b, the appropriate 1-oxo-3-phenylpropyl-N-trifluoracetyl-N-allyl-L-amino acid methyl ester of structure (23) is cyclized to give the corresponding enamine of structure (24) as described previously in Scheme D, step c.

In step c, the appropriate (4S)-enamine of structure (24) is cyclized to give the corresponding (4S)-tricyclic compound of structure (25) as described previously in Scheme D, step d.

In step d, the phthalimide protecting group of the appropriate (4S)-tricyclic compound of structure (25) is removed to give the corresponding amino tricyclic compound of structure (1b) as described in Scheme D, step e.

Amino tricyclic compounds of structure (1) wherein Z is —$CH_2$— may be prepared as described in Scheme F. In Scheme F, all substituents unless otherwise indicated are as previously defined.

Scheme F

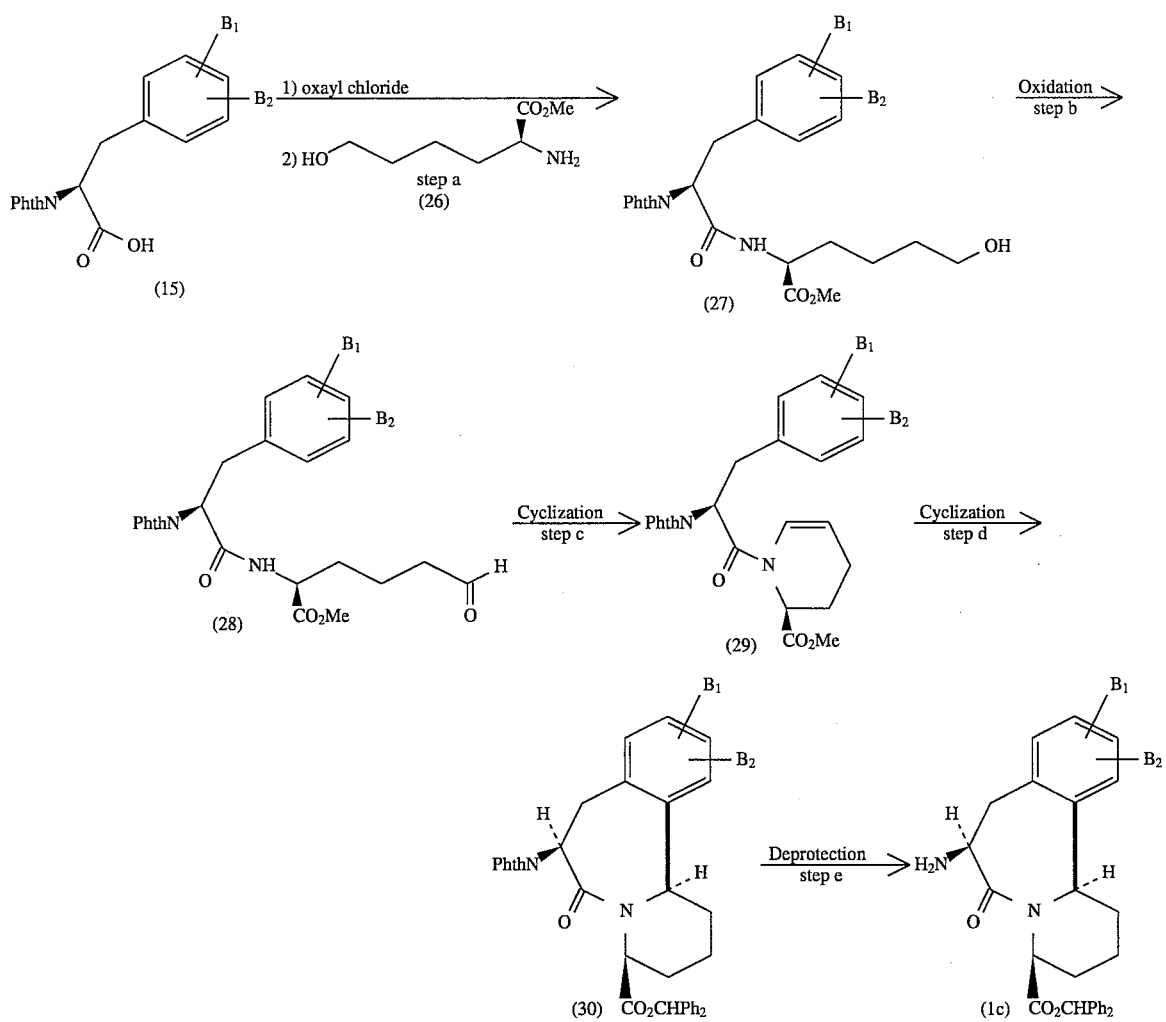

Scheme F provides a general synthetic procedure for preparing the amino tricyclic compounds of structure (1) wherein Z is —CH$_2$—.

In step a, the appropriate phthalimide blocked (S)-phenylalanine derivative of structure (15) can be converted to the corresponding acid chloride, then reacted with the appropriate amino acid methyl ester of structure (26) in a coupling reaction. For example, the appropriate phthalimide blocked (S)-phenylalanine derivative of structure (15) can be reacted with oxalyl chloride in a suitable aprotic solvent, such as methylene chloride. The resulting acid chloride can then be coupled with the appropriate amino acid methyl ester of structure (26) using N-methylmorpholine in a suitable aprotic solvent, such as dimethylformamide, to give the appropriate 1-oxo-3-phenylpropyl-amino acid methyl ester derivative of structure (27).

In step b, the hydroxymethylene functionality of the appropriate 1-oxo-3-phenylpropyl-amino acid methyl ester derivative of structure (27) can be oxidized to the appropriate aldehyde of structure (28) by oxidation techniques well known and appreciated in the art. For example, the hydroxymethylene functionality of the appropriate 1-oxo-3-phenylpropyl-amino acid methyl ester derivative of structure (27) can be oxidized to the appropriate aldehyde of structure (28) by means of a Swern oxidation using oxalyl chloride and dimethylsulfoxide in a suitable aprotic solvent, such as methylene chloride.

In step c, the appropriate aldehyde of structure (28) can be cyclized to the appropriate enamine of structure (29) by acid catalysis. For example, the appropriate aldehyde of structure (28) can be cyclized to the appropriate enamine of structure (29) by treatment with trifluroacetic acid in a suitable aprotic solvent, such as methylene chloride.

In step d, the appropriate enamine of structure (29) can be converted to the corresponding tricyclic compound of structure (30) by an acid catalyzed Friedel-Crafts reaction as described previously in Scheme D, step d.

In step e, the phthalimide protecting group of the appropriate tricyclic compound of structure (30) can be removed using techniques and procedures well known in the art. For example, the phthalimide protecting group of the appropriate tricyclic compound of structure (30) can be removed using hydrazine monohydrate in a suitable protic solvent such as methanol, to give the corresponding amino tricyclic compound of structure (1c).

Amino tricyclic compounds of structure (1) wherein Z is a bond may be prepared as described in Scheme G. In Scheme G, all substituents unless otherwise indicated are as previously defined.

Scheme G

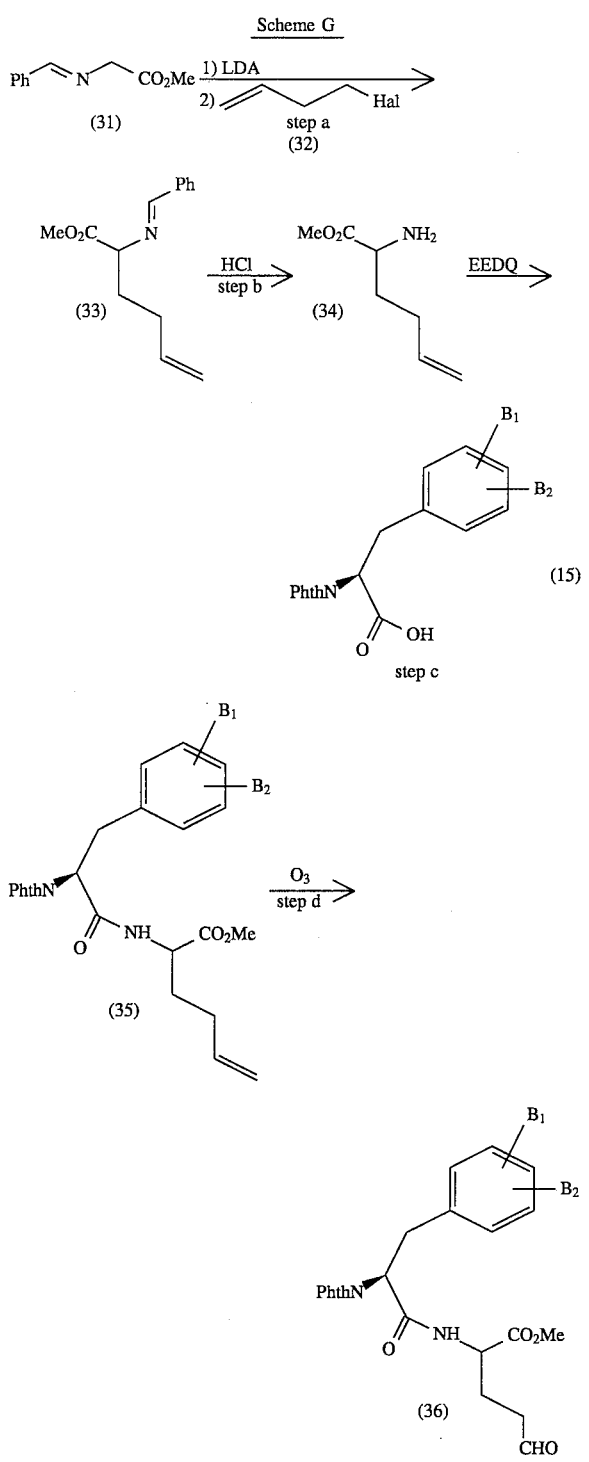

Scheme G provides a general synthetic procedure for preparing the amino tricyclic compounds of structure (1) wherein Z is a bond.

In step a, the N-(phenylmethylene)glycine methyl ester of structure (31) can be treated with one equivalent of a non-nucleophilic base, such as lithium diisopropylamide, in a suitable aprotic solvent, such as tetrahydrofuran, followed by addition of a 4-halobutene of structure (32) to give 2-(3-butenyl)-N-(phenylmethylene)glycine methyl ester of structure (33).

In step b, the N-(phenylmethylene) functionality of 2-(3-butenyl)-N-(phenylmethylene)glycine methyl ester of structure (33) can be hydrolyzed under acidic conditions, such as with hydrochloric acid in a suitable aprotic solvent, such as ethyl ether to give 2-(3-butenyl)-glycine methyl ester of structure (34).

In step c, the appropriate amide compound of structure (35) can be prepared by reacting the appropriate phthalimide protected (S)-phenylalanine compound of structure (15) with 2-(3-butenyl)-glycine methyl ester of structure (34) under coupling reaction conditions, such as with EEDQ, in a suitable aprotic solvent, such as methylene chloride.

In step d, the olefin functionality of the appropriate amide compound of structure (35) can be converted to the appropriate aldehyde compound of structure (36) under conditions of oxidative cleavage, such as treatment with ozone in a suitable solvent mixture, such as methylene chloride and methanol.

The amino tricyclic compounds of structure (1) wherein Z is a bond can be prepared from an appropriate aldehyde of structure (36) in a process as outlined previously in Scheme F, steps c–e.

Starting materials for use in Schemes A through G are readily available to one of ordinary skill in the art. For example, certain tricyclic compounds of structure (1) may be prepared as described in European Patent 0 249 223 (Dec. 16, 1987). $N^{\alpha}$-(benzyloxycarbonyl)-β-(amino)-L-alanine is described in *J. Am. Chem. Soc.* 107(24) 7105 1985, N-(phenylmethylene)glycine methyl ester is described in *J. Org. Chem.* 41, 3491 1976 and allyl trichloroacetimidate is described in *J. Chem. Soc. Perkin Trans.* 1(11) 2247 1985.

The following examples present typical syntheses as described in Schemes A through G. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "mp" refers to melting point; "°C." refers to degrees Celsius; "mm Hg" refers to millimeters of mercury; "µL" refers to microliter's; "µg" refers to micrograms; and "µM" refers to micromolar.

EXAMPLE 1

[4S-[4α-7α(R*), 12bβ]]-7-[(1-Oxo-2(S)-(4-morpholino)acetylthio-3-phenylpropyl)amino]-1,2,3,4,6,7,8,12b-octahydro-6-oxopyrido[2,1-a][2]benzazepine-4-carboxylic acid•trifluoroacetate salt—MDL 101,264

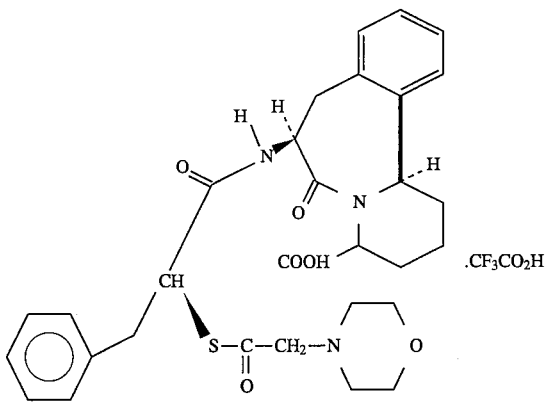

Method A

Scheme F, Step a:
(S)-N-[2-(1,3-Dihydro-1,3-dioxo-2H-isoindol-2-yl)-1-oxo-3-phenylpropyl]-6-hydroxy-(S)-norleucine, methyl ester Mix phthalic anhydride (1.82 kgs, 12.3 mole), (S)-phenylalanine (1.84 kgs, 11.1 moles) and anhydrous dimethylformamide (2.26 L). Stir at 115°–120° C. for 2 hours under a nitrogen atmosphere. Pour into rapidly stirring water (32.6 L) and cool overnight at 0° C. Filter, wash with cold water (2×2 L) and air dry. Dissolve in a mixture of 9A ethanol (8.05 L) and water (8.05 L) and heat at reflux temperature. Gravity filter, cool to ambient temperature and refrigerate overnight at about 0° C. Filter the crystallized product, wash with cold 50:50 9A ethanol/water (2×2 L) and air dry to yield 2.96 kg (90.3%) of N-phthaloyl-(S)-phenylalanine; mp 177°–179° C.

Mix N-phthaloyl-(S)-phenylalanine (50.2 g, 0.17 mole), methylene chloride (660 mL) and dimethylformamide (0.5 mL) under a nitrogen atmosphere. Add oxalyl chloride (17.7 mL, 0.2 mole) over about 5 minutes with stirring. Stir at ambient temperature for 3 hours and evaporate the solvent in vacuo to leave N-phthaloyl-(S)-phenylalanine, acid chloride as a solid (54.3 g, 101.9%).

Mix 6-hydroxy-(S)-norleucine, methyl ester, hydrochloride salt (33.5 g, 0.1 mole) and dimethylformamide (201 mL), cool to about 0° C. and place under a nitrogen atmosphere. Add by dropwise addition, N-methylmorpholine (51 mL, 0.46 mole) with cooling so that the pot temperature stays at 0°–5° C. Stir at 0°–5° C. for an additional 10 minutes, than add a solution of N-phthaloyl-(S)-phenylalanine, acid chloride (53.5 g, 0.17 mole) in methylene chloride (270 mL) over 30 minutes with cooling so that the temperature stays at 0°–5° C. Remove the cooling bath arid stir at room temperature for 18 hours.

Evaporate the methelene chloride in vacuo and dilute the remaining residue with ethyl acetate (800 mL). Extract the resulting mixture with water (800 mL), separate the organic layer and extract with 1N hydrochloric acid (270 mL), followed by water (3×500 mL). Dry the organic layer (MgSO$_4$), filter and evaporate in vacuo to yield crude product (76 g, 98%). Dissolve the crude product in hot toluene (223.5 mL), cool to room temperature, then cool overnight at about 0° C. Filter the crystallized product, wash with cold toluene and air dry to yield 56.6 g (76%) of the title compound; mp 128°–130° C.

Scheme F, Step b:
2-(1,3-Dihydro-1,3-dioxo-2H-isoindol-2-yl)-1-oxo-3-phenylpropyl-6-oxo-(S)-norleucine, methyl ester Mix oxalyl chloride (80 mL, 0.92 mole) and methylene chloride (2 L) and place under a nitrogen atmosphere. Cool below −50° C. and add a solution of dimethyl sulfoxide (65.4 mL, 0.92 mole) in methylene chloride (425 mL). Stir for 15 minutes and add a solution of (S)-N-[2-(1,3-dihydro-1,3-dioxo-2H-isoindol-2-yl)-1-oxo-3-phenylpropyl]-6-hydroxy-(S)-norleucine, methyl ester (200 g, 0.456 mole) in methylene chloride (800 mL) over about 45 minutes, keeping the pot temperature below −50° C. for 30 minutes. Add triethylamine (420 mL, 3.01 mole) over 30 minutes. Stir while warming to 0° C. over 1.25 hours. Transfer the reaction mixture to a 12-liter flask. Stir and cool while adding a solution of OXONE (potassium peroxymonosulfate) (566 g) in water (6.74 L) at such a rate that the pot temperature stays below 15° C. Stir for 5 minutes, separate the organic layer and extract the aqueous layer with methylene chloride (1 L). Combine the organic phases, dry (MgSO$_4$) and filter to yield the title compound as a solution.

Scheme F, Step c:
[S-(R*,R*)]-N-[2-(1,3-Dihydro-1,3-dioxo-2H-isoindol-2-yl)-1-oxo-3-phenylpropyl]-1,2,3,4-tetrahydro-2-pyridinecarboxylic acid, methyl ester Transfer the solution of 2-(1,3-dihydro-1,3-dioxo-2H-isoindol-2-yl)-1-oxo-3-phenylpropyl]-6-oxo-(S)-norleucine, methyl ester in methylene chloride (volume about 4.5 L) to a 12-liter flask and place under a nitrogen atmosphere. Stir and add trifluoroacetic acid (440 mL, 5.71 mole) in one portion. Stir the resulting mixture at room temperature for one hour, then rapidly cool to about 0° C. Add a solution of sodium hydroxide (240 g, 6.0 mole) in water (3.4 L) in a slow stream to the vigorously stirred mixture at such a rate that the pot temperature stays at about 0° C. Separate the organic phase and extract the aqueous phase with methylene chloride (1 L). Combine the organic phases and dry (MgSO$_4$). Filter and remove the solvent in vacuo to leave a residue (262 g, 137%).

Dissolve the above residue in diethyl ether (1 L) and wash with water (5×500 mL). Evaporate the organic phase in vacuo to leave a residue of 229 g. Dilute the residue with methylene chloride (200 mL) and purify by silica gel chromatography (methylene chloride) to yield a viscous residue of 225 g.

Dilute the above residue with diethyl ether (250 mL) and allow to stand at room temperature for 24 hours. Filter the solid, wash with diethyl ether, and air dry to yield 123.2 g; mp 140°–142.5° C. Recrystallize (methylene chloride (125 mL)/isopropanol (615 mL)) by boiling off the solvent until the pot temperature reaches 75° C. and allowing the resulting sample to stand at room temperature for 24 hours. Filter, wash with cold isopropanol and air dry to yield 101.5 g of the title compound; mp 144°–146° C.

Evaporate the filtrate from the 101.5 g in vacuo to yield 24 g. Recrystallize (isopropanol) to yield an additional 3.5 g of the title compound.

Evaporate the filtrate from the 123.2 g in vacuo to leave 62 g of oil. Purify by silica gel chromatography (25% ethyl acetate/75% hexane), collecting 21–500 mL fractions. Combine fractions 9–20 and evaporate in vacuo to yield 35 g of a viscous oil. Recrystallize three times (isopropanol/5 mL/g) to yield an additional 11.9 g of the title compound; mp 142.5°–144.5° C. Total yield of useful material: 116.9 g (61.3%).

Scheme F, Step d: [4S-[4α, 7α(R*), 12bβ]]-7-[(1,3-Dihydro-1,3-dioxo-2H-isoindol-2-yl)]-1,2,3,4,6,7,8,12b-octahydro-6-oxopyrido[2,1-a][2]-benzazepine-4-carboxylic acid, diphenylmethyl ester Mix trifluoromethanesulfonic acid (500 g, 3.33 mole) and trifluoroacetic anhydride (74.8 mL, 0.53 mole) and place under a nitrogen atmosphere. Stir and add a solution of [S-(R*,R*)]-N-[2-(1,3-dihydro-1,3-dioxo-2H-isoindol-2-yl)-1-oxo-3-phenylpropyl]-1,2,3,4-tetrahydro-2-pyridinecarboxylic acid, methyl ester (200 g, 0.48 mole) in methylene chloride (1 L) with cooling at such a rate as to keep the pot temperature below 35° C. Stir at ambient temperature for 2 days. Pour into vigorously stirring ice water (5 L) and stir for 30 minutes. Extract with ethyl acetate (3×1 L), combine the organic phases and wash with water (3×500 mL). Evaporate in vacuo to a residue. Dissolve the residue in ethyl acetate (4 L) and extract with ¼ saturated potassium hydrogen carbonate (1 L), then ⅓ saturated potassium hydrogen carbonate (7×1 L). Combine the aqueous extracts and dilute with ethyl acetate (2 L). Stir the resulting mixture and cool to 5°–10° C. Adjust to pH 2 using concentrated hydrochloric acid (about 750 mL).

Separate the organic phase and extract the aqueous phase with ethyl acetate (3×1 L). Combine the ethyl acetate extracts, wash with water (3×1 L), then saturated sodium chloride (0.8 L), and dry (MgSO₄). Filter and wash with ethyl acetate (3×200 mL). Evaporate in vacuo to leave (188.3 g, 101.5%) [4S-[4α, 7α(R*), 12bβ]]-7-[(1,3-dihydro-1,3-dioxo-2H-isoindol-2-yl)]-1,2,3,4,6,7,8,12b-octahydro-6-oxopyrido[2,1-a][2]benzazepine-4-carboxylic acid as a colorless foam.

Dissolve [4S-[4α, 7α(R*), 12bβ]]-7-[(1,3-dihydro-1,3-dioxo-2H-isoindol-2-yl)]-1,2,3,4,6,7,8,12b-octahydro-6-oxopyrido[2,1-a][2]benzazepine-4-carboxylic acid (113.9 g, 0.28 mole) in methylene chloride (1.2 L) and dry over anhydrous MgSO₄ (60 g). Filter and wash with methylene chloride (3×200 mL). Evaporate in vacuo to a residue. Dissolve the residue in anhydrous dimethylformamide (860 mL) and place under a nitrogen atmosphere. Add cesium carbonate (98.9 g, 0.3 mole) in one portion. Stir for 45 minutes at ambient temperature. Add bromodiphenylmethane (164.8 g, 0.67 mole). Stir the resulting mixture at ambient temperature for 18 hours. Quench the reaction with ethyl acetate (2.464 L) and water (630 mL). Separate the organic phase and wash with water (7×625 mL), ¼ saturated potassium hydrogen carbonate (625 mL), water (625 mL), and saturated sodium chloride (625 mL). Dry (MgSO₄), filter and evaporate in vacuo to yield 214.4 g of an oil. Extract the combined aqueous washings with ethyl acetate (3×500 mL), wash with water (4×300 mL) and dry (MgSO₄). Filter and evaporate in vacuo to yield an additional 20.2 g of an oil.

Dissolve the crude product (234.6 g) in methylene chloride (200 mL) and filter through a plug of silica gel (213 g), eluting with methylene chloride (2 L). Boil off the solvent and replace with hexane (3 L), with the pot temperature reaching a maximum of 65° C. Cool to ambient temperature, decant off the precipitated oil and crystallize (9A ethanol) to yield 96.6 g (60%) of the title compound; mp 153°–155° C.

Scheme F, Step e: [4S-[4α, 7α(R*), 12bβ]]-7-(Amino)-1,2,3,4,6,7,8,12b-octahydro-6-oxopyrido[2,1-a][2]benzazepine-4-carboxylic acid, diphenylmethyl ester Mix [4S-[4α, 7α(R*), 12bβ]]-7-[(1,3-dihydro-1,3-dioxo-2H-isoindol-2-yl)]-1,2,3,4,6,7,8,12b-octahydro-6-oxopyrido[2,1-a][2]benzazepine-4-carboxylic acid, diphenylmethyl ester (170.9 g, 0.3 mole), hydrazine monohydrate (34.4 g, 0.68 mole) and methanol (3.4 L) under a nitrogen atmosphere. Heat at reflux for 5 hours. Cool to ambient temperature and filter to remove phthaloyl hydrazide. Evaporate the filtrate in vacuo to a residue and slurry in chloroform (600 mL). Remove insoluble phthaloyl hydrazide by filtration and wash with chloroform (4×210 mL). Wash the filtrate with water (4×429 mL), dry (MgSO₄), and filter. Evaporate the filtrate to a solid residue of the title compound weighing 142 g (107.7%).

Scheme B, steps a and b: Triphenylmethyl 4-morpholinethiolacetate

Dissolve triphenylmethyl mercaptan (27.6 g, 100 mmol) and pyridine (10 mL) in methylene chloride (120 mL). Cool to −50° C., add bromoacetyl bromide (8.7 mL, 100 mmol) and stir for 20 minutes while warming to room temperature. Add morpholine (27 mL, 300 mmol) and cool as necessary to maintain ambient temperature. Stir for 3 hours, filter and pour into methylene chloride. Wash with water and brine and dry (MgSO₄). Evaporate the solvent in vacuo and purify by chromatography and crystallization to give the title compound as a crystalline solid.

Scheme A, step a: [4S-[4α-7α(R*), 12bβ]]-7-[(1-Oxo-2(R)-bromo-3-phenylpropyl)amino]-1,2,3,4,6,7,8,12b-octahydro-6-oxopyrido-[2,1-a][2]benzazepine-4-carboxylic acid, diphenylmethyl ester Mix [4S-[4α-7α(R*), 12bβ]]-7-amino-1,2,3,4,6,7,8,12b-octahydro-6-oxopyrido[2,1-a][2]benzazepine-4-carboxylic acid, diphenylmethyl ester (10 mmol), (R)-3-phenyl-2-bromopropionic acid (2.75 g, 12 mmol), 2-ethoxy-2-ethoxycarbonyl-1,2-dihydro-quinoline (EEDQ) (3.0 g, 12 mmol) and methylene chloride (25 mL). Stir at room temperature for 4 hours, dilute with methylene chloride, wash with 10% hydrochloric acid, saturated sodium hydrogen carbonate and brine. Dry (MgSO₄) and evaporate the solvent in vacuo. Purify by recrystallization (25% ethyl acetate/hexane) to give the title compound as a white solid (6.1 g, 94%); mp 167°–168° C.

Scheme A, step c: [4S-[4α-7α(R*), 12bβ]]-7-[(1-Oxo-2(S)-(4-morpholino)-acetylthio-3-phenylpropyl)amino]-1,2,3,4,6,7,8,12b-octahydro-6-oxopyrido[2,1-a][2]benzazepine-4-carboxylic acid, diphenylmethyl ester Suspend sodium hydride (175 mg of a 60% suspension, 4.0 mmol) in anhydrous dimethylformamide (4 mL) and place under a nitrogen atmosphere. Bubble hydrogen sulfide gas into the suspension until solution occurs. Add triphenylmethyl morpholinethiolacetate (1.61 g, 4.0 mmol) and heat gently for 1.5 hours while bubbling nitrogen through the solution to facilitate removal of excess hydrogen sulfide gas. Add [4S-[4α-7α(R*), 12bβ]]-7-[(1-oxo-2(R)-bromo-3-phenylpropyl)amino]-1,2,3,4,6,7,8,12b-octahydro-6oxopyrido[2,1-a][2]benzazepine-4-carboxylic acid, diphenylmethyl ester (1.3 g, 2.0 mmol) and stir for 2 hours. Pour into water, extract in to ethyl acetate, wash with brine and dry (MgSO₄). Evaporate the solvent in vacuo and purify by chromatography (30→60% ethyl acetate/hexane) to give the title compound as a colorless foam (1.3 g, 89%).

Scheme A, step d: [4S-[4α-7α(R*), 12bβ]]-7-[(1-Oxo-2(S)-(4-morpholino)-acetylthio-3,phenylpropyl)amino]-1,2,3,4,6,7,8,12b-octahydro-6-oxopyrido[2,1-a][2]benzazepine-4-carboxylic acid•trifluroracetate—MDL 101,264

Mix [4S-[4α-7α(R*), 12bβ]]-7-[(1-oxo-2(S)-(4-morpholino)-acetylthio-3-phenylpropyl)amino]-1,2,3,4,6,7,8,12b-octahydro-6-oxopyrido[2,1-a][2]benzazepine-4-carboxylic acid, diphenylmethyl ester (1.46 g, 2.0 mmol), anisole (0.5 mL) and methylene chloride (6 mL). Place under a nitrogen atmosphere and cool to −50° C. Add trifluroracetic acid (3.0 mL) over 1 minutes and allow to warm to room temperature over 2 hours while stirring. Evaporate the solvent in vacuo, triturate with hexane and methylene chloride and dry under high vacuum to give the title compound as a light tan foam (1.47 g).

Method B

Scheme C, step b: [4S-4α-7α(R*), 12bβ]]-7-[(1-Oxo-2(S)-acetylthio-3-phenylpropyl)amino]-1,2,3,4,6,7,8,12b-octahydro-6-oxopyrido[2,1-a][2]benzazepine-4-carboxylic acid, diphenylmethyl ester Add thiolacetic acid (1.1 mL, 15.4 mmol) to a solution of cesium carbonate (2.51 g, 7.7 mmol) in methanol (30 mL). Stir the reaction mixture at room temperature for 30 minutes, evaporate the solvent in vacuo and dry in vacuo for 2 hours. Dissolve the orange solid residue in dimethylformamide (40 mL) and slowly add to a solution of [4S-[4α-7α(R*), 12bβ]]-7-[(1-oxo-2(R)-bromo-3-phenylpropyl)amino]-1,2,3,4,6,7,8,12b-octahydro-6-oxopyrido[2,1-a][2]benzazepine-4-carboxylic acid, diphenylmethyl ester (5.0 g. 7.7 mmol) in dimethylformamide (60 mL). Stir the reaction mixture at room temperature for 1 hour, dilute with ethyl acetate, wash with water and brine, dry over $MgSO_4$ and evaporate the solvent in vacuo. Purify by silica gel chromatography (hexane:ethyl acetate/6:4) to give the title compound as a foam (3.74 g, 75%).

$^1$H NMR ($CDCl_3$) δ7.46 (d, 1, J=9 Hz), 7.18–7.37 (m, 12), 6.89–7.13 (m, 6), 6.62 (m, 1), 6.26 (s, 1), 5.56 (m, 1), 5.37 (m, 2), 4.39 (t, 1, J=7.5 Hz), 3.28–3.43 (m, 2), 3.06 (dd, 1, J=7.5, 15 Hz), 2.58–2.27 (m, 3), 2.40 (s, 3), 2.02–1.86 (m, 1), 1.62–1.84 (m, 3).

Scheme C, step c: [4S-[4α-7α(R*), 12bβ]]-7-[(1-Oxo-2(S)-thio-3-phenylpropyl)amino]-1,2,3,4,6,7,8,12b-octahyro-6-oxopyrido[2,1-a][2]benzazepine-4-carboxylic acids diphenylmethyl ester Suspend [4S-[4α-7α(R*), 12bβ]]-7-[(1-Oxo-2(S)-acetylthio-3-phenylpropyl)amino]-1,2,3,4,6,7,8,12b-octahydro-6-oxopyrido[2,1-a][2]benzazepine-4-carboxylic acid, diphenylmethyl ester (3.85 g, 5.95 mmol) in absolute ethanol (100 mL) and add saturated ethanolic ammonia (100 mL). Stir the reaction mixture at room temperature for 1.5 hours, evaporate the solvent and dissolve the residue in methylene chloride. Wash with water and brine, dry ($MgSO_4$) and evaporate the solvent in vacuo to give the title compound as a glassy solid (3.38 g, 94%).

IR (KBr) 3429, 3393, 3061, 3030, 2943, 1734, 1649, 1495, 1439, 1283, 1250, 747, 700 $cm^{-1}$; $^1$H NMR ($CDCl_3$) δ7.61 (d, 1, J=6.6 Hz), 7.14–7.37 (m, 12), 6.88–7.12 (m, 6), 6.63 (m, 1), 6.28 (s, 1), 5.58 (m, 1), 5.29–5.44 (m, 2), 3.65 (q, 1, J=8.1 Hz), 3.38 (dd, 1, J=6, 17.4 Hz), 3.05 (dd, 1, J=5.4, 15 Hz), 2.54 (dd, 1, J=12, 17.4 Hz), 2.34–2.47 (m, 2), 2.07 (d, 1, J=8.7 Hz), 1.85–2.01 (m, 1), 1.61–1.85 (m, 3); $^{13}$C NMR ($CDCl_3$) δ171.74, 170.94, 169.61, 139.89, 138.97, 137,47, 136.50, 135.29, 130.81, 129.39, 128.39, 128.27, 128.19, 127.79, 127.71, 127.39, 126.95, 126.91, 126.80, 125.42, 124.66, 78.29, 51.14, 51.03, 48.51, 44.57, 41.34, 36.45, 24.92, 17.10; MS (FAB) m/z 605 [$M^+$+H], 393, 167.

Anal. Calcd for $C_{37}H_{36}N_2O_4S \cdot 0.5H_2O$: C, 72,40; H, 6.08; N, 4.56; Found: C, 72.49; H, 6.11; N, 4.40.

Scheme C, step d: [4S-[4α-7α(R*), 12bβ]]-7-[(1-Oxo-2(S)-(4-morpholino)-acetylthio-3-phenylpropyl)amino)-amino]-1,2,3,4,6,7,8,12b-octahydro-6-oxopyrido[2,1-a]-[2]benzazepine-4-carboxylic acid, diphenylmethyl ester Dissolve t-butyl bromoacetate (1 eq) in tetrahydrofuran and add morpholine (2.2 eq) via syringe. Stir the reaction mixture at room temperature for 2 hours, filter and wash the filter cake with ethyl acetate. Combine the organic filtrates and wash with saturated sodium bicarbonate (2×), water (2×) and brine. Dry ($Na_2SO_4$), filter and evaporate the solvent in vacuo. Take up the oily residue in ethyl acetate, cool in ice and bubble hydrogen chloride gas into the solution. Stir at room temperature overnight, cool and filter to give morpholinoacetic acid (85%); mp 169°–170° C.; $^1$H NMR ($D_2O$) δ3.75–4.29 (br m, 6), 3.59 (br s, 2), 3.28 (br s, 2).

Suspend morpholinoacetic acid (4.9 mmol) in degassed dimethylformamide (40 mL) and add carbonyldiimidazole (0.477 g, 2.94 mmol). Stir the reaction mixture at room temperature for 1.5 hours. Add a solution of [4S-[4α-7α(R*), 12bβ]]-7-[(1-Oxo-2(S)-thio-3-phenylpropyl)amino]-1,2,3,4,6,7,8,12b-octahydro-6-oxopyrido[2,1-a][2]benzazepine-4-carboxylic acid, diphenylmethyl ester (2.45 mmol) in degassed tetrahydrofuran and stir at room temperature overnight. Dilute with ethyl acetate, wash with water (2×) and brine, dry ($MgSO_4$) and evaporate the solvent in vacuo. Purify by silica gel chromatography (hexane:ethyl acetate/1:1 to 3:7) to give the title compound (86%).

$^1$H NMR ($CDCl_3$) δ7.44, (d, 1, J=9 Hz), 7.15–7.35 (m, 12), 6.91–7.12 (m, 6), 6.63 (m, 1), 6.28 (s, 1), 5.57 (m, 1), 5.30–5.43 (m, 2), 4.30 (t, 1, J=7.5 Hz), 3.74 (t, 4, J=4.5 Hz), 3.17–3.46 (m, 4), 2.33–2.68 (m, 7), 1.52–2.04 (m, 4).

Scheme A, step d: [4S-[4α-7α(R*), 12bβ]]-7-[(1-Oxo-2(S)-(4-morpholino)-acetylthio-3-phenylpropl)amino]-1,2,3,4,6,7,8,12b-octahydro-6-oxopyrido[2,1-a][2]benzazepine-4-carboxylic acid•trifluoroacetate salt Dissolve [4S-[4α-7α(R*), 12bβ]]-7-[(1-Oxo-2(S)-(4-morpholino)-acetylthio-3-phenylpropyl)amino]1,2,3,4,6,7,8,12b-octahydro-6-oxopyrido[2,1-a][2]benzazepine-4-carboxylic acid, diphenylmethyl ester (1.86 mmol) and anisole (1.5 mL, excess) in methylene chloride (20 mL), cool to −50° C. and add trifluoroacetic acid (3 mL). Stir the reaction mixture at −50° C. for 2.5 hours, evaporate the solvent in vacuo and triturate with hexane (4×). Take up the residue in a minimal amount of methylene chloride and precipitate from hexane (3×) to give the title compound (68%).

$^1$H NMR ($CDCl_3$) δ7.66 (d, 1, J=7.5 Hz), 6.97–7.39 (m, 9), 5.60–5.74 (m, 1), 5.39–5.48 (m, 1), 5.03–5.12 (m, 1), 4.54 (dd, 1, J=7.5, 9 Hz), 4.00 (s, 2), 3.88 (t, 4, J=3 Hz), 2.99–3.51 (m, 7), 2.85 (dd, 1, J=12, 18 Hz), 2.43–2.57 (m, 1), 2.26–2.39 (m, 1), 1.66–2.06 (m, 4); $^{19}$F NMR ($CDCl_3$) δ−74.0; MS (CI, 70 eV) m/z 566 [$M^+$+H].

EXAMPLE 2

[4S-[4α-7α(R*), 12bβ]]-7-[(1-Oxo-2(S)-(4-morpholino)-acetylthio-3-phenylpropyl)amino]-1,2,3,4,6,7,8,12b-octahydro-6-oxopyrido[2,1-a][2]benzazepine-4-carboxylic acid•dihydrochloride salt

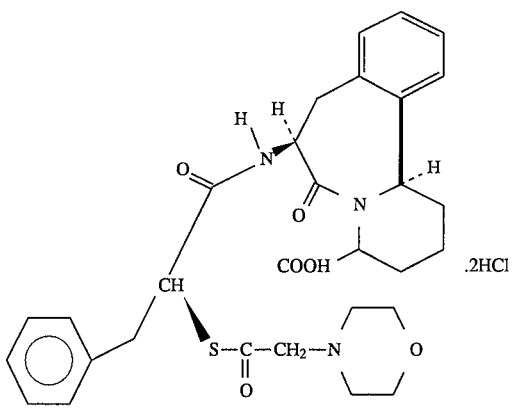

Slurry [4S-[4α-7α(R*), 12bβ]]-7-[(1-oxo-2(S)-(4-morpholino)-acetylthio-3-phenylpropyl)amino]-1,2,3,4,6,7,8,12b-octahydro-6-oxopyrido[2,1-a][2]benzazepine-4-carboxylic acid•trifluroacetate salt (900 mg) in diethyl ether (50 mL). Pass HCl gas through the slurry and stir for 30 minutes. Evaporate the solvent in vacuo and take the residue up in pentane. Filter to give the title compound as a white powder (695 mg).

EXAMPLE 3

[4S-[4α-7α(R*), 12bβ]]-7-[(1-Oxo-2(S)-(4-morpholino)-acetylthio-3-phenylpropyl)amino]-1,2,3,4,6,7,8,12b-octahydro-6-oxoryrido[2,1-a]-[2]benzazepine-4-carboxylic acid

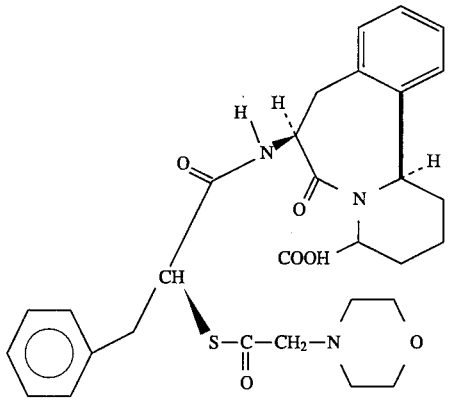

Suspend [4S-[4α-7α(R*), 12bβ]]-7-[( 1-oxo-2(S)-(4-morpholino)-acetylthio-3-phenylpropyl)amino]1,2,3,4,6,7,8,12b-octahydro-6-oxopyrido[2,1a][2]benzazepine-4-carboxylic acid•dihydrochloride salt (5.01 g, 8.86 mmol) in 1M sodium hydrogen carbonate (50 mL) and add methylene chloride (200 mL). Stir at room temperature for 1 hour, separate the organic layer and extract the aqueous layer with methylene chloride (2×100 mL). Combine the extraces, wash with water (50 mL ) and brine (50 mL), evaporate the solvent in vacuo and dry in vacuo to give the title compound as a white solid (4.23 g, 86%).

EXAMPLE 4

[4S-[4α-7α(R*), 12bβ[[-7-[(1-Oxo-2(S)-(4-morpholino)-acetylthio-3-phenylppopyl)amino]-1,2,3,4,6,7,8,12b-octahydro-6-oxopyrido-[2,1-a][2]benzazepine-4-carboxylic acid•maleate salt

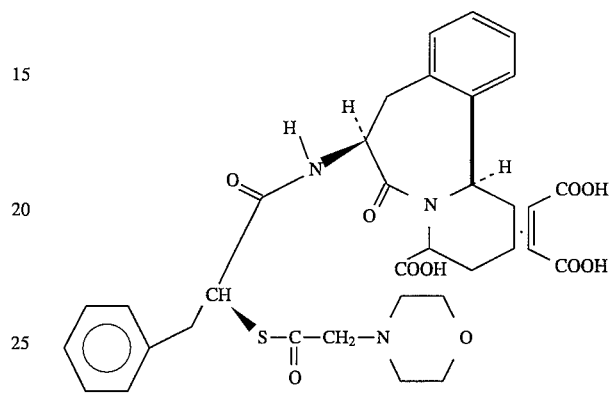

Dissolve [4S-[4α-7α(R*), 12bβ]]-7-[(1-oxo-2(S)-(4-morpholino)-acetylthio-3-phenylpropyl)amino]-1,2,3,4,6,7,8,12b-octahydro-6-oxopyrido[2,1-a][2]benzazepine-4-carboxylic acid (1.87 g, 3.31 mmol) in tetrahydrofuran (8 mL). Add a solution of maleic acid (392 mg, 3.38 mmol) in tetrahydrofuran (2 mL). Reduce the volume of solvent to 9 mL with a stream of argon and keep at room temperature for 15 minutes. Cool at –25° C. overnight and filter the crystalline solid under nitrogen. Wash with cold (–25° C.) tetrahydrofuran, dry briefly under argon and vacuum dry under a nitrogen atmosphere at room temperature for 120 hours to give the title compound as a crystalline solid (1.64 g).

EXAMPLE 5

[4S-[4α-7α(R*), 12bβ]]7-[(1Oxo-2(S)-4-morpholino)-acethylthio-3-phenylpropyl)amino]-1,2,3,4,6,7,8,12b-hexahydro-6-oxo-1H-[1,4]-oxazino-[3,4-a][2]benzazepine-4-carboxylic acid•trifluoroacetate

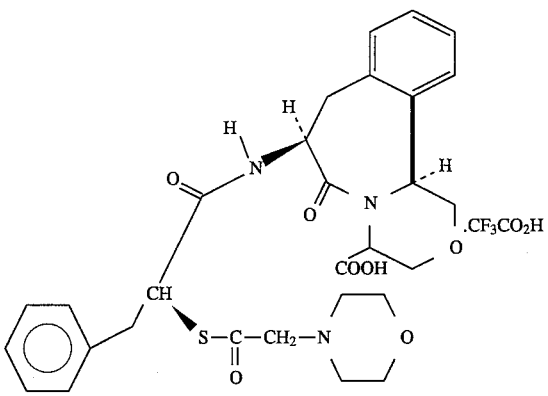

Scheme D, step a:
N-[2-(1,3-Dihydro-1,3-dioxo-2H-isoindol-2-yl)-1-oxo-3-phenylpropyl]-L-seriner methyl ester Slurry N-phthaloyl--(S)-phenylalanine (90 g, 0.3 mol) in methylene chloride (450 mL) and add, by dropwise addition, oxalyl chloride (54 mL, 0.62 mol). Place under a dry atmosphere (CaSO$_4$ tube) and treat with dimethylformamide (10μL). Stir for 5 hours, filter and concentrate in vacuo to give N-phthaloy-(S)-phenylalanine, acid chloride as an off white amorphous solid.

Dissolve serine methyl ester hydrochloride (56 g, 0.36 mol) in tetrahydrofuran (300 mL) then cool to 0° C. and add 4-methylmorpholine (88 mL, 0.8 mol). Add, by dropwise addition, a solution of the N-phthaloyl-(S)-phenylalanine, acid chloride in tetrahydrofuran (200 mL). Allow to warm to room temperature and stir for 3 hours. Filter and concentrate the filtrate in vacuo. Dissolve the residue in ethyl acetate and separate the organic phase. Wash with water then saturated sodium chloride and dry (MgSO$_4$). Evaporate the solvent in vacuo to give an oil. Purify by silica gel chromatography (gradient 50% ethyl acetate/hexane to ethyl acetate) to give the title compound (80.8 g, 67%) mp 129°–132° C.

Scheme D, step b:
N-[2-(1,3Dihydro-1,3-dioxo-2H-isoindol-2-yl)-1-oxo-3-phenylpropyl]-O-2-propenyl-L-serine, methyl ester Dissolve N-[2-(1,3-dihydro-1,3-dioxo-2H-isoindol-2-yl)-1- oxo-3-phenylpropyl]-L-serine, methyl ester (25 g, 63 mmol) in methylene chloride/cyclohexane (1:1, 600 mL). Add allyl trichloroacetimidate (26 g, 128 mmol) and trifluoromethanesuihfonic acid (5 mL), 56.6 mmol). Stir at room temperature under a nitrogen atmosphere for 5 hours and dilute with methylene chloride. Wash with saturated aqueous sodium hydrogen carbonate, water, dry (MgSO$_4$) and evaporate the solvent in vacuo. Purify by silica gel chromatography (gradient 20% ethyl acetate/hexane to 35% ethyl acetate/hexane) to give the title compound; mp 95°–97° C.

Scheme D, step c: .[S-(R*, R*)]-N-[2-(1,3-Dihydro-1,3-dioxo-2H-isoindol-2-yl)-1-oxo-3-phenylpropyl]-3,4-dihydro-2H-1,4-oxazine-3-carboxylic acid, methyl ester Dissolve N-[2-(1,3-dihydro-1,3-dioxo-2H-isoindol-2-yl)-1-oxo-3-phenylpropyl]-O-2-propenyl-L-serine, methyl ester (13 g, 29.8 mmol) in methylene chloride/methanol (10:1, 220 mL). Cool to −78° C. and sparge with a mixture of ozone/oxygen for approximately 10 minutes until a blue color persists. Sparge with nitrogen for 10 minutes at −78° C. to remove excess ozone. Treat with methyl sulfide (60 mL, 0.82 mol) and allow to warm to room temperature. Stir at room temperature for 2.5 hours, evaporate the solvent in vacuo and dissolve the residue in ethyl acetate (200 mL). Wash with water, saturated sodium chloride, dry (MgSO$_4$) and evaporate the solvent in vacuo to give the intermediate N-[2-(1,3-dihydro-1,3-dioxo-2H-isoindol-2-yl)-1-oxo-3-phenylpropyl]-O-2-oxoethyl-L-serine, methyl ester as a foam (13.6 g).

Dissolve N-[2-(1,3-dihydro-1,3-dioxo-2H-isoindol-2-yl)-1-oxo3-phenylpropyl]-O-2-oxoethyl-L-serine, methyl ester (13.6 g) in methylene chloride/trifluoroacetic acid (10:1/330 mL). Stir at room temperature for 2.5 hours and evaporate the solvent in vacuo. Purify by silica gel chromatography (35% ethyl acetate/hexane) and recrystallize (ethyl acetate/hexane) to give the title compound (8.52 g, 68%); mp 70°–72° C.

Scheme D, step d: [4S-[4α, 7α(R*), 12bβ]]-7-[(1,3-Dihydro-1,3-dioxo-2H-isoindol-2-yl)]-3,4,6,7,8,12b-hexahydro-6-oxo-1H-[1,4]-oxazino-[3,4-a][2]benz-azepine-4-carboxylic acid, diphenylmethyl ester Dissolve [S-(R*, R*)]-N-[2-(1,3-dihydro-1,3-dioxo-2H-isoindol- 2-yl)-1-oxo-3-phenylpropyl]-3,4-dihydro-2H-1,4-oxazine- 3-carboxylic acid, methyl ester (2.5 g, 5.9 mmol) in methylene chloride (5 mL) and add, by dropwise addition, to a previously prepared solution of trifluoromethanesulfonic acid (4.0 mL, 45 mmol) and trifluoroacetic anhydride (1.0 mL, 7.1 mmol). Place under a nitrogen atmosphere and stir at room temperature for 123 hours. Pour into a separatory funnel containing ice (200 g) and ethyl acetate (200 mL). Separate the organic phase, wash with water (3×200 mL) and saturated aqueous sodium chloride (100 mL). Extract the organic phase with 10% wt. potassium hydrogen carbonate (4×40 mL) and water (40 mL). Layer the combined basic aqueous phases with ethyl acetate (100 mL) and cool in an ice bath. Add, by dropwise addition, 6N hydrochloric acid to adjust the pH 1 while maintaining the temperature at 5°–10° C. Separate t he organic phase and extract the aqueous phase with ethyl acetate (3×200 mL), wash with saturated sodium chloride and dry (MgSO$_4$). Evaporate the solvent in vacuo and dry the residue under high vacuum at 56° C. for 24 hours to give the intermediate [4S-[4α, 7α(R*), 12bβ]]-7-[(1,3-dihydro-1,3-dioxo-2H-isoindol-2-yl)]-3,4,6,7,8,12b-hexahydro- 6-oxo-1H-[1,4]-oxazino[3,4-a][2]benzazepine-4-carboxylic acid (1.75 g, 73%).

Dissolve [4S-[4α, 7α(R*), 12bβ]]-7-[(1,3-dihydro-1,3-dioxo-2H-isoindol-2-yl)]-3,4,6,7,8,12b-hexahydro-6-oxo-1H-[1,4]-oxazino[3,4-a][2]benzazepine-4-carboxylic acid (500 mg, 1.23 mmol) in methylene chloride (12 mL) and treat with diphenyldiazomethane (360 mg, 1.86 mmol). Stir for 5.5 hours and evaporate the solvent in vacuo. Purify by silica gel chromatography (gradient 20% ethyl acetate/hexane to 35% ethyl acetate/hexane) to give the title compound (563 mg, 80%); mp 178°–181° C. (isopropanol).

Scheme D, step e: [4S-[4α-7α(R8), 12bβ]]-7-(Amino)-3,4,6,7,8,12b-hexahydro-6-oxo-1H-[1,4]-oxazino[3,4-a][2]benzazepine-4-carboxylic acid, diphenylmethyl ester Dissolve [4S-[4α, 7α(R*), 12bβ]]-7-[(1,3-dihydro-1,3-dioxo-2H-isoindol-2-yl)]-3,4,6,7,8,12b-hexahydro-6-oxo-1H-[1,4]-oxazino[3,4-a][2]benzazepine-4-carboxylic acid, diphenylmethyl ester (296 mg, 0.517 mmol) in methanol (5 mL) and treat with hydrazine monohydrate (1.1 mL of a 1M solution in methanol, 1.1 mmol). Stir at room temperature for 44 hours, evaporate the solvent in vacuo and slurry the residue in methylene chloride (10 mL). Filter and evaporate the solvent in vacuo to give the title compound (218 mg, 95%).

Scheme A, step a: [4S-[4α-7α(R*), 12bβ]]-7-[(1-Oxo-2(R)-bromo-3-phenylpropyl)amino]-1,2,3,4,6,7,8,12b-octahydro-$_6$-oxo-1H-[1,4]-oxazino[3,4-a][2]benzazepine-4-carboxylic acid, diphenylmethyl ester Mix [4S-[4α-7α(R*), 12bβ]]-7-amino-1,2,3,4,6,7,8,12b-octahydro- 6-oxo-1H-[1,4]-oxazino[3,4-a][2]benzazepine-4carboxylic acid, diphenylmethyl ester Mix [4S-[4α-7α(R*), 12bβ]]-7-amino-1,2,3,4,6,7,8,12b-octahydro-6-oxo-1H-[1,4]-oxazino[3,4-a][2]benzazepine-4-carboxylic acid, phenyl-2-bromopropionic acid (2.75 g, 12 mmol), 2-ethoxy-2-ethoxycarbonyl- 1,2-dihydro-quinoline (EEDQ ) (3.0 g, 12 mmol) and methylene chloride (25 mL). Stir at room temperature for 4 hours, dilute with methylene chloride, wash with 10% hydrochloric acid, saturated sodium hydrogen carbonate and brine. Dry (MgSO₄) and evaporate the solvent in vacuo. Purify by chromatography to give the title compound.

Scheme A, step c: [4S-[4α-7α(R*), 12bβ]]-7-[(1-Oxo-2(S)-( 4-morpholino)-acetylthio-3-phenylpropyl)amino]-1,2,3,4,6,7,8,12b-octahydro-6-oxo-1H-[1,4]-oxazino-[3,4-a][2]benzazepine-4-carboxylic acid, diphenylmethyl ester Suspend sodium hydride (175 mg of a 60% suspension, 4.0 mmol) in anhydrous dimethylformamide (4 mL) and place under a nitrogen atmosphere. Bubble hydrogen sulfide gas into the suspension until solution occurs . Add triphenylmethyl 4-morpholinethiolacetate (1.61 g, 4 .0 mmol) and heat gently for 1.5 hours while bubbling nitrogen through the solution to facilitate removal of excess hydrogen sulfide gas. Add [4S-[4α-7α(R*), 12bβ]]-7-[(1-oxo-2(R)-bromo-3-phenylpropyl)amino]-1,2,3,4,6,7,8,12b-octahydro-6-oxo-1H-[1,4]-oxazino[3,4-a][2]benzazepine-4-carboxylic acid, diphenylmethyl ester (2.0 mmol) and stir for 2 hours. Pour into water, extract into ethyl acetate, wash with brine and dry (MgSO₄). Evaporate the solvent in vacuo and purify by chromatography to give the title compound.

Scheme A, step d: [4S-4α-7α(R*), 12bβ]]-7-[(1-Oxo-2(S)-(4-morpholino)-acetylthio-3-phenylpropyl)amino]-1,2,3,4,6,7,8,12b-octahydro-6-oxo-1H-[1,4-oxazino[3,4-a][2]benzazepine-4-carboxylic acid•trifluoroacetate Mix [4S-[4α-7α(R*), 12bβ]]-7-[(1-oxo-2(S)-(4-morpholino)-acetylthio- 3-phenylpropyl)amino]-1,2,3,4,6,7, 8,12b-octahydro- 6-oxo-1H-[1,4]-oxazino[3,4-a][2] benzazepine-4-carboxylic acid, diphenylmethyl ester (2.0 mmol), anisole (0.5 mL) and methylene chloride (6 mL). Place under a nitrogen atmosphere and cool to −50° C. Add trifluroracetic acid (3.0 mL) over 1 minutes and allow to warm to room temperature over 2 hours while stirring. Evaporate the solvent in vacuo, triturate with hexane and methylene chloride and dry under high vacuum to give the title compound.

EXAMPLE 6

[4S-[4α-7α(R*), 12bβ]]-7-[(1-Oxo-2(S)-4-morpholino)-acetylthio-3-phenylpropyl)amino]-1,2,3,4,6,7,8,12b-hexahydro-6-oxo-1H-[4]-thiazino[3,4-a][2]benzazepine-4-carboxylic acid•trifluoroacetate

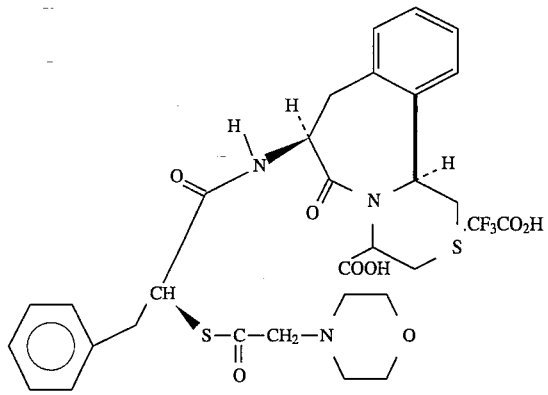

Scheme A, Step a: [4S-[4α-7α(R*), 12bβ]]-7-[(1-Oxo-2(R)-bromo-3-phenylpropyl)amino]-1,2,3,4,6,7,8,12b-octahydro-6-oxo- 1H-[1,4]-thiazino[3,4-a][2]benzazepine-4-carboxylic acid, diphenylmethyl ester Mix [4S-[4α-7α(R*), 12bβ]]-7-amino-1,2,3,4,6,7,8,12b-octahydro- 6-oxo-1H-[1,4]-thiazino[3,4-a][2]benzazepine-4carboxylic acid, diphenylmethyl ester (10 mmol), (R)-3-phenyl- 2-bromopropionic acid (2.75 g, 12 mmol), 2-ethoxy-2-ethoxycarbonyl- 1,2-dihydro-quinoline (EEDQ ) (3.0 g, 12 mmol) and methylene chloride (25 mL). Stir at room temperature for 4 hours, dilute with methylene chloride, wash with 10% hydrochloric acid, saturated sodium hydrogen carbonate and brine. Dry (MgSO₄) and evaporate the solvent in vacuo. Purify by chromatography to give the title compound.

Scheme A, step c: [4S-[4α-7α(R*), 12bβ]]-7-[(1-Oxo-2(S)-( 4-morpholino)-acetylthio-3phenypropyl)amino]-1,2,3,4,6,7,8,12b-octahydro-6-oxo-1H-[1,4]-thiazino[3,4-a][2]benzazepine-4-carboxylic acid, diphenylmethyl ester Suspend sodium hydride (175 mg of a 60% suspension, 4.0 mmol) in anhydrous dimethylformamide (4 mL) and place under a nitrogen atmosphere. Bubble hydrogen sulfide gas into the suspension until solution occurs. Add triphenylmethyl 4-morpholinethiolace tate (1.61 g, 4.0 mmol) and heat gently for 1.5 hours while bubbling nitrogen through the solution to facilitate removal of excess hydrogen sulfide gas. Add [4S-[4α-7α(R*), 12 bβ]]-7-[(1-oxo-2(R)-bromo-3-phenylpropyl)amino]-1,2,3,4,6,7,8,12b-octahydro-6-oxo-1H-[1,4]-thiazino[3,4-a][2]benzazepine-4-carboxylic acid, diphenylmethyl ester (2.0 mmol) and stir for 2 hours. Pour into water, extract into ethyl acetate, wash with brine and dry (MgSO₄). Evaporate the solvent in vacuo and purify by chromatography to give the title compound.

Scheme A, step d: [4S-4α-7α(R*), 12bβ]]-7-[(1-Oxo-2(S)-(4-morpholino)-acetylthio-3-phenylpropyl)amino]-1,2,3,4,6,7,812b-octahydro-6-oxo-1H-[1,4]-thiazino[3,4-a][2]benzazepine-4carboxylic acid•trifluoroacetate Mix [4S-[4α-7α(R*), 12bβ]]-7-[(1-oxo-2(S)-(4-morpholino)-acetylthio-3-phenylpropyl)amino]-1,2,3,4,6,7,8,12b-octahydro-6-oxo-1H-[1,4]-thiazino[3,4-a][2]benzazepine-4-carboxylic acid, diphenylmethyl ester (2.0 mmol), anisole (0.5 mL) and methylene chloride (6 mL). Place under a nitrogen atmosphere and cool to −50° C. Add trifluoroacetic acid (3.0 mL) over 1 minute and allow to warm to room temperature over 2 hours while stirring. Evaporate the solvent in vacuo, triturate with hexane and methylene chloride and dry under high vacuum to give the title compound.

EXAMPLE 7

[4S-[4α-7α(R*), 12bβ]]-7-[(1-Oxo-2(S)-(1-piperidino)-acetylthio-3-phenylpropyl)amino]-1,2,3,4,6,7,8,12b-hexahydro-6-oxopyyrido[2]benzazepine-4-carboxylic acid•trifluoroacetate

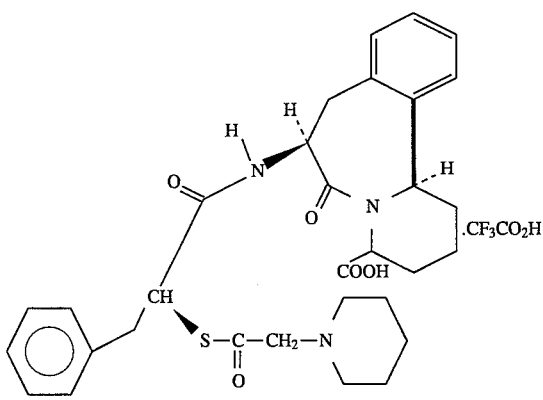

Scheme C, step d. [4S-[4α-7α(R*), 12bβ]]-7-[(1-Oxo-2(S)-( 1-piperidino)-acetyithio-3-phenylpropyl)amino]-1,2,3,4,6,7,8,12b-hexahydro-6-oxopyrido[2,1-a][2]benzazepine-4-caroxylic acid, diphenylmethyl ester Dissolve t-butyl bromoacetate (1 eq) in tetrahydrofuran and add piperidine (2.2 eq) via syringe. Stir the reaction mixture at room temperature for 2 hours, filter and wash the filter cake with ethyl acetate. Combine the organic filtrates and wash with saturated sodium bicarbonate (2×), water (2×) and brine. Dry ($Na_2SO_4$), filter and evaporate the solvent in vacuo. Take up the oily residue in ethyl acetate, cool in ice and bubble hydrogen chloride gas into the solution. Stir at room temperature overnight, cool and filter to give 1-piperidinoacetic acid hydrochloride salt (56%); mp 215°–217° C.; $^1$H NMR ($D_2O$) δ3.84 (s, 2), 3.41–3.51 (m, 2), 2.83–2.97 (m, 2), 1.56–1.87 (m, 5), 1.25–1.45 (m, 1).

Suspend 1-piperidinoacetic acid hydrochloride salt (4.9 mmol) in degassed dimethylformamide (40 mL) and add carbonyldiimidazole (0.477 g, 2.94 mmol). Stir the reaction mixture at room temperature for 1.5 hours. Add a solution of [4S-4α-7α(R*), 12bβ]]-7-[(1-Oxo-2(S)-thio-3-phenylpropyl)amino]-1,2,3,4,6,7,8,12b-octahydro-6-oxopyrido[2,1-a][2]benzazepine-4-carboxylic acid, diphenylmethyl ester (2.45 mmol) in degassed tetrahydrofuran and stir at room temperature overnight. Dilute with ethyl acetate, wash with water (2×) and brine, dry ($MgSO_4$) and evaporate the solvent in vacuo to give the title compound (96%).

$^1$H NMR ($CDCl_3$) δ7.42 (d, 1, J=9 Hz), 7.17–7.38 (m, 12), 6.90–7.15 (m, 6), 6.60 (m, 1), 6.28 (s, 1), 5.56 (m, 1), 5.31–5.44 (m, 2), 4.29 (t, 1, J=6 Hz), 3.14–3.42 (m, 4), 2.85–3.08 (m, 3), 2.30–2.58 (m, 7), 1.54–2.05 (m, 6), 1.37–1.52 (m, 2).

Scheme A, step d: [4S-4α-7α(R*), 12bβ]]-7-[(1-Oxo-2-(S)-(4-piperidino 1-acetylthio-3-phenylpropyl)amino]-1,2,3,4,6,8,12b-octahydro-6-oxopyridol[2,1-a][2]benzazepine-4-carboxylic acid•trifluoroacetate Dissolve [4S-[4α-7α(R*), 12bβ]]-7-[(1-Oxo-2(S)-( 4-piperidino-acetylthio-3-phenylpropyl)amino]-1,2,3,4,6,7,8,12b-octahydro-6-oxopyrido[2,1-a][2]benzazepine-4-carboxylic acid, diphenylmethyl ester (1.86 mmol) and anisole (1.5 mL, excess) in methylene chloride (20 mL), cool to −50° C. and add trifluoroacetic acid (3 mL). Stir the reaction mixture at −50° C. for 2.5 hours, evaporate the solvent in vacuo and triturate with hexane (4×). Take up the residue in a minimal amount of methylene chloride and precipitate from hexane (3×) to give the title compound (40% ).

IR (KBr) 3389, 3064, 3029, 2949, 2872, 1672, 1496, 1442, 1342, 1277, 1199, 1136 $cm^{-1}$, $^1$H NMR ($CDCl_3$) δ7.83 (d, 1, J=7.5 Hz), 6.89–7.41 (m, 9), 5.63–5.79 (m, 1), 5.39–5.50 (m, 1), 5.03–5.16 (m, 1), 4.60 (dd, 1, J=6, 7.5 Hz), 3.98 (s, 2), 3.28–3.67 (m, 4), 2.66–3.12 (m, 4), 2.25–2.67 (m, 2), 1.62–2.08 (m, 10); $^{19}$F NMR (DMSO-d6) δ−73.3; $^{13}$C NMR (DMSO-d6) δ171.8, 171.3, 168.5, 137.4, 136.8, 136.6, 130.1, 129.3, 128.2, 126.8, 126.7, 125.4, 124.9, 119.3, 53.0, 50.6, 49.9, 48.3, 37.5, 35.9, 25.0, 24.7, 22.5, 21.3, 16.9; MS (CI, 70 eV) m/z 564 [$M^+$+H], 144.

EXAMPLE 8

[4S-[4α-7α(R*), 12bβ]]-7-[(1-Oxo-2(S)-(1-piperidino)-acetylthio-3-phenylpropyl)amino]-1,2,3,4,6,7,8,12b-hexahydro-6-oxo-1H-[1,4]-oxazino[3,4-a][2]benzazepine-4-carboxylic acid•trifluoroacetate

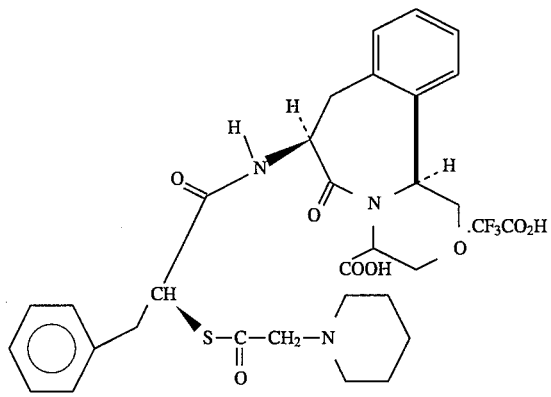

Scheme A, step c: [4S-[4α-7α(R*), 12bβ]]-7-[(1-Oxo-2(S)-(1-piperidino)-acetylthio-3-phenylpropyl)amino]-1,2,3,4,6,7,8,12b-octahydro-6-oxo-1H-[1,4]-oxazino-[3,4-a][2]benzazepine-4-carboxylic acid, diphenylmethyl ester Suspend sodium hydride (175 mg of a 60% suspension, 4.0 mmol) in anhydrous dimethylformamide (4 mL) and place under a nitrogen atmosphere. Bubble hydrogen sulfide gas into the suspension until solution occurs Add triphenylmethyl 4-piperidinethiolacetate (4.0 mmol) and heat gently for 1.5 hours while bubbling nitrogen through the solution to facilitate removal of excess hydrogen sulfide gas. Add [4S-[4α-7α(R*), 12bβ]]-7-[(1-oxo-2(R)-bromo-3-phenylpropyl)amino]-1,2,3,4,6,7,8,12b-octahydro-6-oxo-1H-[1,4]-oxazino[3,4-a][2]benzazepine-4-carboxylic acid, diphenylmethyl ester (2.0 mmol) and stir for 2 hours. Pour into water, extract into ethyl acetate, wash with brine and dry (MgSO₄). Evaporate the solvent in vacuo and purify by chromatography to give the title compound.

Scheme A, step d: [4S-[4α-7α(R*), 12bβ]]-7-[(1-Oxo-2(S)-(1-piperidino)-acetylthio-3-phenylpropyl)amino]-1,2,3,4,6,7,8,12b-octahydro-6-oxo-1H-[1,4]-oxazino[3,4-a][2]benzazepine-4-carboxylic acid Mix [4S-[4α-7α(R*), 12bβ]]-7-[(1-oxo-2(S)-(1-piperidino)-acetylthio- 3-phenylpropyl)amino]-1,2,3,4,6,7,8,12b-octahydro- 6-oxo-1H -[1,4]-oxazino[3,4-a][2] benzazepine-4-carboxylic acid•diphenylmethyl ester (2.0 mmol), anisole (0.5 mL) and methylene chloride (6 mL). Place under a nitrogen atmosphere and cool to −50° C. Add trifluoroacetic acid (3.0 mL) over 1 minute and allow to warm to room temperature over 2 hours while stirring. Evaporate the solvent in vacuo, triturate with hexane and methylene chloride and dry under high vacuum to give the title compound.

EXAMPLE 9

[4S-[4α-7α(R*), 12bβ]]-7-[(1-Oxo-2(S)-(1-piperidino)-acetylthio-3-phenylpropyl)amino]-1,2,3,4,6,7,8,12b-hexahydro-6-oxo-1H-[1,4]-thiazino[3,4-a][2]benzazepine-4-carboxylic acid•trifluoroacetate

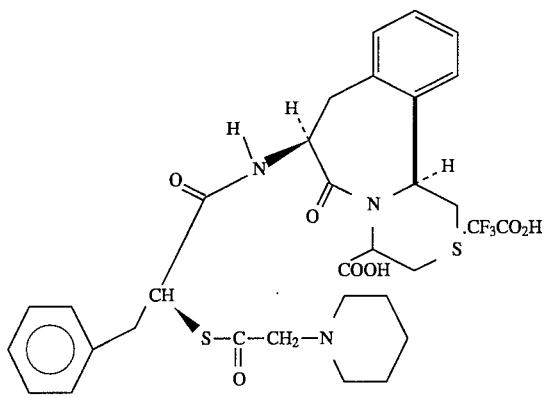

Scheme A, step c: [4S-4α-7α(R*), 12bβ]]-7-[(1-Oxo-2(S)-( 1-piperidino)-acetylthio-3-phenylpropyl)amino]-1,2,3,4,6,7,8,12b-octahydro-6-oxo-1H-[1,4]-thiazino[3,4-a][2]benzazepine-4-carboxylic acid, diphenylmethyl ester Suspend sodium hydride (175 mg of a 60% suspension, 4.0 mmol) in anhydrous dimethylformamide (4 mL) and place under a nitrogen atmosphere. Bubble hydrogen sulfide gas into the suspension until solution occurs. Add triphenylmethyl 4-piperidinethiolacetate (4.0 mmol) and heat gently for 1.5 hours while bubbling nitrogen through the solution to facilitate removal of excess hydrogen sulfide gas. Add [4S-[4α-7α(R*), 12bβ]]-7-[(1-oxo-2(R)-bromo-3-phenylpropyl)amino]-1,2,3,4,6,7,8,12b-octahydro-6-oxo-1H-[1,4]-thiazino[3,4-a][2]benzazepine-4-carboxylic acid, diphenylmethyl ester (2.0 mmol) and stir for 2 hours. Pour into water, extract into ethyl acetate, wash with brine and dry (MgSO₄). Evaporate the solvent in vacuo and purify by chromatography to give the title compound.

Scheme A, Step d: [4S-[4α-7α(R*), 12bβ]]-7-[(1-Oxo-2(S)-(1-piperidino)-acetylthio-3-phenylpropyl)amino]-1,2,3,4,6,7,8,12b-octahydro-6-oxo-1H-[1,4]-thiazino-[3,4-a][2]benzazepine-4-carboxylic acid•trifluoroacetate Mix [4S-[4α-7α(R*), 12bβ]]-7-[(1-oxo-2(S)-(1-piperidino)-acetylthio- 3-phenylpropyl)amino]-1,2,3,4,6,7, 8,12b-octahydro- 6-oxo-1H-[1,4]-thiazino[3,4-a][2] benzazepine-4-carboxylic acid•diphenylmethyl ester (2.0 mmol), anisole (0.5 mL) and methylene chloride (6 mL). Place under a nitrogen atmosphere and cool to −50° C. Add trifluoroacetic acid (3.0 mL) over 1 minute and allow to warm to room temperature over 2 hours while stirring. Evaporate the solvent in vacuo, triturate with hexane and methylene chloride and dry under high vacuum to give the title compound.

EXAMPLE 10

[4S-[4α-7α(R*), 12β]]-7-[(1-Oxo-2(S)-(4-thiomorpholino)-acetylthio-3-phenylropyl)amino]-1,2,3,4,6,7,8,12b-hexahydro-6-oxopyrido[2,1-a][2]benzazepine-4-carboxylic acid•trifluoroacetate

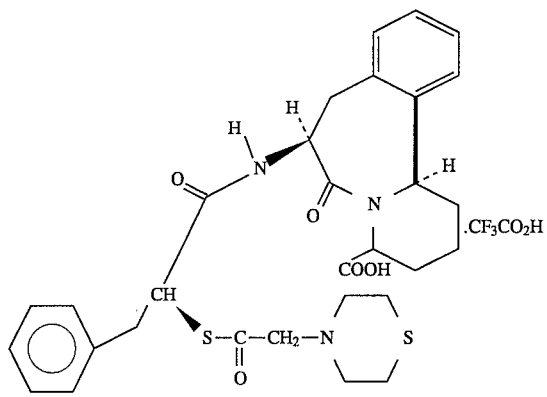

Scheme B, steps a and b: Triphenylmethyl 4-thiomorpholinethietate.

Dissolve triphenylmethyl mercaptan (9.2 g, 33.3 mmol) in methylene chloride (50 mL) and add pyridine (4 mL). Cool to −50° C. and add bromoacetyl bromide (2.9 mL) and stir vigorously for 20 minutes. Remove the ice bath and allow to warm to room temperature. Add, by dropwise addition, thiomorpholine (10 g, 96.9 mmol) at such a rate that the temperature does not rise above 25° C. Stir for 2.5 hours, pour into methylene chloride and wash with water. Dry (MgSO$_4$), filter, evaporate the solvent in vacuo and purify by silica gel chromatography (hexane:ethyl acetate/4:1) to give the title compound as a solid (5.38 g, 41%).

$^1$H NMR (CDCl$_3$) δ7.28 (m, 5), 3.21 (s, 2), 2.62–2.88 (m, 4).

Scheme A, step c: [4S -4α-7α(R*), 12bβ]]-7-[(1-Oxo-2(S)-(4-thiomorpholinol-acetylthio-3-phenylpropyl)amino]-1,2,3,4,6,7,8,12b-octahydro-6-oxopyrido[2,1-a][2]benzazepine-4-carboxylic acid, diphenylmethyl ester Suspend sodium hydride (0.32 g of a 60% suspension, 8.0 mmol) in anhydrous dimethylformamide (8 mL) and place under a nitrogen atmosphere. Bubble hydrogen sulfide gas into the suspension until solution occurs. Stir for 10 minutes and add triphenylmethyl 4-thiomorpholinethiolacetate (3.35 g, 8.0 mmol) and bubbling nitrogen through the solution to facilitate removal of excess hydrogen sulfide gas for 1.5 hours. Add, by slow addition, a solution of [4S-[4α-7α(R*), 12bβ]]-7-[(1-oxo-2(R)-bromo-3-phenylpropyl)amino]-1,2, 3,4,6,7,8,12b-octahydro-6-oxopyrido[2,1-a][2]benzazepine-4-carboxylic acid, diphenylmethyl ester (2.6 g, 3.99 mmol) in dimethylformamide (8 mL). Stir at room temperature for 3 hours, pour into water and extract into ethyl acetate, (3×). Wash with brine, dry (MgSO$_4$) and evaporate the solvent in vacuo. Purify by chromatography (hexane:ethyl acetate/9:1 to 4:1 to 1:1) to give the title compound.

$^1$H NMR (CDCl$_{13}$) δ87.44 (d, 1, J=7.5 Hz), 7.16–7.37 (m, 10), 6.89–7.14 (m, 8), 6.59–6.68 (m, 1), 6.30 (s, 1), 5.51–5.63 (m,), 5.30–5.42 (m, 2), 4.28 (t, 1, J=6.0 Hz), 3.17–3.45 (m, 4), 3.03 (dd, 1, J=7.5, 12 Hz), 2.63–2.88 (m, 8), 2.32– 2.61 (m, 3), 1.61–2.03 (m, 4); MS (CI, 70 eV) m/z 748 [M$^+$+H], 572, 178, 167, 116.

Scheme A, step d: 4S-[4α-7α(R*), 12bβ]]-7-[(1-Oxo-2(S)-(4-thiomorpholinol)-acetylthio-3-phenylpropyl)amino]-1,2,3,4,6,7,8,12b-octahydro-6-oxopyrido[2,1-a][2]benzazepine-4-carboxylic acid•trifluoroacetate Dissolve [4S-[4α-7α(R*), 12bβ]]-7-[(1-oxo-2(S)-(4-thiomorpholino)-acetylthio-3-phenylpropyl)amino]-1,2,3, 4,6,7,8,12b-octahydro-6-oxopyrido[2,1-a][2]benzazepine-4-carboxylic acid, diphenylmethyl ester (1.86 mmol) and anisole (1.5 mL, excess) in methylene chloride (20 mL), cool to −50° C. and add trifluoroacetic acid (3 mL). Stir the reaction mixture at −50° C. for 2.5 hours, evaporate the solvent in vacuo and triturate with hexane (4×). Take up the residue in a minimal amount of methylene chloride and precipitate from hexane (3×) to give the title compound (75%).

$^1$H NMR (CDCl$_3$) δ7.63 (d, 1, J=7.5 Hz), 6.93–7.42 (m, 9), 5.58–6.74 (m, 1), 5.38–5.50 (m, 1), 5.00–5.12 (m, 1), 4.51 (dd, 1, J=6, 9 Hz), 3.90 (s, 2), 3.16–3.51 (m, 6), 3.06 (dd, 1, J=9, 15 Hz), 2.68–2.95 (m, 6), 2.12–2.57 (m, 2), 1.60–2.05 (m, 4); $^{19}$F NMR (CDCl$_3$) δ−76.3; MS (CI, 70 eV) m/z 582 [M$^+$+H], 178, 162, 116.

EXAMPLE 11

[4S-[4α-7α(R*), 12bβ]]-7-[(1-Oxo-2(S)-(4-thiomorpholino)-acetylthio-3-phenylpropyl)amino]-1,2,3,4,6,7,8,12b-hexahydro-6-oxo-1H-[1,4]-oxazino[3,4-a][2]benzazepine-4-carboxylic acid•trifluoroacetate

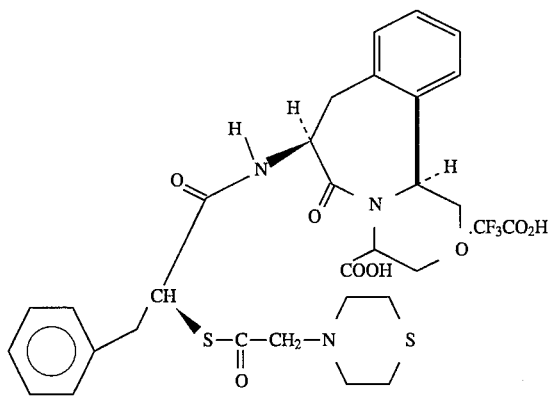

Scheme A, step c: [4S-[4α-7α(R*), 12bβ]]-7-[(1-Oxo-2(S)-(4-thiomorpholino)-acetylthio-3-phenylpropyl)amino]-1,2,3,4,6,7,8,12b-octahydro-6-oxo-1H-[1,4]-oxazino[3,4-a][2]benzazepine-4-carboxylic acid, diphenylmethyl ester Suspend sodium hydride (175 mg of a 60% suspension, 4.0 mmol) in anhydrous dimethylformamide (4 mL) and place under a nitrogen atmosphere. Bubble hydrogen sulfide gas into the suspension until solution occurs. Add triphenylmethyl 4-thiomorpholinethiolacetate (4.0 mmol) and heat gently for 1.5 hours while bubbling nitrogen through the solution to facilitate removal of excess hydrogen sulfide gas. Add [4S-[4α-7α(R*), 12bβ]]-7-[(1-oxo-2(R)-bromo-3-phenylpropyl)amino]-1,2,3,4,6,7,8,12b-octahydro-6-oxo-1H-[1,4]-oxazino[3,4-a][2]benzazepine-4-carboxylic acid,diphenylmethyl ester (2.0 mmol) and stir for 2 hours. Pour into water, extract into ethyl acetate, wash with brine and dry (MgSO$_4$). Evaporate the solvent in vacuo and purify by chromatography to give the title compound.

Scheme A, step d: [4S-[4α-7α(R*), 12bβ]]-7-[(1-Oxo-2(S)-(4-thiomorpholino)-acetylthio-3-phenylpropyl)amino]-1,2,3,4,6,7,8,12b-octahydro-6-oxo-1H-[1,4]-oxazino[3,4-a][2]benzazepine-4-carboxylic acid•trifluoroacetate Mix [4S-[4α-7α(R*), 12bβ]]-7-[(1-oxo-2(S)-(4-thiomorpholino)-acetylthio- 3-phenylpropyl)amino]-1,2, 3,4,6,7,8,12b-octahydro-6-oxo-1H-[1,4]-oxazino[3,4-a][2] benzazepine-4-carboxylic acid, diphenylmethyl ester (2.0 mmol), anisole (0 .5 mL) and methylene chloride (6 mL). Place under a nitrogen atmosphere and cool to −50° C. Add trifluroracetic acid (3.0 mL) over 1 minutes and allow to warm to room temperature over 2 hours while stirring. Evaporate the solvent in vacuo, triturate with hexane and methylene chloride and dry under high vacuum to give the title compound.

EXAMPLE 12

[4S-[4α-7α(R*), 12bβ]]-7-[(1-Oxo-2(S)-[4-thiomorpholino)-acetyl thio-3-phenylpropyl)amino]-1,2,3,4,6,7,8,12b-hexahydro-6-oxo-1H-[1,4]-thiazino[3,4-a][2]benzazepine-4-carboxylic acid•trifluoroacetate

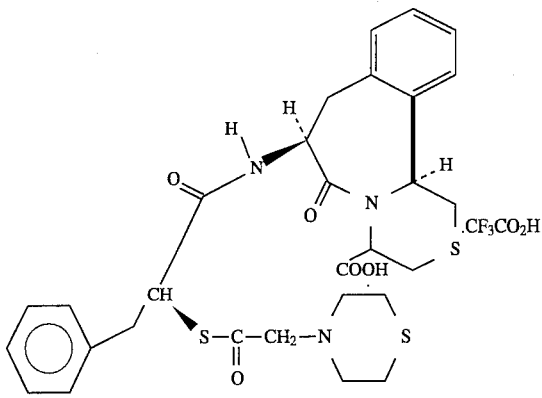

Scheme A, step c: [4S-[4α-7α(R*), 12bβ]]-7-[(1-Oxo-2(S)-(4-thiomorpholino)-acetylthio-3-phenylpropyl)amino]-1,2,3,4,6,7,8,12b-octahydro-6-oxo-1H-[1,4]-thiazino-[3,4-a][2]benzazepine-4-carboxylic acid, diphenylmethyl ester Suspend sodium hydride (175 mg of a 60% suspension, 4.0 mmol) in anhydrous dimethylformamide (4 mL) and place under a nitrogen atmosphere. Bubble hydrogen sulfide gas into the suspension until solution occurs. Add triphenylmethyl 4-thiomorpholinethiolacetate (4.0 mmol) and heat gently for 1.5 hours while bubbling nitrogen through the solution to facilitate removal of excess hydrogen sulfide gas. Add [4S-[4α-7α(R*), 12bβ]]-7-[(1-oxo-2(R)-bromo-3-phenylpropyl)amino]-1,2,3,4,6,7,8,12b-octahydro-6-oxo-1H-[1,4]-thiazino[3,4-a][2]benzazepine-4-carboxylic acid, diphenylmethyl ester (2.0 mmol) and stir for 2 hours. Pour into water, extract into ethyl acetate, wash with brine and dry (MgSO₄). Evaporate the solvent in vacuo and purify by chromatography to give the title compound.

Scheme A, step d: 4S-[4α-7α(R*), 12bβ]]-7-[(1-Oxo-2(S)-(4-thiomorpholino)-acetylthio-3-phenylpropyl)amino]-1,2,3,4,6,7,8,12b-octahydro-6-oxo-1H-[1,4]-thiazino[3,4-a][2]benzazepine-4-carboxylic acid•trifluoracetate Mix [4S-[4α-7α(R*), 12bβ]]-7-[(1-oxo-2(S)-(4-thiomorpholino)-acetylthio- 3-phenylpropyl)amino]-1,2,3,4,6,7,8,12b-octahydro-6-oxo-1H-[1,4]-thiazino[3,4-a][2]benzazepine-4-carboxylic acid, diphenylmethyl ester (2.0 mmol), anisole (0.5 mL) and methylene chloride (6 mL). Place under a nitrogen atmosphere and cool to −50° C. Add trifluoroacetic acid (3.0 mL) over 1 minute and allow to warm to room temperature over 2 hours while stirring. Evaporate the solvent in vacuo, triturate with hexane and methylene chloride and dry under high vacuum to give the title compound.

EXAMPLE 13

[4S-[4α-7α(R*), 12bβ]]1-Oxo-2(S)-4-thiomorpholino-1-oxide)-acetylthio-3-phenylpropyl)amino]-1,2,3,4,6,7,8,12b-hexahydro- 6-oxopyridol-a][2]benzazepine-4-carboxylic acid•trifluoroacetate

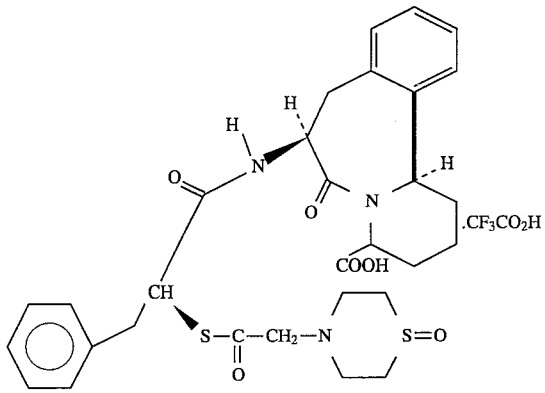

Method A

Scheme B, optional step c: Triphenylmethyl 4-thiomorpholine-1-oxide-thiolacetate Dissolve triphenylmethyl 4-thiomorpholinethiolacetate (5.39 mmol) in methylene chloride (25 mL), place under nitrogen atmosphere and cool to −20° C. Add, by dropwise addition, a solution of meta-chloroperbenzoic acid (930 mg, 5.39 mmol) in methylene chloride (25 mL). Stir overnight at room temperature. Filter and treat with aqueous sodium metabisulfite (until negative starch-iodide test) and separate the layers. Wash the organic phase with 5N sodium hydroxide until basic and dry (MgSO₄). Evaporate the solvent in vacuo to give the title compound.

Scheme A, step c: [4S-[4α-7α(R*), 12bβ]]-7-[(1Oxo-2(S)- 4-thiomorpholino-1-oxide)-acetylthio-3-phenylpropyl)amino]-1,2,3,4,6,7,8,12b-octahydro-6-oxopyrido[2,1-a][2]-benzazepine-4-carboxylic acid, diphenylmethyl ester Suspend sodium hydride (175 mg of a 60% suspension, 4.0 mmol) in anhydrous dimethylformamide (4 mL) and place under a nitrogen atmosphere. Bubble hydrogen sulfide gas into the suspension until solution occurs. Add triphenylmethyl 4-thiomorpholine- 1-oxide-thiolacetate (4.0 mmol) and heat gently for 1.5 hours while bubbling nitrogen through the solution to facilitate removal of excess hydrogen sulfide gas. Add [4S-[4α-7α(R*), 12bβ]]-7-[(1-oxo-2(R)-bromo-3-phenylpropyl)amino]-1,2,3,4,6,7,8,12b-octahydro-6-oxopyrido[ 2,1-a][2]benzazepine-4-carboxylic acid, diphenylmethyl ester (1.3 g, 2.0 mmol) and stir for 2 hours. Pour into water, extract into ethyl acetate, wash with brine and dry (MgSO₄). Evaporate the solvent in vacuo and purify by chromatography to give the title compound.

Scheme A, step d: [4S-[4α-7α(R*), 12bβ]]-7-[(1-Oxo-2(S)-(4-thiomorpholino-1-oxide)-acetylthio-3-phenylpropyl)amino]-1,2,3,4,6,7,8,12b-octahydro-6-oxopyrido[2,1-a][2]benzazepine-4-carboxylic acid•trifluoroacetate Mix [4S-[4α-7α(R*), 12bβ]]-7-[(1-oxo-2(S)-(4-thiomorpholino- 1-oxide)-acetylthio-3- phenylpropyl)amino]-1,2,3,4,6,7,8,12b-octahydro-6-oxopyrido[2,1-a][2]benzazepine-4-carboxylic acid, diphenylmethyl ester (2.0 mmol), anisole(0.5 mL) and methylene chloride (6 mL). Place under a nitrogen atmosphere and cool to −50° C. Add trifluoroacetic acid (3.0 mL) over 1 minute and allow to warm to room temperature over 2 hours while stirring. Evaporate the solvent in vacuo and purify by chromatography to give the title compound.

Method B

[4S-[4α-7α(R*), 12bβ]]-7-[(1-Oxo-2(S)-(4-thiomorpholino-1-oxide)-acetylthio-3-phenylpropyl)amino]-1,2,3,4,6,7,-8,12b-octahydro- 6-oxopyrido[2,1-a]benzazepine-4-carboxylic acid•trifluoroacetate Dissolve [4S-[4α-7α(R*), 12bβ]]-7-[(1-Oxo-2(S)-(4-thiomorpholino)-acetylthio- 3-phenylpropyl)amino]-1,2,3,4,6,7,8,12b-octahydro-6-oxopyrido[2,1-a][2]benzazepine-4-carboxylic acid (1.52 g, 2.19 mmol) in ethanol/water (40 mL/10 mL) and add magnesium monoperoxyphthalic acid hexahydrate (0.603 g, 1.22 mmol). Stir the reaction mixture at room temperature for 30 minutes, evaporate the solvent in vacuo at 40° C. and take up the residue in methylene chloride. Dry (MgSO$_4$), evaporate the solvent in vacuo and purify by silica gel chromatography (methylene chloride:isopropanol/8:2 to 6:4) to give the title compound as a glassy solid (0.53 g, 41%).

IR (KBr) 3384, 3029, 2936, 2871, 1651, 1495, 1440, 1054, 1015, 756 cm$^{-1}$; $^1$H NMR (CDCl$_3$) δ7.51 (d, 1, J=4.8 Hz), 6.91–7.40 (m, 9), 5.58 (m, 1), 5.36–5.48 (m, 1), 5.08–5.20 (m, 1), 4.30 (t, 1, J=7.8 Hz), 3.51 (dd, 1, J=6, 16.5 Hz), 3.25–3.44 (m, 3), 3.09–3.25 (m, 2), 3.02 (dd, 1, J=8.4, 14.1 Hz), 2.65–2.94 (m, 6), 2.28–2.65 (m, 3), 1.52–2.04 (m, 3); $^{19}$F NMR (CDCl$_3$) δ75.8; $^{13}$C NMR (CDCl$_3$) δ199.2, 172.8, 171.9, 169.7, 137.6, 136.8, 135.6, 130.5, 129.4, 128.4, 127.4, 126.9, 125.6, 125.0, 66.6, 51.2, 51.1, 48.7, 47.7, 45.9, 44.2, 36.9, 36.7, 25.1, 17.2; MS (FAB) m/z 598 [M$^+$+H], 580, 552, 232.

Anal. Calcd for C$_{30}$H$_{35}$N$_3$O$_6$S$_2$•CF$_3$CO$_2$H: C, 53.95; H, 5.09; N, 5.90; Found: C, 53.98, H, 5.29; N, 5.78.

EXAMPLE 14

[4S-[4α-7α(R*), 12bβ]]-7-[(1-Oxo-2(S)-(4-thiomorpholino-1-1-dioxide)-acetylthio-3-phenylpropyl)amino]-1,2,3,4,6,7,8,12b-hexahydro-6-oxopyrido]2,1-a]-[2]benzazepine-4-carboxylic acid•trifluoroacetate

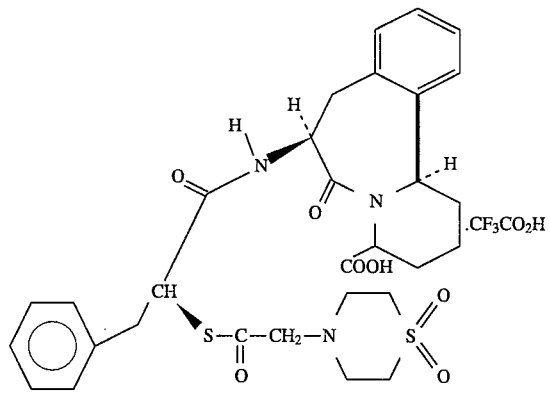

Method A

Scheme B, optional step c: Triphenylmethyl 4-thiomorpholine-1,1-dioxide-thiolacetate Dissolve triphenylmethyl 4-thiomorpholinethiolacetate (4.43 mmol) in methylene chloride (25 mL) and place under a nitrogen atmosphere. Add a solution of metachloroperbenzoic acid (1.53 g, 8.85 mmol) in methylene chloride (25 mL). Stir at room temperature overnight. Treat with aqueous sodium metabisulfite (until negative starch-iodide test) and separate the layers. Wash the organic phase with 5N sodium hydroxide until basic and dry (MgSO$_4$). Evaporate the solvent in vacuo to give the title compound.

Scheme A, step c: [4S-[4α-7α(R*), 12bβ]]-7-[(1-Oxo-2(S)-( 4-thiomorpholino-1,1-dioxide)-acetylthio-3-phenylpropyl)amino]-1,2,3,-4,6,7,8,12b-octahydro-6-oxopyrido[2,1-a][2]benzazepine-4-carboxylic acid, diphenylmethyl ester Suspend sodium hydride (175 mg of a 60% suspension, 4.0 mmol) in anhydrous dimethylformamide (4 mL) and place under a nitrogen atmosphere. Bubble hydrogen sulfide gas into the suspension until solution occurs. Add triphenylmethyl 4-thiomorpholine- 1,1-dioxide-thiolacetate (4.0 mmol) and heat gently for 1.5 hours while bubbling nitrogen through the solution to facilitate removal of excess hydrogen sulfide gas. Add [4S-[4α-7α(R*), 12 bβ]]-7-[(1-oxo-2(R)-bromo-3-phenylpropyl)amino]-1,2,3,4,6,7,8,12b-octahydro-6-oxopyrido[2,1-a][2]benzazepine-4-carboxylic acid, diphenylmethyl ester (1.3 g, 2.0 mmol) and stir for 2 hours. Pour into water, extract into ethyl acetate, wash with brine and dry (MgSO₄). Evaporate the solvent in vacuo and purify by chromatography to give the title compound.

Scheme A, step d: [4S-[4α-7α(R*), 12bβ]]-7-[(1-Oxo-2(S)-(4-thiomorpholino-1-dioxide-)-acetylthio-3-phenylpropyl)amino]-2,3,4,6,7,8,12b-octahydro-6-oxopyrido[2,1-a]benzazepine-4-carboxylic acid•trifluoroacetate Mix [4S-[4α-7α(R*), 12bβ]]-7-[(1-oxo-2(S)-(4-thiomorpholino-1,1-dioxide)-acetylthio-3phenylpropyl)amino]-1,2,3,4,6,7,8,12b-octahydro-6-oxopyrido[2,1-a][2]benzazepine-4-carboxylic acid, diphenylmethyl ester (2.0 mmol), anisole (0.5 mL) and methylene chloride (6 mL). Place under a nitrogen atmosphere and cool to −50° C. Add trifluoroacetic acid (3.0 mL) over 1 minute and allow to warm to room temperature over 2 hours while stirring. Evaporate the solvent in vacuo and purify by chromatography to give the title compound.

Method B

Scheme C, Step d: [4S-[4α-7α(R*), 12bβ]]-7-[(1-Oxo-2(S)-(4-thiomorpholino-1,1-dioxide)-acetylthio-3-phenylpropyl)amino]-1,2,3,4,6,7,8,12b-octahydro-6-oxopyrido[2,1-a][2]benzazepine-4-carboxylic acid, diphenylmethyl ester Suspend glycine (20 g, 0.266 mol) in water (50 mL) and add divinyl sulfone (26.7 mL, 0.2664 mol). Heat at 100° C. for 1.5 hours and cool to room temperature. Collect the precipitate by suction filtration, wash thoroughly with water and dry in vacuo at 50° C. overnight to give thiomorpholino-1,1-dioxide acetic acid (26.1 g, 51%); mp 177°–180° C.; IR (KBr) 3587, 3367, 3252, 3026, 2994, 1725, 1640, 1451, 1408, 1366, 1343, 1312, 1277, 1180, 1160, 1138, 1123, 1071, 1061 cm⁻¹; ¹H NMR (DMSO-d6) δ83.36 (s, 2), 3.05 (s, 4); ¹³C NMR (DMSO-d6) δ171.7, 56.8, 50.7, 49.6; MS (EI, 70 eV) m/z 193 (M⁺), 175, 148.

Anal. Calcd for $C_6H_{11}NO_4S \cdot H_2O$: C, 34.12; H, 6.20; N, 6.63; Found: C, 34.09; H, 6.2; N, 6.70.

Suspend thiomorpholino-1,1-dioxide acetic acid (0.947 g, 4.9 mmol) in degassed dimethylformamide (40 mL) and add carbonyldiimidazole (0.477 g, 2.94 mmol). Stir the reaction mixture at room temperature for 1.5 hours. Add a solution of [4S-[4α-7α(R*), 12bβ]]-7-[(1-Oxo-2(S)-thio-3-phenylpropyl)amino]-1,2,3,4,6,7,8,12b-octahydro-6-oxopyrido[2,1-a][2]benzazepine-4-carboxylic acid, diphenylmethyl ester (1.483 g, 2.45 mmol) in degassed tetrahydrofuran and stir the reaction mixture at room temperature overnight. Dilute with ethyl acetate, wash with water (2×) and brine, dry (MgSO₄) and evaporate the solvent in vacuo. Purify by silica gel chromatography (hexane:ethyl acetate/1:1 to 3:7) to give the title compound as a glassy solid (1.52 g, 80%).

IR (CHCl₃) 3381, 3032, 3011, 1736, 1651, 1497, 1439, 1308, 1128 cm⁻¹; ¹H NMR (CDCl₃) δ7.48 (d, 1, J=6.6 Hz), 7.17–7.38 (m, 12), 6.92–7.12 (m, 6), 6.68 (d, 1, J=6.9 Hz), 6.33 (s, 1), 5.57 (m, 1), 5.39 (m, 1), 5.32 (m, 1), 4.31 (dd, 1, J=6.3, 8.7 Hz), 3.39 (m, 4), 2.96–3.28 (m, 9), 2.59 (dd, 1, J=15, 18 Hz), 2.36–2.51 (m, 1), 1.88–2.03 (m, 1), 1.58–1.88 (m, 3); ¹³C NMR (CDCl₃) δ198.5, 171.7, 169.5, 169.4, 139.9, 139.1, 137.4, 136.4, 135.4, 130.7, 129.3, 128.4, 128.3, 128.2, 127.8, 127.7, 127.4, 127.0, 126.9, 126.8, 125.5, 124.7, 78.0, 65.7, 51.6, 51.4, 51.2, 51.1, 48.6, 48.1, 37.0, 36.6, 25.1, 25.0, 17.2; MS (FAB) m/z 780 [M⁺+H], 752, 614, 572, 406, 167, 148; HRMS calcd for $C_{43}H_{45}N_3O_7S_2$ [M⁺+H] 780.2777, Found: 780.2764.

Scheme A, step d: [4S-[4α-7α(R*), 12bβ]]-7-[(1-Oxo-2(S)-(4-thiomorpholino-1,1-dioxide)-acetylthio-3- phenylpropyl)amino]-1,2,3,4,6,7,8,12b -octahydro-6-onopyrido-[2,1-a]benzazepine-4-carboxylic acid•trifluoroacetate Dissolve [4S-[4α-7α(R*), 12bβ]]-7-[(1-Oxo-2(S)-(4-thiomorpholino-1,1-dioxide)-acetylthio-3-phenylpropyl)amino]-1,2,3,4,6,7,8,12b-octahydro-6-oxopyrido[ 2,1a][2]benzazepine4-carboxylic acid, diphenylmethyl ester (1.45 g, 1.86 mmol) and anisole (1.5 mL, excess) in methylene chloride (20 mL). Add trifluoroacetic acid (3 mL) and stir at room temperature for 2.5 hours. Evaporate the solvent in vacuo and triturate with hexane (4×). Take the residue up in a minimal amount of methylene chloride and precipitate from hexane (3×) to give the title compound as a beige powder (1.29 g, 95%).

IR (CHCl₃) 3370, 3365, 3032, 2953, 1782, 1759, 1653, 1495, 1443, 1325, 1308, 1170, 1128 cm⁻¹; ¹H NMR (CDCl₃) 67 7.71 (d, 1, J=6.6 Hz), 6.91–7.39 (m, 9), 5.67 (m, 1), 5.45 (m, 1), 5.13 (m, 1), 4.36 (dd, 1, J=6.6, 8.4 Hz), 3.29–3.60 (m, 4), 2.97–3.29 (m, 9), 2.82 (dd, 1, J=12.9, 17.1 Hz), 2.44–2.60 (m, 1), 2.27–2.44 (m, 1), 1.67–2.09 (m, 4); ¹⁹F NMR (CDCl₃) δ−76.3; ¹³C NMR (CDCl₃) δ197.6, 174.4, 172.1, 170.8, 136.7, 136.1, 135.1, 130.6, 129.2, 128.6, 127.7, 127.2, 125.8, 125.0, 64.9, 51.3, 51.2, 48.9, 48.4, 36.8, 36.4, 25.0, 24.9, 17.0; MS (FAB) m/z 614 [M⁺+H], 596, 568.

Anal. Calcd for $C_{30}H_{35}N_3S_2 \cdot CF_3CO_2H$: C, 52.81; H, 4.99; N, 5.77; Found: C, 53.09; H, 5.29; N, 5.77.

EXAMPLE 15

[4S-[4α-7α(R*), 12bβ]]-7-[(1-Oxo-2(S)-(diethylamino)-acetylthio-3-phenylpropyl)amino]-1,2,3,4,6,7,8,12b-hexahydro-6-oxopyrido[2,1-a][2]benzazepine-4-carboxylic acid•trifluoroacetate

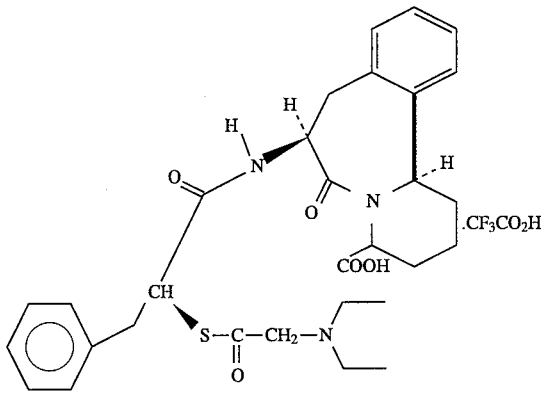

Scheme C, step d: [4S-[4α-7α(R*), 12bβ]]-7-[(1-Oxo- 2(S)-diethylamino)-acetylthio-3,phenylpropyl)amino]-1,2,3,4,6,7,8,12b-octahydro-6-oxopyrido[2,1-a][2]benzazepine-4-carboxylic acid, diphenylmethyl ester Dissolve t-butyl bromoacetate (1 eq) in tetrahydrofuran and add diethylamine (2.2 eq) via syringe. Stir the reaction mixture at room temperature for 2 hours, filter and wash the filter cake with ethyl acetate. Combine the organic filtrates and wash with saturated sodium bicarbonate (2×), water (2×) and brine. Dry (Na$_2$SO$_4$), filter and evaporate the solvent in vacuo. Take up the oily residue in ethyl acetate, cool in ice and bubble hydrogen chloride gas into the solution. Stir at room temperature overnight, cool and filter to give diethylaminoacetic acid hydrochloride salt as an oil (88%); $^1$H NMR (D$_2$O) δ3.86 (s, 2), 3.17 (q, 4, J=9 Hz), 1.17 (t, 6, J=9 Hz).

Suspend diethylaminoacetic acid hydrochloride salt (4.9 mmol) in degassed dimethylformamide (40 mL) and add carbonyldiimidazole (0.477 g, 2.94 mmol). Stir the reaction mixture at room temperature for 1.5 hours. Add a solution of [4S-[4α-7α(R*), 12bβ]]-7-[(1-Oxo-2(S)-thio-3-phenylpropyl)amino]-1,2,3,4,6,7,8,12b-octahydro-6-oxopyrido[2,1-a][2benzazepine-4-carboxylic acid, diphenylmethyl ester (2.45 mmol) in degassed tetrahydrofuran and stir at room temperature overnight. Dilute with ethyl acetate, wash with water (2×) and brine, dry (MgSO$_4$) and evaporate the solvent in vacuo to give the title compound (77%).

$^1$H NMR (CDCl$_3$) δ7.43, (d, 1, J=6 Hz), 7.16–7.35 (m, 12), 6.90–7.30 (m, 6), 6.59 (m, 1), 6.27 (s, 1), 6.19 (m, 1), 5.33–5.43 (m, 2), 4.28 (t, 1, J=7.5 Hz), 3.25–3.42 (m, 3), 2.87–3.08 (m, 2), 2.31–2.70 (m, 7), 1.54–2.02 (m, 4). 1.07 (t, 6, J=9 Hz); MS (CI, 70 eV) m/z 718 [M$^+$+H], 622, 605.

Scheme A, step d: [4s-[4α-7α(R*), 12bβ]]-7-[(1-Oxo- 2(S)-(diethylamino)-acetylthio-3-phenylpropyl)amino]-1,2,3,4,6,7,8,12b-octahydro-6-oxopyrido[2,1-a][2]benzazepine-4-carboxylic acid•trifluoroacetate Dissolve [4S-[4α-7α(R*), 12bβ]]-7-[(1-Oxo-2(S)-(diethylamino)-acetylthio- 3-phenylpropyl)amino]-1,2,3,4, 6,7,8,12b-octahydro-6-oxopyrido[2,1-a][2]benzazepine-4-carboxylic acid, diphenylmethyl ester(1.86 mmol) and anisole (1.5 mL, excess) in methylene chloride (20 mL), cool to −50° C. and add trifluoroacetic acid (3 mL). Stir the reaction mixture at −50° C. for 2.5 hours, evaporate the solvent in vacuo and triturate with hexane (4×). Take up the residue in a minimal amount of methylene chloride and precipitate from hexane (3×) to give the title compound (59%).

$^1$H NMR (CDCl$_3$) δ7.85 (d, 1, J=9 Hz), 6.90–7.35 (m, 9), 5.64–5.80 (m, 1), 5.39–5.51 (m, 1), 5.08–5.18 (m, 1), 4.61 (dd, 1, J=6, 10.5 Hz), 3.8–7–4.06 (m, 2), 3.32–3.48 (m, 2), 2.81–3.24 (m, 6), 2.28–2.56 (m, 2), 1.62–2.03 (m, 4), 1.18 (t, 6, J=7.5 Hz); $^{19}$F NMR (CDCl$_3$) δ−76.3; MS (CI, 70 eV) m/z 552 M$^+$+H], 439.

EXAMPLE 16

[4S-[4α-7α(R*), 12bβ]]-7-[(1-Oxo-2(S)-(diethylamino)-acetylthio-3-phenypropyl)amino]-1,2,3,4,6,7,8,12b-hexahydro-6-oxo-1H-[1,4]-oxazino[3,4-a][2]benzazepine-4-carboxylic acid•trifluoroacetate

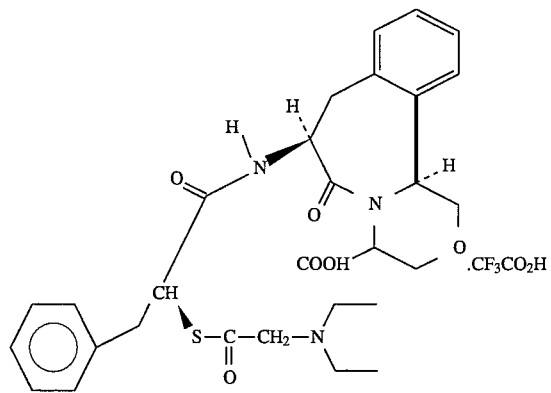

Scheme A, step c: [4S-[4α-7α(R*), 12bβ]]-7-[(1-Oxo- 2(S)-(diethylamino)-acetylthio-3-phenylpropyl)amino]-1,2,3,4,6,7,8,12b-octahydro-6-oxo-1H-[1,4]-oxazino[3,4-a][2]benzazepine-4-carboxylic acid, diphenylmethyl ester Suspend sodium hydride (175 mg of a 60% suspension, 4.0 mmol) in anhydrous dimethylformamide (4 mL) and place under a nitrogen atmosphere. Bubble hydrogen sulfide gas into the suspension until solution occurs. Add triphenylmethyl diethylaminethiolacetate (4.0 mmol) and heat gently for 1.5 hours while bubbling nitrogen through the solution to facilitate removal of excess hydrogen sulfide gas. Add 4S-[4α-7α(R*), 12bβ]]-7-[(1-Oxo-2(R)-bromo-3-phenylpropyl)amino]-1,2,3,4,6,7,8,12b-octahydro-6-oxo-1H-[1,4]-oxazino[3,4-a][2]benzazepine-4-carboxylic acid, diphenylmethyl ester (2.0 mmol) and stir for 2 hours. Pour into water, extract into ethyl acetate, wash with brine and dry (MgSO$_4$). Evaporate the solvent in vacuo and purify by chromatography to give the title compound.

Scheme A, step d: [4S-[4α-7α(R*), 12bβ]]-7-[(1-Oxo- 2(S)-(diethylamino)-acetylthio-3-phenylpropyl)amino]-1,2,3,4,6,7,8,12b-octahydro-6-oxo-1H-[1,4]-oxazino[3,4-a]2]benzazepine-4-carboxylic acid•trifluoroacetate Mix [4S-[4α-7α(R*), 12bβ]]-7-[(1-oxo-2(S)-(diethylamino)-acetylthio- 3-phenylpropyl)amino]-1,2,3,4, 6,7,8,12b-octahydro-6-oxo-1H-[1,4]-oxazino[3,4-a][2] benzazepine-4-carboxylic acid, diphenylmethyl ester (2.0 mmol), anisole (0.5 mL) and methylene chloride (6 mL). Place under a nitrogen atmosphere and cool to −50° C. Add trifluoroacetic acid (3.0 mL) over 1 minute and allow to warm to room temperature over 2 hours while stirring. Evaporate the solvent in vacuo triturate with hexane and methylene chloride and dry under high vacuum to give the title compound.

EXAMPLE 17

[4S-[4α-7α(R*), 12bβ]]-7-[(1-Oxo-2(S)-(diethylamino)-acetylthio-3-phenylpropyl)amino]-1,2,3,4,6,7,8,12b-hexahydro-6-oxo-1H-[1,4]-thiazino[3,4-a][2]benezazepine-4-carboxylic acid•trifluoroacetate

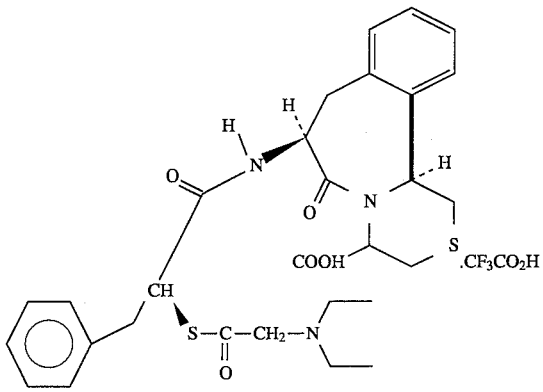

Scheme A, step c: [4S-[4α-7α(R*), 12bβ]]-7-[(1-Oxo-2(S-)(diethylamino-acetylthio-3-phenylpropyl)amino]-1,2,3,4,6,7,8,12b-octahydro-6-oxo-1H-[1,4]-thiazino-[3,4-a][2]benzazepine-4-carboxylic acid, diphenylmethyl ester Suspend sodium hydride (175 mg of a 60% suspension, 4.0 mmol) in anhydrous dimethylformamide (4 mL) and place under a nitrogen atmosphere. Bubble hydrogen sulfide gas into the suspension until solution occurs. Add triphenylmethyl diethylaminethiolacetate (4.0 mmol) and heat gently for 1.5 hours while bubbling nitrogen through the solution to facilitate removal of excess hydrogen sulfide gas. Add [4S-[4α-7α(R*), 12bβ]]-7-[(1-oxo-2(R)-bromo-3-phenylpropyl)amino]-1,2,3,4,6,7,8,12b-octahydro-6-oxo-1H-[1,4]-thiazino[3,4-a][2]benzazepine-4-carboxylic acid, diphenylmethyl ester (2.0 mmol) and stir for 2 hours. Pour into water, extract in to ethyl acetate, wash with brine and dry (MgSO₄). Evaporate the solvent in vacuo and purify by chromatography to give the title compound.

Scheme A, step d:[4S-4α-7α(R*), 12bβ]]-7-[(1-Oxo-2(S)-(diethylamino)-acetylthio-3-phenylpropyl)amino]-1,2,3,4,6,7,8,12b-octahydro-6-oxo-1H-[1,4]-thiazino-[3,4-a][2]benzazepine-4-carboxylic acid•trifluoroacetate Mix [4S-[4α-7α(R*), 12bβ]]-7-[(1-oxo-2(S)-(diethylamino)-acetylthio- 3-phenylpropyl)amino]-1,2,3,4,6,7,8,12b-octahydro- 6-oxo-1H-[1,4]-thiazino[3,4-a][2]benzazepine-4-carboxylic acid, diphenylmethyl ester (2.0 mmol), anisole (0.5 mL) and methylene chloride (6 mL). Place under a nitrogen atmosphere and cool to –50° C. Add trifluoroacetic acid (3.0 mL) over 1 minute and allow to warm to room temperature over 2 hours while stirring. Evaporate the solvent in vacuo, triturate with hexane and methylene chloride and dry under high vacuum to give the title compound.

EXAMPLE 18

[4S-[4α-7α(R*), 12bβ]]-7-[(1-Oxo-2(S)-(4-methyl-1,4-piperazino)-acetylthio-3-phenylpropyl)amino]-1,2,3,4,6,7,8,12b-octahydro-6-oxopyrido[2,1-a][2]-benzazepine-4-carboxylic acid•trifluoroacetate

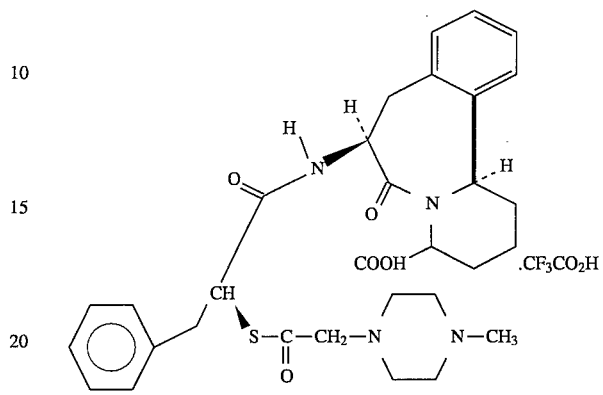

Scheme C, step d: [4S-[4α-7α(R*), 12bβ]]-7-[(1-Oxo-2(S)-(4-methyl-1,4-piperazino)-acetylthio-3-phenylpropyl)amino]-1,2,3,4,6,7,8,12b-octahydro-6-oxopyrido[2,1-a][2]benzazepine-4-carboxylic acid, diphenylmethyl ester Dissolve N-methylpiperazine (5.0 mL, 45.09 mmol) in diethyl ether in a stoppered flask and treat with neat ethyl bromoacetate (3.012 g, 18.036 mmol). Stir the reaction mixture at room temperature overnight, filter and wash the filter cake with diethyl ether. Combine the organic filtrates and evaporate the solvent in vacuo to give a light yellow oil. Take up in water (60 mL) and heat at 95° C. for 4 hours, allow to cool to room temperature and stir overnight. Evaporate the solvent in vacuo and dissolve the residue in acetonitrile and evaporate the solvent in vacuo (twice) to azeotrope residual water. Dissolve in a minimal amount of methanol, dilute with diethyl ether and place in the freezer. Isolate the crystals which form by decanting the supernatant and wash with diethyl ether. Obtain two more crops of crystals from the mother liquor to give 4-methylpiperazine-1-acetic acid (2.345 g, 82%); mp 158°–160° C. (lit 159.5°–161° C.), $^1$H NMR ($D_2O$) δ3.98 (s, 2), 3.81–3.32 (m, 8), 2.89 (s, 3).

Suspend 4-methylpiperazine-1-acetic acid (4.9 mmol) in degassed dimethylformamide (40 mL) and add carbonyldiimidazole (0.477 g, 2.94 mmol). Stir the reaction mixture at room temperature for 1.5 hours. Add a solution of [4S-[4α-7α(R*), 12bβ]]-7-[(1-Oxo-2(S)-thio-3-phenylpropyl)amino]-1,2,3,4,6,7,8,12b-octahydro-6-oxopyrido[ 2,1-a][2]benzazepine-4-carboxylic acid, diphenylmethyl ester (2.45 mmol) in degassed tetrahydrofuran and stir at room temperature overnight. Dilute with ethyl acetate, wash with water (2×) and brine, dry (MgSO₄) and evaporate the solvent in vacuo to give the title compound (90%).

$^1$H NMR ($CDCl_3$) δ7.41, (d, 1, J=6.7 Hz), 7.33–6.92 (m, 17), 6.61 (m, 1), 6.27 (s, 1), 5.56 (quint, 1, J=6.3 Hz), 5.37 (m, 2), 4.29 (t, 1, J=7.6 Hz), 3.41–3.22 (m, 4), 3.02 (dd, 1, J=7.8, 13.8 Hz), 2.66–2.34 (m, 10), 2.32 (s, 3), 2.03–1.66 (m, 6) $^{13}$C NMR ($CDCl_3$) δ171.67, 169.76, 169.68, 158.79, 141.38, 139.92, 139.77, 139.71, 139.01, 136.48, 135.38, 130.75, 130.21, 129.00, 128.25, 128.16, 127.76, 127.71, 127.31, 126.94, 126.86, 126.80, 125.35, 124.63, 124.12, 123.78, 123.02, 122.14, 114.00, 78.22, 55.20, 53.40, 51.05, 51.02, 49.95, 48.43, 36.79, 35.74, 33.41, 25.02, 24.91, 17.12; MS (CI/CH$_4$) m/z 745 [M$^+$+H, base peak], 605, 572, 405, 203, 187, 175, 159, 113.

Scheme A, step d: [4S-[4α-7α(R*), 12bβ]]-7-[(1-Oxo-2(S)-(4-methyl-1,4-piperazino)-acetylthio-3-phenylpropyl)amino]-1,2,3,4,6,7,8,12b-octahydro-6-oxopyrido[2,1-a]]2]benzazepine-4-carboxylic acid•trifluoroacetate Dissolve [4S-[4α-7α(R*), 12bβ]]-7-[(1-Oxo-2(S)-(4-methyl-1,4-piperazino)-acetylthio-3-phenylpropyl)amino]-1,2,3,4,6,7,8,12b-octahydro-6-oxopyrido[2,1-a][2]benzazepine-4-carboxylic acid, diphenylmethyl ester (500 mg, 0.690 mmol) and anisole (0.5 mL) in methylene chloride (15 mL). Add trifluoroacetic acid (1.0 mL) and stir at room temperature for 2 hours. Evaporate the volatiles under a stream of nitrogen at ca. 35° C. Dissolve the residue in methylene chloride and evaporate again in the same way. Take the material up in methylene chloride and dilute with ca. 4 volumes of diethyl ether. Allow the resulting precipitate to settle overnight, decant the supernatant and wash the solid 4 times with diethyl ether, decanting the supernatant each time. Dry, first in air and then under high vacuum to give the title compound (382 mg, 69%).

$^1$H NMR (CDCl$_3$) δ7.56 (d, 1, J=8.6 Hz), 7.37–6.98 (m, 7), 5.51 (m, 1), 5.38 (m, 1), 5.04 (m, 1), 4.33 (t, 1, J=8.4 Hz), 3.55 (dd, 1, J=6.2, 16.9 Hz), 3.49–3.25 (m, 3), 3.02 (dd, 1, J=9.3, 13.8 Hz), 2.94–2.79 (m, 8), 2.67 (s, 3), 2.59–2.30 (m, 2), 2.01–1.70 (m, 6); $^{13}$C NMR (CDCl$_3$) δ 196.49, 173.44, 171.94, 170.13, 136.88, 136.28, 135.72, 130.51, 129.33, 129.18, 128.53, 128.46, 127.52, 127.17, 125.82, 125.14, 64.56, 53.07, 51.90, 51.31, 49.54, 49.49, 48.87, 48.18, 43.26, 36.67, 36.32, 25.18, 25.13, 17.13; $^{19}$F NMR (CDCl$_3$) δ–76.1; MS (CI/CH$_4$) m/z 579 [M$^+$+H], 517, 439, 406, 377, 343, 296, 257, 199, 187, 175, 159 (base peak), 115.

Anal. Calcd for C$_{31}$H$_{38}$N$_4$O$_5$S•CF$_3$CO$_2$H: C, 57.22; H, 5.67; N, 8.09; Found: C, 57.15; H, 5.83, N, 7.73.

EXAMPLE 19

[4S-[4α-7α(R*), 12bβ]]-7-[(1-Oxo-2(S)-(1-imidazolino)-acetylthio-3-phenpylpropyl)amino]-1,2,3,4,6,7,8,12b-octahydro-6-oxopyrido[2,1-a][2]benzazepine-4-carboxylic acid•trifluoroacetate

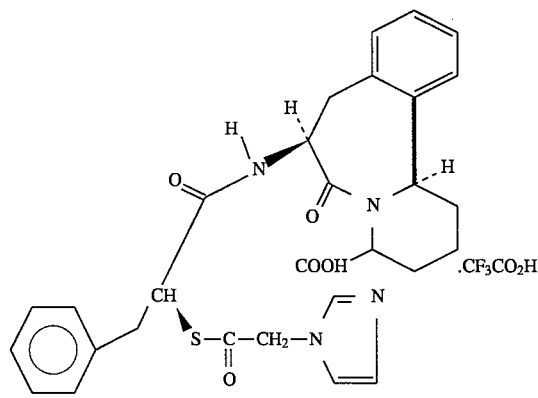

Scheme C, Step d: [4S-[4α-7α(R*), 12bβ]]-7-[(1-Oxo-2(S)-( 1-imidazolino)-acetyithio-3-phenylpropyl)amino]-1,2,3,4,6,7,8,12b-octahydro-6-oxopyrido[2,1-a][2]benzazepine-4-carboxylic acid, diphenylmethyl ester Dissolve t-butyl bromoacetate (1 eq) in tetrahydrofuran and add imidazole (2.2 eq). Stir the reaction mixture at room temperature for 2 hours, filter and wash the filter cake with ethyl acetate. Combine the organic filtrates and wash with saturated sodium bicarbonate (2×), water (2×) and brine. Dry (Na$_2$SO$_4$), filter and evaporate the solvent in vacuo. Take up the oily residue in ethyl acetate, cool in ice and bubble hydrogen chloride gas into the solution. Stir at room temperature overnight, cool and filter to give 1-imidazolinoacetic acid hydrochloride salt (57%); mp 195°–205° C. (dec) (lit 193°–195° C., EtOH); $^1$H NMR (D$_2$O) δ8.66 (s, 1), 7.37 (d, 2, J=3.9 Hz), 4.99 (s, 2).

Suspend 1-imidazolinoacetic acid hydrochloride salt (4.9 mmol) in degassed dimethylformamide (40 mL) and add carbonyldiimidazole (0.477 g, 2.94 mmol). Stir the reaction mixture at room temperature for 1.5 hours. Add a solution of [4S-[4α-7α(R*), 12bβ]]-7-[(1-Oxo-2(S)-thio-3-phenylpropyl)amino] -1,2,3,4,6,7,8,12b-octahydro-6-oxopyrido[ 2,1-a][2]benzazepine-4-carboxylic acid, diphenylmethyl ester (2.45 mmol) in degassed tetrahydrofuran and stir at room temperature overnight. Dilute with ethyl acetate, wash with water (2×) and brine, dry (MgSO$_4$) and evaporate the solve it in vacuo to give the title compound (99%).

$^1$H NMR (CDCl$_3$) δ7.52(s, 1), 7.42 (d, 1, J=8.1 Hz), 7.34–6.91 (m, 19), 6.66 (m, 1), 6.32 (s, 1), 5.54 (quint, 1, J=6.9 Hz), 5.36 (m, 2), 4.82 (s, 2, 4.37 (t, 1, J=8.4 Hz), 3.38–3.28 (m, 2), 3.03 (dd, 1, J=8.9, 13.8 Hz), 2.54 (dd, 1, J=13.1 , 16.9 Hz), 2.97–2.86 (m, 2), 2.03–1.68 (m, 5); $^{13}$C NMR CDCl$_3$) 193.80, 171.56, 169.55, 168.35, 139.88, 139.01, 138,23, 136.80, 136.35, 135.31, 130.76, 130.18, 129.23, 128.51, 128.31, 128.25, 127.82, 127.77, 127.43, 127.15, 126.99, 126.84, 125.51, 124.69, 120.21, 78.26, 55.23, 51.16, 51.08, 49.08, 48.58, 37.05, 36.54, 25.02, 24.94, 17.13; MS (CI/CH$_4$) m/z 713 [M$^+$+H], 605, 545, 501, 437, 406, 393, 359, 257, 217, 184, 167 (base peak), 155, 127.

Scheme A, step d: [4S-4α-7α(R*), 12bβ]]-7-[(1-Oxo-2(S)-(1-imidazolino)-acetylthio-3-phenylpropyl)amino]-1,2,3,4,6,7,8,12b-octahydro-6-oxopyrido-[2,1-a][2]benzazepine-4-carboxylic acid•trifluoroacetate Dissolve [4S-[4α-7α(R*), 12bβ]]-7-[(1-Oxo-2(S)-(1-imidazolino)-acetylthio- 3-phenylpropyl)amino]-1,2,3,4, 6,7,8,12b-octahydro-6-oxopyrido[2,1-a][2]benzazepine-4-carboxylic acid, diphenylmethyl ester (685 mg, 0.962 mmol) and anisole (0.5 mL) in methylene chloride (15 mL). Add trifluoroacetic acid (1.0 mL) and stir at room temperature for 2 hours. Evaporate the volatiles under a stream of nitrogen at ca. 35° C. Dissolve the residue in methylene chloride and evaporate again in the same way. Take the material up in methylene chloride and dilute with ca. 4 volumes of diethyl ether. Allow the resulting precipitate to settle overnight, decant the supernatant and wash the solid 4 times with diethyl ether, decanting the supernatant each time. Dry, first in air and them under high vacuum to give the title compound as a white powder (518 mg, 82%).

$^1$H NMR (CDCl$_3$) δ8.67 (br s, 1), 7.59 (br s, 1), 7.33–6.99 (m, 10), 5.55 (m, 1), 5.38 (m, 1), 5.11 (br d, 1, J=18.4 Hz), 4.99 (br d, 1, J=18.4 Hz), 4.94 (m, 1), 4.47 (br t, 1, J=8.1 Hz), 3.44–3.30 (m, 2), 3.06 (br dd, 1, J=10.8, 14.5 Hz), 2.81 (m, 1), 2.49 (m, 1), 2.28 (m, 1), 2.01–1.68 (m, 5); $^{13}$C NMR (CDCl$_3$) δ198.44, 172.87, 171.71, 169.62, 137.50, 136.78, 136.20, 130.40, 129.21, 128.43, 127.28, 126.94, 125.68, 125.18, 65.60, 53.49, 52.12, 51.43, 49.74, 48.80, 47.65, 43.06, 36.71, 36.69, 25.34, 17.34,; $^{19}$F NMR (CDCl$_3$) δ–75.9; MS (CI/CH$_4$) m/z 547 [M$^+$+H],529, 485, 449, 439, 421, 405, 377, 376, 343, 301, 274, 239, 227, 167, 155, 127, 115 (base peak).

EXAMPLE 20

[4S-[4α-7α(R*), 12bβ]]-7-[(1-Oxo-2(S)-(4-dimethylaminobutyrylthio-3-phenylpropyl)amino]-1,2,3,4,6,7,8,12b-octahydro-6-oxopyrido[2,1-a][2]benzazepine-4-carboxylic acid•trifluoroacetate

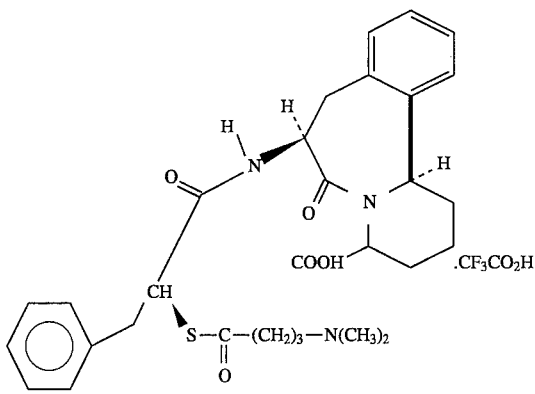

Suspend 4-dimethylaminobutyric acid (4.9 mmol) in degassed dimethylformamide (40 mL) and add carbonyldiimidazole (0.477 g, 2.94 mmol). Stir the reaction mixture for 1.5 hours. Add a solution off [4S-[4α-7α(R*), 12bβ]]-7-[(1Oxo-2-(S)-thio-3-phenylpropyl)amino]-1,2,3,4,6,7,8,12b-octahydro-6-oxopyrido[2,1-a]8 2]benzazepine-4-carboxylic acid, diphenylmethyl (2.45 mmol) in degassed tetrahydrofuran and stir at room temperature overnight. Dilute with ethyl acetate, wash with water (2×) and brine, dry (MgSO$_4$) and evaporate the solvent in vacuo. Purify by silica gel chromatography (hexane:ethyl acetate/1:1 to 3:7) to give the title compound (60%).

IR (KBr) 3384, 3062, 3030, 2942, 2868, 1735, 1680, 1651, 1495, 1438, 1421, 1199, 1185, 1154, 748 cm$^{-1}$; $^1$H NMR (CDCl$_3$) δ7.44, (d, 1, J=6.3 Hz), 7.15–7.36 (m, 12), 6.87–7.13 (m, 6), 6.62 (m, 1) 6.28 (s, 1), 5.57 (m, 1), 5.31–5.43 (m, 2), 4.38 (t, 1J=7.5 Hz), 3.29–3.44 (m, 2), 3.05 (dd, 1, J=10.5, 14.1 Hz), 2.65 (t, 2, J=7.8 Hz), 2.54 (dd, 1, J=12, 18 Hz), 2.43 (m, 2), 2.29 (t, 2, J=7.2 Hz), 2.21 (s, 6), 1.63–2.02 (m, 6); $^{13}$C NMR (CDCl$_3$) δ197.9, 171.6, 169.7, 169.4, 140.0, 139.1, 137.5, 136.6, 135.4, 130.8, 129.3, 128.4, 128.3, 128.2, 127.8, 127.7, 127.4, 127.0, 126.9, 125.4, 124.7, 78.2, 58.2, 51.1, 51.0, 48.5, 48.0, 45.1, 41.7, 36.9, 36.5, 25.0, 24.9, 23.2, 17.1; MS (FAB) m/z 718[M$^+$+H], 267,167; HRMS calcd for C$_{43}$H$_{48}$N$_3$O$_5$S [M$^+$+H]: 718.3315, Found: 718.3317.

Scheme A, step d: [4S-[4α-7α(R*), 12bβ]]-7-[(1-Oxo-2(S)-(4-dimethylaminobutyrylthio)-acetylthio-3-phenylpropyl)amino]-1,2,3,4,6,7,8,12b-octahydro-6-oxopyrido[2,1-a][21benzazepine-4-carboxylic acid, trifluoroacetate salt Dissolve [4S-[4α-7α(R*), 12bβ]]-7-[(1-Oxo-2(S)-( 4-dimethylaminobutyrylthio)-3-phenylpropyl)amino]-1,2, 3,4,6,7,8,12b-octahydro-6-oxopyrido[2,1-a][2]benzazepine-4-carboxylic acid, diphenylmethyl ester (1.86 mmol) and anisole (1.5 mL, excess) in methylene chloride (20 mL) and add trifluoroacetic acid (3 mL). Stir the reaction mixture for 2.5 hours, evaporate the solvent vacuo and triturate with hexane (4×). Take up the residue in a minimal amount of methylene chloride and precipitate from hexane (3×) to give the title compound (79%).

IR (KBr) 3394, 3061, 3030, 2951, 1731, 1678, 1651, 1495, 1441, 1199, 1141 cm$^{-1}$; $^1$H NMR (CDCl$_3$) δ10.68 (br s, 1) 7.59 (m, 1), 6.89–7.60 (m, 9), 5.58 (m, 1), 5.42 (m, 1), 5.02 (s, 1), 4.39 (m, 1), 3.26–3.67 (m, 2), 2.88–3.22 (m, 3), 2.20–2.88 (m, 11), 1.54–2.19 (m, 6); $^{19}$F NMR (CDCl$_3$) δ–76.2; $^{13}$C NMR (CDCl$_3$) δ197.2, 173.1, 172.0, 169.5, 137.2, 136.4, 130.5, 129.3, 128.5, 127.5, 127.1, 125.8, 125.1, 56.3, 51.9, 51.2, 48.8, 48.2, 43.0, 42.6, 39.8, 36.4, 36.1, 25.3, 25.2, 19.8, 17.1; MS (FAB) m/z 552 [M$^+$+H].

EXAMPLE 21

[4S-[4α-7α(R*), 12bβ]]-7-[(1-Oxo-2(S)-(1-pyrrolidino)-acetylthio-3-phenylpropyl)amino]-1,2,3,4,6,7,8,12b-octahydro-6-oxopyrido[2,1-a][2]benzazepine-4-carboxylic acid•trifluoroacetate

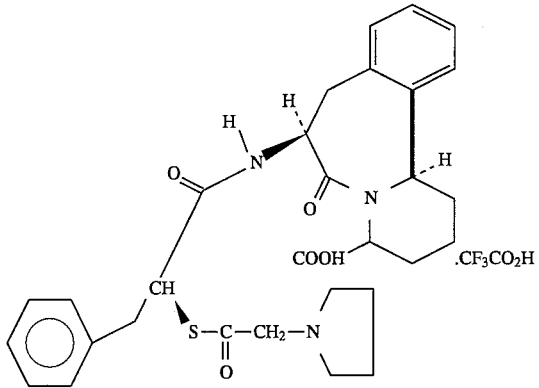

Scheme C, step d: [4S-[4α-7α(R*), 12bβ]]-7-[(1-Oxo-2(S)-( 1-pyrrolidino)-acetylthio-3-phenylpropyl)amino]-1,2,3,4,6,7,8,12b-octahydro-6-oxopyrido[2,1-a][2]benzazepine-4-carboxylic acid, diphenylmethyl ester Dissolve t-butyl bromoacetate (1 eq) in tetrahydrofuran and add pyrrolidine (2.2 eq) via syringe. Stir the reaction mixture at room temperature for 2 hours, filter and wash the filter cake with ethyl acetate. Combine the organic filtrates and wash with saturated sodium bicarbonate (2×), water (2×) and brine. Dry (Na$_2$SO$_4$), filter and evaporate the solvent in vacuo. Take up the oily residue in ethyl acetate, cool in ice and bubble hydrogen chloride gas into the solution. Stir at room temperature overnight, cool and filter to give 1-pyrrolidinoacetic acid (86%); mp 188°–190° C.; $^1$H NMR (D$_2$O) δ3.93 (s, 2), 3.50–3.64 (m, 2), 2.97–3.0 4 (m, 2), 1.74–2.03 (m, 4).

Suspend 1-pyrrolidinoacetic acid (4.9 mmol) in degassed dimethylformamide (40 mL) and add carbonyldiimidazole (0.477 g, 2.94 mmol). Stir the reaction mixture at room temperature for 1.5 hours. Add a solution of [4S-[4α-7α(R*), 12bβ]]-7-[(1-Oxo-2(S)-thio-3-phenylpropyl)amino]-1,2,3,4,6,7,8,12b-octahydro-6- oxopyrido[2,1-α][2]benzazepine-4-carboxylic acid, diphenylmethyl ester (2.45 mmol) in degassed tetrahydrofuran and stir at room temperature overnight. Dilute with ethyl acetate, wash with water (2×) and brine, dry (MgSO$_4$) and evaporate the solvent in vacuo to give the title compound (60%).

$^1$H NMR (CDCl$_3$) δ7.42 (d, 1, J=7.5 Hz), 7.16–7.38 (m, 12), 6.90–7.12 (m, 6), 6.59 (m, 1), 6.26 (s, 1), 5.56 (m, 1), 5.32–5.42 (m, 2), 4.31 (t, 1, J=7.5 Hz), 3.28–3.45 (m, 4), 3.03 (dd, 1, J=7.5, 12 Hz), 3.60–3.76 (m, 4), 2.32–2.69 (m, 9), 1.57–2.02 (m, 10).

Scheme A, step d: [4S-[4α-7α(R*), 12bβ]]-7-[(1-Oxo-2(S)-(1-pyrrolidino)-acetylthio-3-phenylpropyl)amino]-1,2,3,4,6,7,8,12b-octahydro-6-oxopyrido[2,1-a ][2]benzazepine-4-carboxylic acid, trifluoroacetate salt Dissolve [4S-[4α-7α(R*), 12bβ]]-7-[(1-Oxo-2(S)-(1-pyrrolidion)-acetylthio-3-phenylpropul)amino]-1,2,3,4,6,7,8,12b-octahydro-6-oxopyrido[2,1-a][2]benzazepine-4-carboxylic acid, diphenylmethyl ester (1.86 mmol) and anisole (1.5 mL, excess) in methylene chloride (20 mL), cool to −50° C. and add trifluoroacetic acid (3 mL). Stir the reaction mixture at −50° C. for 2.5 hours, evaporate the solvent in vacuo and triturate with hexane (4×). Take up the residue in a minimal amount of methylene chloride and precipitate from hexane (3×) to give the title compound (86%).

$^1$H NMR (CDCl$_{13}$) δ7.85 (d, 1, J=7.5 Hz), 6.87–7.39 (m, 9), 5.65–5.80 (m, 1), 5.38–5.49 (m, 1), 4.98–5.11 (m, 1), 4.63 (dd, 1, J=7.5, 9 Hz), 3.95–4.11 (m, 2), 3.29–3.48 (m, 4), 2.76–3.11 (m, 4), 2.23–2.54 (m, 2), 1.59–2.09 (m, 8); $^{19}$F NMR (CDCl$_3$) δ−76.1; $^{13}$C NMR (CDCl$_3$) 67 190.5, 172.8, 172.1, 168.6, 136.6, 136.5, 135.7, 130.6, 129.4, 128.5, 127.3, 127.2, 125.7, 125.0, 55.9, 51.5, 51.1, 49.5, 48.8, 37.2, 36.6, 25.4, 25.2, 17.2; MS (FAB) m/z 550 [M$^+$+H].

EXAMPLE 22

[4S-[4α-7α(R*), 12bβ]]-7-[(1-Oxo-2(S)-3-pyridinylacetylthio-3-phenylpropyl)amino]——1,2,3,4,6,7,8,12b-octahydro-6-oxopyrido[2,1-a][2]benzazepine-4-carboxylic acid•trifluoroacetate

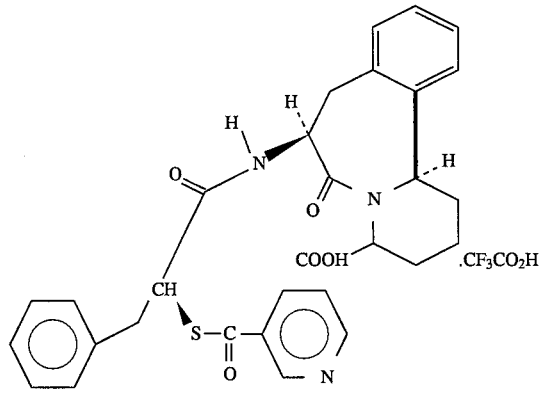

Suspend [4S-[4α-7α(R*), 12bβ]]-7-[(1-Oxo-2(S)-thio-3-phenylpropyl) amino]-1,2,3,4,6,7,8,12b-octahydro-6-oxopyrido[2,1-a][2]benzazepine-4-carboxylic acid, diphenylmethyl ester (1.20 g, 1.98 mmol) and nicotinic acid (0.244 g, 1.98 mmol) in methylene chloride (50 mL). Add EDCI (0.418 g, 2.18 mmol). Stir the reaction mixture at room temperature overnight. Dilute with methylene chloride, wash with saturated sodium bicarbonate, water, 0.5M hydrochloric acid , water and brine. Dry (MgSO$_4$) and evaporate the solvent in vacuo. Purify by silica gel chromatography (ethyl acetate) to give the title compound as a glassy solid (0.93 g, 63%). IR (KBr) 3430, 3062, 3031, 2943, 1736, 1656, 1584, 1495, 1438, 1419, 1219, 1155, 912 cm$^{-1}$; $^1$H NMR (CDCl$_3$) δ9.21 (d, 1, J=1.8 Hz), 8.82 (dd, 1, J=1.8, 5.1 Hz), 8.23 (m, 1), 7.55 (d, 1, J=6.6 Hz), 7.42 (m, 1), 7.20–7.37 (m, 12), 6.83–7.20 (m, 6), 6.57 (m, 1), 6.24 (s, 1), 5.59 (m, 1), 5.32–5.43 (m, 2), 4.63 (t, 1, J=7.8 Hz), 3.46 (dd, 1, J=7.8, 14.4 Hz), 3.38 (dd, 1, J=6.3, 18 Hz), 3.18 (dd, 1, J=7.8, 14.4 Hz), 2.35–2.63 (m, 3), 1.59–2.07 (m, 4); $^{13}$C NMR (CDCl$_3$) δ189.8, 171.8, 170.0, 169.4, 154.5, 148.9, 140.1, 139.2, 137.5, 136.7, 135.5, 135.0, 132.1, 131.0, 129.5, 128.7, 128.5, 128.4, 127.9, 127.8, 127.6, 127.2, 127.1, 127.0, 125.6, 124.9, 123.8, 78.3, 51.0, 50.9, 48.5, 48.1, 36.8, 36.2, 24.8 16.9; MS (CI, 70 eV) m/z 710[M$^+$+H], 542, 498, 167, 140, 106; HRMS calcd for C$_{43}$H$_{40}$N$_3$O$_5$S: 710.2689, Found: 710.2680.

Scheme A. step d: [4S-[4α-7α(R*), 12bβ]]-7-[(1-Oxo-2(S)- 3-pyridinylactylthio-3-phenylpropyl)amino]-1,2,3,4,6,7,8,12b-octahydro-6-oxopyrido[2,1-a][2]benzazepine-4-carboxylic acid•trifluoroacetate Dissolve [4S-[4α-7α(R*), 12bβ]]-7-[(1-Oxo-2(S)-3-pyridinylacetylthio-3-phenylpropyl)amino]-1,2,3,4,6,7,8, 12b-octahydro-6-oxopyrido[2,1-a][2]benzazepine-4-carboxylic acid, diphenylmethyl ester (1.86 mmol) and anisole (1.5 mL, excess) in methylene chloride (20 mL) and add trifluoroacetic acid (3 mL). Stir the reaction mixture for 2.5 hours, evaporate the solvent in vacuo and triturate with hexane (4×). Take up the residue in a minimal amount of methylene chloride and precipitate from hexane (3×) to give the title compound (96%).

IR (KBr) 3394, 3064, 3033, 2950, 1729, 1669, 1517, 1496, 1444, 1190 cm$^{-1}$; $^1$H NMR (CDCl$_3$) δ9.14 (s, 1), 8.87 (dd, 1, J=1.2, 4.5 Hz), 8.5 (d, 1, J=3.9 Hz), 7.73 (m, 2), 6.79–7.46 (m, 9), 5.63 (m, 1) 5.43 (m, 1), 5.15 (m, 1), 4.66 (t, 1, J=7.5 Hz), 3.33–3.58 (m, 2), 3.17 (dd, 1, J=8.4, 14.1 Hz), 2.73–2.91 (m, 1), 2.24–2.58 (m, 1), 1.64–2.08 (m, 4); $^{19}$F NMR (CDCl$_3$) δ−76.−9; $^{3}$C NMR (CDCl$_3$) δ187.6, 173.9, 171.9, 169.2, 149.3, 144.5, 139.0, 136.6, 136.3, 135.3, 133.6, 130.5, 129.2, 128.6, 127.4, 127.3, 125.6, 125.5, 124.9, 51.1, 51.0, 49.2, 48.8, 36.9, 36.5, 25.0, 24.9, 17.1; MS (FAB) m/z 544 [M$^+$+H], 498; HRMS calcd for C$^{30}$H$_{30}$N$_3$O$_5$S [M$^+$+H]: 544.1906, Found: 544.1889.

5,488,048

EXAMPLE 23

4S-[4α-7α(R*), 12bβ]]-7-[(1-Oxo-2(S)-3-dimethylaminobenzoylthio-3-phenylpropyl)amino]-1,2,3,4,6,7,8,12b-octahydro-6-oxopyrido[2,1-a][2]benzazepine-4-carboxylic acid•trifluoroacetate

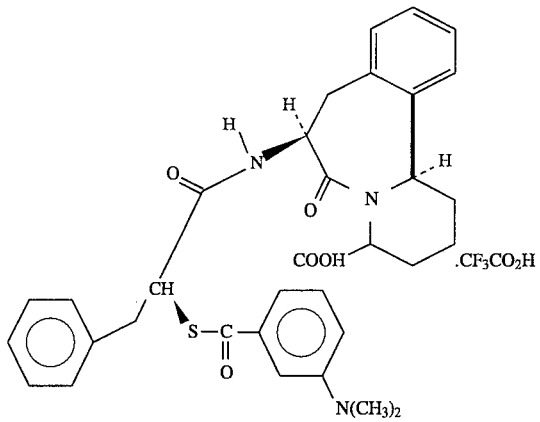

Scheme C, step d: [4S-[4α-7α(R*), 12bβ]]-7-[(1-Oxo-2(S)- 3-dimethylaminothio-3-phenylpropyl)amino]-1,2,3,4,6,7,8,12b-octahydro-6-oxopyrido[2,1-a][2]benzazepine-4-carboxylic acid, diphenylmethyl ester Dissolve 3-dimethylaminobenzoic acid (0.451 g, 2.73 mmol) and triethylamine (0.38 mL) in methylene chloride (50 mL) and cool to −20° C. Add 2-fluoro-1-methylpyridinium p-toluenesulfonate (0.773 g, 2.73 mmol). Stir the reaction mixture at −20° C. for 1 hour, add solid [4S-[4α-7α(R*), 12bβ]]-7-[(1-Oxo-2(S)-thio-3-phenylpropyl)amino]-1,2,3,4,6,7,8,12b-octahydro-6-oxopyrido[2,1-a][2]benzazepine-4-carboxylic acid, diphenylmethyl ester (1.5 g, 2.48 mmol) and triethylamine (0.38 mL, 2.73 mmol).

Remove the cooling bath and stir at room temperature for 2.5 hours, dilute with methylene chloride, wash with water (2×) and brine. Dry (MgSO$_4$), evaporate the solvent in vacuo and purify by silica gel chromatography (hexane/ethyl acetate: 7:3 to 6.5:3.5) to give the title compound (1.38 g, 70%).

IR (CHCl$_3$) 3385, 306, 3034, 3011, 2949, 1734, 1655, 1601, 1497, 1437, 1356, 1198, 1157, 922 cm$^{-1}$ $^1$H NMR (CDCl$_3$) δ7.58 (d, 1, J=9 Hz), 6.85–7.42 (m, 18), 6.48 (d, 1, J=12 Hz), 6.19 (s, 1), 5.58 (m, 1), 5.37 (m, 2), 4.59 (t, 1, J=7.5 Hz), 3.45 (dd, 1, J=9, 15 Hz), 3.34 (dd, 1, J=6, 16.5 Hz), 3.15 (dd, 1, J=7.5, 13.5 Hz), 2.98 (s, 6), 2.35–2.49 (m, 3), 1.63–2.02 (m, 4); $^{13}$C NMR (CDCl$_3$) δ191.5, 171.5, 169.8, 169.7, 150.5, 140.0, 139.0, 137.8, 137.1, 136.7, 135.3, 130.8, 129.3, 129.2, 128.4, 128.3, 128.2, 127.7, 127.6, 127.3, 126.9, 126.8, 125.3, 124.6, 117.5, 115.6, 110.4, 78.4, 51.0, 50.9, 48.5, 47.6, 40.4, 36.8, 36.2, 25.0, 17.1; MS (FAB) m/z 752 [M$^+$+H], 587, 167.

Anal. Calcd for C$_{46}$H$_{45}$N$_3$O$_5$S•0.3H$_2$O: C, 72.95; H, 6.07; N, 5.55; Found: C, 72.61, H, 6.07; N, 5.32.

Scheme A, step d; [4S-[4α-7α(R*), 12bβ]]-7-[(1-Oxo-2(S)-3-dimethylamithio-3-phenylpropyl)amino]-1,2,3,4,6,7,8,12b-octahydro-6-oxopyrido[2,1-a][2]benzazepine-4-carboxylic acid•trifluoroacetate Dissolve [4S-[4α-7α(R*), 12b β]]-7-[(1-Oxo-2(S)-3-dimethylaminobenzoylthio-3-phenylpropyl)amino]-1,2,3,4,6,7,8,12b-octahydro-6-oxopyrido[2,1-a][2]benzazepine-4-carboxylic acid, diphenylmethyl ester (1.86 mmol) and anizole (1.5 mL, excess) in methylene chloride (20 mL) and add trifluoroacetic acid (3 mL). Stir the reaction mixture for 2.5 hours, evaporate the solvent in vacuo and triturate with hexane (4×). Take up the residue in a minimal amount of methylene chloride and precipitate from hexane (3×) to give the title compound (94%).

IR (CDCl$_3$) 3374, 3065, 3032, 2953, 1780, 1759, 1721, 1657, 1601, 1497, 1441, 1233, 1169 cm$^{-1}$; $^1$H NMR (CDCl$_3$) δ7.71–7.83 (m, 2), 7.66 (t, 1, J=6.6 Hz), 7.42–7.59 (m, 2), 7.17–7.40 (m, 5), 6.85–7.17 (m, 4), 5.63 (m, 1), 5.41 (m, 1), 5.12 (m, 1), 4.57 (t, 1, J=7.5 Hz), 3.35–3.55 (m, 2), 3.17 (m, 1), 3.09 (s, 6), 2.74 (dd, 1, J=12.9, 17.1 Hz), 2.21–2.55 (m, 2), 1.62–2.05 (m, 4); $^{19}$F NMR (CDCl$_3$) δ−76.18; $^{13}$C NMR (CDCl$_3$) δ190.2, 173.9, 171.9, 169.8, 146.3, 137.8, 137.1, 136.4, 135.3, 130.6, 130.5, 129.3, 128.6, 127.4, 127.1, 125.6, 124.9, 124.1, 123.4, 115.7, 51.0, 48.7, 48.5, 44.2, 36.8, 36.5, 25.1, 25.0, 17.1; MS (CI, 70 eV) m/z 586 [M$^+$+H], 182, 166.

EXAMPLE 24

Scheme C, step d and Scheme A, step d: [4S-[4α-7α(R*), 12bβ]]-7-[(1-Oxo-2(S)-(2-pyrrolidino)-acetylthio-3-phenylpropyl)amino]-1,2,3,4,6,7,8,12b-octahydro-6-oxopyrido[2,1-a][2]benzazepine-4-carboxylic acid•trifluoroacetate

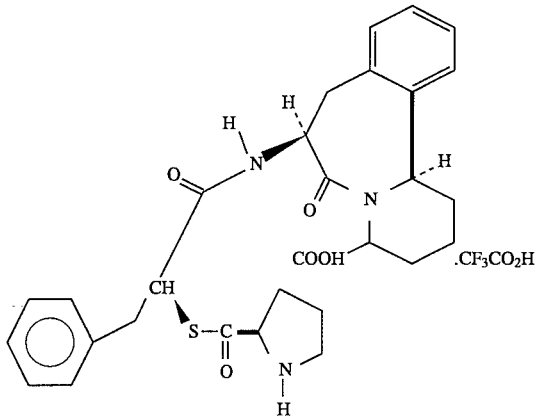

Suspend N-t-butyloxycarbonylproline (4.9 mmol) in degassed dimethylformamide (40 mL) and add carbonyldiimidazole (0.477 g, 2.94 mmol). Stir the reaction mixture at room temperature for 1.5 hours. Add a solution of [4S-[4α -7α(R*), 12bβ]]-7-[(1-Oxo-2(S)-thio-3-phenylpropyl)amino]-1,2,3,4,6,7,8,12b-octahydro-6-oxopyrido[2,1-a][2]benzazepine-4-carboxylic acid, diphenylmethyl ester (2.45 mmol) in degassed tetrahydrofuran and stir at room temperature overnight:. Dilute with ethyl acetate, wash with water (2×) and brine, dry (MgSO$_4$) and evaporate the solvent in vacuo to give

[4S-[4α-7α(R*), 12bβ]]-7-[(1-Oxo-2(S)-(2-(1-t-butyloxycarbonyl)pyrrolidino)-acetylthio-3-phenylpropyl)amino]-1,2,3,4,6,7,8,12b-octahydro-6-oxopyrido[2,1-a][2]benzazepine-4-carboxylic acid, diphenylmethyl ester (65%).

$^1$H NMR (CDCl$_3$) δ7.16–7.46 (m, 10), 6.89 (m, 10), 6.56–6.68 (m, 1), 6.24–6.38 (m, 1), 5.51–5.69 (m, 1), 5.33–5.47 (m, 2), 4.25–4.56 (m, 2), 3.23–3.59 (m, 4), 2.94–3.11 (m, 1), 2.51–2.71 (m, 1), 2.28–2.51 (m, 2), 2.05–2.23 (m, 1), 1.55– 2.03 (m, 7), 1.38–1.52 (m, 9); MS (FAB) m/z 802 [M$^+$+H], 746, 702, 605, 167, 113.

Dissolve [4S-[4α-7α(R*), 12bβ]]-7-[(1-Oxo-2(S)-(2-(1-t-butyloxycarbonyl)pyrrolidino)-acetylthio-3-phenylpropyl)amino] -1,2,3,4,6,7,8,12b-octahydro-6-oxopyrido[2,1-a][2]benzazepine-4-carboxylic acid, diphenylmethyl ester (1.86 mmol) and anisole (1.5 mL, excess) in methylene chloride (20 mL), cool to −50 ° C. and add trifluoroacetic acid (3 mL). Stir the reaction mixture at −50° C. for 2.5 hours, evaporate the solvent in vacuo and triturate with hexane (4×). Take up the residue in a minimal amount of methylene chloride and precipitate from hexane (3×) to give the title compound (73%).

$^1$H NMR (CDCl$_3$) δ7.59–7.69 (m, 1), 6.90–7.40 (m, 9), 5.63–5.69 (m, 1), 5.38–5.51 (m, 1), 5.08–5.19 (m, 1), 4.55–4.68 (m, 1), 4.36–4.48 (m, 1), 3.22–3.49 (m, 2), 3.01–3.15 (m, 1), 2.34–2.95 (m, 5), 1.65–2.16 (m, 8); $^{19}$F NMR (CDCl$_3$) δ− 76.0; $^{13}$C NMR (CDCl$_3$) δ195.5, 173.0, 172.3, 168.8, 136.7, 136.6, 136.0, 130.6, 129.3, 128.6, 127.2, 127.1, 125.8, 125.3, 65.9, 51.7, 51.1, 48.4, 48.2, 45.5, 36.4, 35.9, 28.8, 25.5, 25.3, 23.2, 17.3; MS (FAB) m/z 536 [M$^+$+H].

In a further embodiment, the present invention provides a method of inhibiting enkephalinase in a patient in need thereof comprising administering to said patient an effective enkephalinase inhibitory amount of a compound of Formula (I).

As used herein, the term "patient" refers to warm-blooded animals or mammals, including mice, rats and humans. A patient is in need of treatment to inhibit enkephalinase when the patient is suffering from acute or chronic pain and is in need of an endorphin- or enkephalin-mediated analgesic effect. In addition, a patient is in need of treatment to inhibit enkephalinase when the patient is suffering from a disease state characterized by abnormalities in fluid, electrolyte, blood pressure, intraocular pressure, renin, or aldosterone homeostasis, such as, but not limited to, hypertension, renal diseases, hyperaldosteronemia, cardiac hypertrophy, glaucoma and congestive heart failure. In these instances the patient is in need of an ANP-mediated diuretic, natriuretic, hypotensive, hypoaldosteronemic effect. Inhibition of enkephalinase would provide an endorphin- or enkephalin-mediated analgesic effect by inhibiting the metabolic degradation of endorphins and enkephalins. Inhibition of enkephalinase would provide an ANP-mediated diuretic, natriuretic, hypotensive, hypoaldosteronemic effect by inhibiting the metabolic degradation of ANP. Inhibition of enkephalinase would also potentiate endogenous levels of bradykinin. Inhibition of enkephalinase would also modulate intestinal smooth muscle contractility and would be useful in the treatment of irritable bowel syndrome.

In addition, a patient is in need of treatment to inhibit enkephalinase when the patient is in need of an antidepressant effect or a reduction in severity of withdrawal symptoms associated with termination of opiate or morphine administration.

The identification of those patients who are in need of treatment to inhibit enkephalinase is well within the ability and knowledge of one skilled in the art. A clinician skilled in the art can readily identify, by the use of clinical tests, physical examination and medical/family history, those patients who are in need of an endorphin- or enkephalin-mediated analgesic effect or who are in need of an ANP-mediated diuretic, natriuretic, hypotensive or hypoaldosteronemic effect.

An effective enkephalinase inhibitory amount of a compound of Formula (I) is an amount which is effective in inhibiting enkephalinase and in thus inhibiting the metabolic degradation of the naturally-occurring circulating regulatory peptides such as the endorphins, including enkephalins, and ANP. Successful treatment is also understood to include prophylaxis in treating a patient in those instances such as, for example, in a pre-operative procedure, where a patient will be suffering from acute or chronic pain in the near future.

An effective enkephalinase inhibitory amount of a compound of Formula (I) is an amount which is effective in inhibiting enkephalinase in a patient in need thereof which results, for example, in endorphin- or enkephalin-mediated analgesic effects or in ANP-mediated diuretic, natriuretic, hypotensive, hypoaldosteronemic effect.

An effective enkephalinase inhibitory dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective enkephalinase inhibitory amount of a compound of Formula f I) will generally vary from about 0.01 milligram per kilogram of body weight per day (mg/kg/day) to about 20 mg/kg/day. A daily dose of from about 0.1 mg/kg to about 10 mg/kg is preferred.

In addition, the present invention further provides a method of inhibiting ACE in a patient in need thereof comprising administering to said patient an effective ACE inhibitory amount of a compound of Formula (I). A patient is in need of treatment to inhibit ACE when the patient is suffering from hypertension, chronic congestive heart failure, hyperaldosteronemia or cognitive disorders. Inhibition of ACE reduces levels of angiotensin II and thus inhibits the vasopressor, hypertensive and hyperaldosteronemic effects caused thereby. Inhibition of ACE would also potentiate endogenous levels of bradykinin. An effective ACE inhibitory amount of a compound of Formula (I) is that amount which is effective in inhibiting ACE in a patient in need thereof which results, for example, in a hypotensive effect. An effective ACE inhibitory amount and an effective ACE inhibitory dose are the same as that described above for an effective enkephalinase inhibitory amount and dose.

In addition, the present invention further provides a method for treating a patient suffering from smooth cell proliferation. An effective smooth cell proliferation inhibitory amount of a compound of Formula (I) is that amount which is effective in inhibiting smooth cell proliferation in a patient in need thereof which results, for example, in a reduced myointimal thickening after vascular injury. An effective smooth cell proliferation inhibitory amount and an effective smooth cell proliferation inhibitory dose are the same as that described above for an effective enkephalinase inhibitory amount and dose.

In effecting treatment of a patient, compounds of Formula (I) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing Formulations can readily select the proper form and mode of administration depending upon the disease state to be treated, the stage of the disease, and other relevant circumstances.

Compounds of Formula (I) can be administered in the form of pharmaceutical compositions or medicaments which are made by combining the compounds of Formula (I) with pharmaceutically acceptable carriers or excipients, the proportion and nature of which are determined by the chosen route of administration, and standard pharmaceutical practice.

In another embodiment, the present invention provides compositions comprising a compound of Formula (I) in admixture or otherwise in association with one or more inert carriers. These compositions are useful, for example, as assay standards, as convenient means of making bulk shipments, or as pharmaceutical compositions. An assayable amount of a compound of Formula (I) is an amount which is readily measurable by standard assay procedures and techniques as are well known and appreciated by those skilled in the art. Assayable amounts of a compound of Formula (I) will generally vary from about 0.001% to about 75% of the composition by weight. Inert carriers can be any material which does not degrade or otherwise covalently react with a compound of Formula (I). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising an effective amount of a compound of Formula (I) in admixture or otherwise in association with one or more pharmaceutically acceptable carriers or excipients.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, the compounds of Formula (I) may be incorporated with excipients and used in the form of tablets, troches, capsules, elixirs, suspensions, syrups, wafers, chewing gums and the like. These preparations should contain at least 4% of the compound of Formula (I), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, the compounds of Formula (I) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

As with any group of structurally related compounds which possess a particular generic utility, certain groups and configurations are preferred for compounds of Formula (I) in their end-use application.

The compounds of Formula (1) wherein $B_1$ is hydrogen or alkoxy are preferred. The compounds of Formula (1) wherein $B_2$ is hydrogen or alkoxy are preferred. Compounds of Formula (1) wherein Z is —$CH_2$—, —O— and —S— and X is

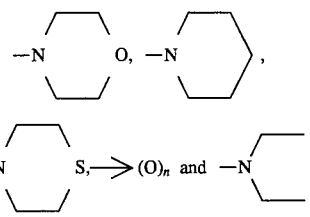

are preferred.

It is, of course, understood that the compounds of Formula (I) may exist in a variety of isomeric configurations including structural as well as stereo isomers. It is further understood that the present invention encompasses those compounds of Formula (I) in each of their various structural and stereo isomeric configurations as individual isomers and as mixtures of isomers.

The following specific compounds of Formula (1) are particularly preferred in the end-use application of the compounds of the present invention:

[4S-[4α-7α(R*), 12bβ]]-7-[(1-Oxo-2(S)-( 4-morpholino)-acetylthio- 3-phenylpropyl)amino]-1,2,3,4,6,7,8,12b-octahydro- 6-oxopyrido [2,1-a][2]benzazepine-4-carboxylic acid;

[4S-[4α-7α(R*), 12bβ]]-7-[(1-Oxo-2(S)-( 4-morpholino)-acetylthio- 3-phenylpropyl)amino ]-1,2,3,4,6,7,8,12b-octahydro- 6-oxopyrido[2,1-a][2]benzazepine-4-carboxylic acid, maleate salt;

[4S-[4α-7α(R*), 12bβ]]-7-[(1-Oxo-2(S)-( 4-morpholino)-acetylthio- 3-phenylpropyl) amino ]-1,2,3,4,6,7,8,12b-hexahydro- 6-oxo-1H-[1,4]-oxazino[3,4-a][2]benzazepine-4carboxylic acid;

[4S-[4α-7α(R*), 12bβ]]-7-[(1-Oxo-2(S)-( 4-morpholino)-acetylthio- 3-phenylpropyl)amino]-1,2,3,4,6,7,8,12b-hexahydro- 6-oxo-1H-[1,4]-thiazino[3,4-a][2]benzazepine-4carboxylic acid;

[4S-[4α-7α(R*), 12bβ]]-7-[(1-Oxo-2(S)-(4-piperidino)-acetylthio- 3-phenylpropyl)amino]-1,2,3,4,6,7,8,12b-octahydro- 6-oxopyrido[2,1-a][2]benzazepine-4-carboxylic acid;

[4S-[4α-7α(R*), 12bβ]]-7-[(1-Oxo-2(S)-(4-piperidino)-acetylthio- 3-phenylpropyl)amino]-1,2,3,4,6,7,8,12b-hexahydro- 6-oxo-1H-[1,4]-oxazino[3,4-a][2]benzazepine-4carboxylic acid;

[4S-[4α-7α(R*), 12bβ]]-7-[(1-Oxo-2(S)-(4-piperidino)-acetylthio- 3-phenylpropyl)amino]-1,2,3,4,6,7,8,12b-hexahydro- 6-oxo-1H-[1H-1,4]-thiazino[3,4-a][2]benzazepine-4-carboxylic acid;

[4S-[4α-7α(R*), 12bβ]]-7-[(1-Oxo-2(S)-(4-thiomorpholino)-acetylthio- 3-phenylpropyl)amino]-1,2,3,4,6,7,8,12b-octahydro- 6-oxopyrido[2,1-a][2]benzazepine-4-carboxylic acid;

[4S-[4α-7α(R*), 12bβ]]-7-[(1-Oxo-2(S)-(4-thiomorpholino)-acetylthio- 3-phenylpropyl)amino]-1,2,3,4,6,7,8,12b-hexahydro- 6-oxo-1H-[1,4]-oxazino[3,4-a][2]benzazepine-4-carboxylic acid;

[4S-[4α-7α(R*), 12bβ]]-7-[(1-Oxo-2(S)-(4-thiomorpholino)-acetylthio- 3-phenylpropyl)amino]-1,2,3,4,6,7,8,12b-hexahydro- 6-oxo-1H-[1,4]-thiazino[3,4-a][2]benzazepine-4-carboxylic acid;

[4S-[4α-7α(R*), 12bβ]]-7-[(1-Oxo-2(S)-(4-thiomorpholino- 1-oxide)-acetylthio-3-phenylpropyl)amino]-1,2,3,4,6,7,8,12b-octahydro-6-oxopyrido[2,1-a][2]benzazepine-4-carboxylic acid;

[4S-[4α-7α(R*), 12bβ]]-7-[(1-Oxo-2(S)-(4-thiomorpholino- 1,1-dioxide)-acetylthio-3-phenylpropyl)amino]-1,2,3,4,6,7,8,12b-octahydro-6-oxopyrido[2,1-a][2]benzazepine-4-carboxylic acid;

[4S-[4α-7α(R*), 12bβ]]-7-[(1-Oxo-2(S)-(diethylamino)-acetylthio- 3-phenylpropyl)amino]-1,2,3,4,6,7,8,12b-octahydro- 6-oxopyrido[2,1-a][2]benzazepine-4-carboxylic acid;

[4S-[4α-7α(R*), 12bβ]]-7-[(1-Oxo-2(S)-(diethylamino)-acetylthio- 3-phenypropyl)amino]-1,2,3,4,6,7,8,12b-hexahydro- 6-oxo-1H-[1,4]-oxazino[3,4-a][2]benzazepine-4carboxylic acid;

[4S-[4α-7α(R*), 12bβ]]-7-[(1-Oxo-2(S)-(diethylamino)-acetylthio- 3-phenylpropyl)amino]-1,2,3,4,6,7,8,12b-hexahydro- 6-oxo-1H-]1,4]-thiazino[3,4-a][2]benzazepine-4-carboxylic acid.

What is claimed is:

1. A composition comprising an assayable amount of a compound of the formula

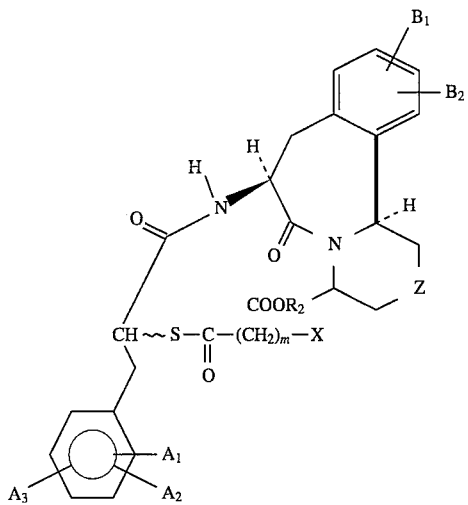

wherein $B_3$ and $B_2$ are each independently hydrogen; hydroxy; $-OR_1$ wherein $R_1$ is a $C_1-C_4$ alkyl or an Ar—Y— group wherein Ar ifs phenyl or naphthyl group unsubstituted or substituted with from one to three substituents selected from the group consisting of methylenedioxy, hydroxy, $C_1-C_4$ alkoxy, fluoro and chloro and Y is a $C_0-C_4$ alkyl; or, Where $B_1$ and $B_2$ are attached to adjacent carbon atoms, $B_1$ and $B_2$ can be taken together with said adjacent carbons to form a benzene ring or methylenedioxy;

$A_1$, $A_2$ and $A_3$ are each independently hydrogen; hydroxy; nitro; amino; fluoro, chloro, $-OR_1$ of an Ar—Y group; or, where $A_1$ and $A_2$ are attached to adjacent carbon atoms, $A_1$ and $A_2$ can be taken together with said adjacent carbons to form a benzene ring or methylenedioxy;

$R_2$ is hydrogen, a $C_1-C_4$ alkyl, an Ar—Y— qroup or $-CH_2O-C(O)(CH_3)_3$;

Z is $-CH_2-$, $-O-$, $-S-$,

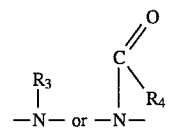

or a bond wherein $R_3$ is hydrogen, a $C_1-C_4$ alkyl or an Ar—Y— group and $R_4$ is $-CF_3$, a $C_1-C_{10}$ alkyl or an Ar—Y— group;

m is an integer 0 to 5;

X is selected from the group consisting of

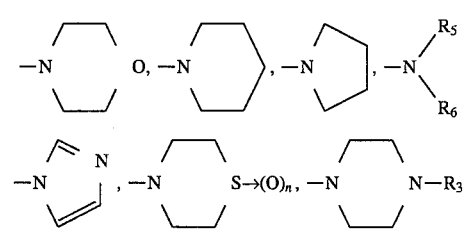

-continued
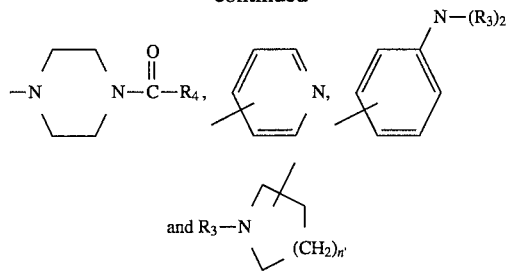
wherein
$R_5$ and $R_6$ are each independently a $C_1$–$C_4$ alkyl or an Ar—Y— group and n is an integer 0–2; n' is an integer 1–2; and the pharmaceutically acceptable salts thereof in admixture or otherwise in association with an inert carrier.
* * * * *

UNITED STATES PATENT AND TRADEMARK OFFICE
CERTIFICATE OF CORRECTION

PATENT NO. : 5,488,048

DATED : January 30, 1996

INVENTOR(S) : Gary A. Flynn et al.

It is certified that error appears in the above-identified patent and that said Letters Patent is hereby corrected as shown below:

On the title page: Item [56] Reference Cited: Add

U.S. PATENT DOCUMENTS

| Patent No. | Date | Inventor |
|---|---|---|
| 4,584,294 | 4/1986 | Ruyle |
| 4,973,585 | 11/1990 | Flynn et al. |
| 4,824,832 | 4/1989 | Flynn et al. |
| 4,772,701 | 9/1988 | Attwood et al. |
| 4,512,924 | 4/1985 | Attwood et al. |
| 4,658,024 | 4/1987 | Attwood et al. |
| 4,808,713, | 2/1989 | Attwood et al. |
| 4,415,496, | 11/1983 | Harris et al. |
| 5,208,230, | 5/1993, | Flynn et al. |
| 4,391,752, | 7/1983, | Crossley |
| 4,320,057, | 3/1982, | Freed et al. |
| 3,334,095, | 8/1967, | Houlihan et al. |
| 3,334,091, | 8/1967, | Houlihan, et al. |
| 4,399,136, | 8/1983, | Hassall et al. |
| 4,487,929, | 12/1984, | Hassall et al. |
| 4,692,438, | 9/1987, | Hassall et al. |
| 4,716,232, | 12/1987, | Ternansky |
| 4,734,504, | 3/1988, | Holmes |
| 4,734,505, | 3/1988, | Holmes |
| 4,762,924, | 8/1988, | Hassall et al. |
| 4,782,149, | 11/1988, | Lawton et al. |
| 4,785,093, | 11/1988, | Hassall et al. |
| 4,826,980, | 5/1989, | Hassall et al. |
| 4,080,449, | 3/1994, | Croisier et al. |
| 5,238,932, | 8/1993, | Flynn et al. |

UNITED STATES PATENT AND TRADEMARK OFFICE
CERTIFICATE OF CORRECTION

PATENT NO. : 5,488,048

DATED : January 30, 1996

INVENTOR(S) : Gary A. Flynn et al.

It is certified that error appears in the above-identified patent and that said Letters Patent is hereby corrected as shown below:

Additions that should have been listed on front of patent as "References Cited":

FOREIGN PATENT DOCUMENTS

| | | |
|---|---|---|
| 0249223 | 12/1987 | European Pat. Off. |
| 9109840 | 7/1991 | WIPO |
| 0249224 | 12/1987 | European Pat. Off. |
| 9108195 | 6/1991 | WIPO |
| 0481522 | 4/1992 | European Pat. Off. |
| 0492369 | 7/1992 | European Pat. Off. |
| 0533084 | 9/1992 | European Pat. Off. |
| 0322914 | 12/1988 | European Pat. Off. |
| 0128728 | 12/1984 | European Pat. Off. |
| 9302099 | 2/1993 | WIPO |
| 0599444 | 6/1994 | European Pat. Off. |

OTHER PUBLICATIONS

Flynn, et al., *J. Am. Chem. Soc.*, 109, 7914 (1987).

Flynn, et al., *Peptide Chemistry*, pg. 631-636 (1987), Shiba & Sakakibara (Ed.), Protein Research Foundation, Osaka (1988).

Flynn, et al., *Tetrahedron Letters*, Vol. 31(6), 815-88 (1990).

Attwood, et al., *J. Chem. Soc. Perkin Trans I*, 1011-19 (1986).

Natoff, et al., *Drugs of the Future*, 12(5):475-483 (1987).

Flynn, et al., *Bioorganic & Medicinal Chem Letter*, Vol 1, No. 6, pp 309 - 312.

UNITED STATES PATENT AND TRADEMARK OFFICE
CERTIFICATE OF CORRECTION

PATENT NO. : 5,488,048

DATED : January 30, 1996

INVENTOR(S) : Gary A. Flynn et al.

It is certified that error appears in the above-identified patent and that said Letters Patent is hereby corrected as shown below:

Ocain, et al., *J. Med. Chem.*, 1992, Vol. 35, No. 5, pp 823-832.

Powell, Jerry S. et al, *Journal of American College of Cardiology*, Vol. 17, No. 6, pp 137B-152B (May 1991).

*Supplement I Circulation*, Vol. 86(4), pg. I-220 (0873), October 1992.

Fournie-Zaluski, Marie-Claude et al., *J. Med. Chem.*, 1992 Vol.35, pp 2473-2481.

Fournie-Zaluski, Marie-Claude et al., *J. Med. Chem.*, 1992 Vol.35, pp 1259-1266.

French, John F., *Jour. of Pharm and Exper. Therapeutics*, Vol. 268, No.1, pp. 180-186.

W.H. Parsons et al., *Biochemical and Biophysical Research Communications* Vol. 117, No. 1, 1993 (Nov. 30, 1983).

Burkholder, et al., *Bioorganic and Medical Chem. Letters*, Vol. 3, No. 2, pp 231-234, 1993.

Flynn et al., *J. Med. Chem.*, 1993, 36 2420-2423.

UNITED STATES PATENT AND TRADEMARK OFFICE
CERTIFICATE OF CORRECTION

PATENT NO. : 5,488,048

DATED : January 30, 1996

Page 4 of 12

INVENTOR(S) : Gary A. Flynn et al.

It is certified that error appears in the above-identified patent and that said Letters Patent is hereby corrected as shown below:

```
Column 1, Line 56, patent reads  "7 469"  and should
read    --  7, 469  -- .

Column 11, Line 8, patent reads  "is an 1 or 2"
and should read  --  is 1 or 2  -- .

Column 11, Line 60, patent reads  "step a"  and
should read  --  step c  -- .

Column 16, Line 20, patent reads   "the-
appropriate"  and should read  --  the
appropriate  -- .

Column 17, Line 55, patent reads  "an general"
and should read  --  a general  -- .

Column 23, Line 37, patent reads  "arid"  and
should read  --  and  -- .

Column 23, Line 38, patent reads  "methelene"
and should read  --  methylene  -- .

Column 26, Line 44, patent reads
"morpholinethiolacetate"  and should read  --  4-
morpholinethiolacetate  -- .

Column 26, Line 49, patent reads  "-6oxopyrido"
and should read  --  -6-oxopyrido  -- .
```

UNITED STATES PATENT AND TRADEMARK OFFICE
CERTIFICATE OF CORRECTION

PATENT NO. : 5,488,048

DATED : January 30, 1996

INVENTOR(S) : Gary A. Flynn et al.

It is certified that error appears in the above-identified patent and that said Letters Patent is hereby corrected as shown below:

Column 26, Line 58, patent reads "3,phenylpropyl" and should read -- 3-phenylpropyl -- .

Column 27, Line 1, patent reads "1 minutes" and should read -- 1 minute -- .

Column 27, Line 61, patent reads "137,47" and should read -- 137.47 -- .

Column 28, Line 3, patent reads "amino)-amino]-1" and should read -- amino]-1 -- .

Column 28, Line 45, patent reads "phenylpropl" and should read -- phenylpropyl -- .

Column 29, line 39, patent reads "oxoryrido" and should read -- oxopyrido -- .

Column 29, Line 65, patent reads "extraces" and should read --extracts -- .

Column 31, Line 3, patent reads "seriner" and should read -- serine -- .

Column 31, Line 9, patent reads "phthaloy" and should read -- phthaloyl -- .

Column 31, Line 25, patent reads "1,3Dihydro" and should read -- 1,3-Dihydro -- .

Column 31, Line 33, patent reads "trifluoromethanesuihfonic" and should read -- trifluoromethanesulfonic -- .

UNITED STATES PATENT AND TRADEMARK OFFICE
CERTIFICATE OF CORRECTION

PATENT NO. : 5,488,048

DATED : January 30, 1996

INVENTOR(S) : Gary A. Flynn et al.

It is certified that error appears in the above-identified patent and that said Letters Patent is hereby corrected as shown below:

Column 31, Line 63, patent reads "oxo3-" and should read -- oxo-3- -- .

Column 32, Line 25, patent reads "t he" and should read -- the -- .

Column 32, Line 45, patent reads "(R8)" and should read -- (R*) -- .

Column 32, Line 67, patent reads "-4carboxylic" and should read -- -4-carboxylic -- .

Column 32, Line 67, patent reads "diphenylmethyl ester" and should read -- diphenylmethyl ester (10mmol), (R)-3-phenyl-2-bromopropionic acid (2.75g, 12mmol), 2-ethoxy-2-ethoxycarbonyl-1,2-dihydro-quinoline (EEDQ) (3.0g, 12mmol) and methylene chloride (25mL). Stir at room temperature for 4 hours, dilute with methylene chloride, wash with 10% hydrochloric acid, saturated sodium hydrogen carbonate and brine. Dry (MgSO$_4$) and evaporate the solvent in vacuo. Purify by chromatography to give the title compound. -- .

Column 33, Lines 1 through 12, patent reads "Mix...compound." and should be deleted.

Column 33, Line 60, patent reads "1 minutes" and should read -- 1 minute -- .

Column 34, Line 35, patent reads "4carboxylic" and should read -- 4-carboxylic -- .

UNITED STATES PATENT AND TRADEMARK OFFICE
CERTIFICATE OF CORRECTION

PATENT NO. : 5,488,048

DATED : January 30, 1996

INVENTOR(S) : Gary A. Flynn et al.

It is certified that error appears in the above-identified patent and that said Letters Patent is hereby corrected as shown below:

Column 34, Line 48, patent reads "-3phenypropyl" and should read -- -3-phenylpropyl -- .

Column 34, Line 56, patent reads "4-morpholinethiolacetate (1.61 g" and should read -- 4-morpholinethiolacetate (1.61g -- .

Column 35, Line 4, patent reads "-4carboxylic" and should read -- -4-carboxylic -- .

Column 35, Line 24, patent reads "-oxopyyrido[2]" and should read -- -oxopyrido[2,1-a][2] -- .

Column 35, Line 47, patent reads "caroxylic" and should read -- carboxylic -- .

Column 36, Line 14, patent reads "(4-piperidino 1-acetylthio" and should read -- (4-peperidino)-acetylthio -- .

Column 36, Line 15, patent reads "6,8, and should read -- 6,7,8, -- .

Column 36, Line 16, patent reads "-oxopyridol" and should read -- -oxopyrido -- .

Column 39, Line 2 of the patent reads "thiomorpholinethietate" and should read -- thiomorpholinethiolacetate -- .

UNITED STATES PATENT AND TRADEMARK OFFICE
CERTIFICATE OF CORRECTION

PATENT NO. : 5,488,048

DATED : January 30, 1996

INVENTOR(S) : Gary A. Flynn et al.

It is certified that error appears in the above-identified patent and that said Letters Patent is hereby corrected as shown below:

Column 39, Line 19, patent reads "thiomorpholinol-" and should read -- thiomorpholino)- -- .

Column 39, Line 40, patent reads "(CDCl$_{13}$)$\delta$87.44" and should read -- (CDCl$_3$)$\delta$7.44 -- .

Column 39, Line 42, patent reads "(m,)" and should read -- (m,1), -- .

Column 39, Line 49, patent reads "thiomorpholinol)" and should read -- thiomorpholino) -- .

Column 40, Line 63, patent reads "1 minutes" and should read -- 1 minute -- .

Column 42, Line 1, patent reads "]]1-" and should read -- ]]-7- -- .

Column 42, Line 4, patent reads "6-oxopyridol-a][2]" and should read -- 6-oxopyrido[2,1-a][2] -- .

Column 42, Line 39, patent reads "1Oxo" and should read -- 1-Oxo -- .

Column 43, Line 22, patent reads "-a]benzazepine" and should read -- -a][2]benzazepine -- .

Column 45, Line 6, patent reads "-2,3," and should read -- -1,2,3, -- .

Column 45, Line 12, patent reads "-3phenylpropyl" and should read -- -3-phenylpropyl -- .

UNITED STATES PATENT AND TRADEMARK OFFICE
CERTIFICATE OF CORRECTION

PATENT NO. : 5,488,048

DATED : January 30, 1996

INVENTOR(S) : Gary A. Flynn et al.

It is certified that error appears in the above-identified patent and that said Letters Patent is hereby corrected as shown below:

Column 45, Line 37, patent reads "$\delta83.36$" and should read -- $\delta3.36$ -- .

Column 45, Line 41, patent reads "H, 6.2" and should read -- H, 6.21 -- .

Column 46, Line 12, patent reads "2,1a]" and should read -- 2,1-a] -- .

Column 46, Line 23, patent reads "677.71" and should read -- $\delta7.71$ -- .

Column 46, Line 32, patent reads "$C_{30}H_{35}N_3S_2$" and should read -- $C_{30}H_{35}N_3O_7S_2$ -- .

Column 46, Line 61, patent reads "3,phenylpropyl" and should read -- 3-phenylpropyl -- .

Column 47, Line 61, patent reads "3.8-7-4.06" and should read -- 3.87-4.06 -- .

Column 49, Line 45, patent reads "in to" and should read -- into -- .

Column 52, Line 2, patent reads "acetyithio" and should read -- acetylthio -- .

Column 52, Line 28, patent reads "solve it" and should read -- solvent -- .

Column 52, Line 36, patent reads "138,23" and should read -- 138.23 -- .

UNITED STATES PATENT AND TRADEMARK OFFICE
CERTIFICATE OF CORRECTION

PATENT NO. : 5,488,048

DATED : January 30, 1996

INVENTOR(S) : Gary A. Flynn et al.

It is certified that error appears in the above-identified patent and that said Letters Patent is hereby corrected as shown below:

Column 52, Line 64, patent reads "them under" and should read -- then under -- .

Column 53, Line 37, patent reads "off" and should read -- of -- .

Column 53, Line 37, patent reads "(1Oxo" and should read -- (1-Oxo -- .

Column 53, Line 39, patent reads "a]8 2]" and should read -- a][2] -- .

Column 53, Line 40, patent reads "diphenylmethyl (2.45" and should read -- diphenylmethyl ester (2.45 -- .

Column 53, Line 50, patent reads "1J=" and should read -- 1, J= -- .

Column 54, Line 5, patent reads "solvent vacuo" and should read -- solvent in vacuo -- .

Column 54, Line 60, patent reads "3.0 4" and should read -- 3.04 -- .

Column 55, Line 20, patent reads "3-phenylpropul" and should read -- 3-phenylpropyl -- .

Column 55, Line 30, patent reads "($CDCl_{13}$)" and should read -- ($CDCl_3$) -- .

Column 56, Line 56, patent reads "8-76.-9; $^3C$" and should read -- $\delta$-76.9; $^{13}C$ -- .

UNITED STATES PATENT AND TRADEMARK OFFICE
CERTIFICATE OF CORRECTION

PATENT NO. : 5,488,048

DATED : January 30, 1996

INVENTOR(S) : Gary A. Flynn et al.

It is certified that error appears in the above-identified patent and that said Letters Patent is hereby corrected as shown below:

```
Column 57, Line 53, patent reads  "306," and should read
--  3067,  -- .

Column 58, Line 11, patent reads  "anizole" and should
read  --  anisole  -- .

Column 58, Line 58, patent reads
"butylcxycarbonylproline" and should read  --
butyloxycarbonylproline  -- .

Column 60, Line 37, patent reads  "f I)" and should read
--  (I)  -- .

Column 63, Line 7, patent reads  "6-oxopyridc" and should
read  --  6-oxopyrido  -- .

Column 63, Line 16, patent reads  "-4carboxylic" and
should read  --  -4-carboxylic  -- .

Column 63, Line 19, patent reads  "-4carboxylic" and
should read  --  -4-carboxylic  -- .

Column 63, Line 28, patent reads  "-4carboxylic" and
should read  --  -4-carboxylic  -- .

Column 63, Line 30, patent reads  "-1H-[1H-1,4]" and
should read  --  -1H-[1,4]  -- .

Column 63, Line 60, patent reads  "-4carboxylic" and
should read  --  -4-carboxylic  -- .
```

UNITED STATES PATENT AND TRADEMARK OFFICE
CERTIFICATE OF CORRECTION

PATENT NO.  : 5,488,048

DATED       : January 30, 1996

INVENTOR(S) : Gary A. Flynn et al.

It is certified that error appears in the above-identified patent and that said Letters Patent is hereby corrected as shown below:

Column 64, Line 21, patent reads "$B_3$ and $B_2$" and should read -- $B_1$ and $B_2$ -- .

Column 64, Line 25, patent reads "ifs" and should read -- is -- .

Column 64, Line 41, patent reads "$-CH_2O-C(O)(CH_3)_3$" and should read -- $-CH_2O-C(O)C(CH_3)_3$ -- .

Signed and Sealed this

Eighth Day of April, 1997

Attest:

BRUCE LEHMAN

*Attesting Officer*    *Commissioner of Patents and Trademarks*